(12) United States Patent
Pelcman et al.

(10) Patent No.: US 11,427,539 B2
(45) Date of Patent: Aug. 30, 2022

(54) BETA-HYDROXY HETEROCYCLIC AMINES AND THEIR USE IN THE TREATMENT OF HYPERGLYCAEMIA

(71) Applicant: ATROGI AB, Stockholm (SE)

(72) Inventors: Benjamin Pelcman, Stockholm (SE); Tore Bengtsson, Vaxholm (SE)

(73) Assignee: ATROGI AB, Stockholm (SE)

( * ) Notice: Subject to any disclaimer, the term of this patent is extended or adjusted under 35 U.S.C. 154(b) by 0 days.

(21) Appl. No.: 16/646,050

(22) PCT Filed: Sep. 13, 2018

(86) PCT No.: PCT/GB2018/052593
§ 371 (c)(1),
(2) Date: Mar. 10, 2020

(87) PCT Pub. No.: WO2019/053425
PCT Pub. Date: Mar. 21, 2019

(65) Prior Publication Data
US 2020/0277259 A1  Sep. 3, 2020

(30) Foreign Application Priority Data
Sep. 13, 2017  (GB) ........................... 1714740

(51) Int. Cl.
| C07D 211/22 | (2006.01) |
| A61K 31/40 | (2006.01) |
| A61K 31/445 | (2006.01) |
| C07D 207/08 | (2006.01) |

(52) U.S. Cl.
CPC ............ C07D 211/22 (2013.01); A61K 31/40 (2013.01); A61K 31/445 (2013.01); C07D 207/08 (2013.01)

(58) Field of Classification Search
None
See application file for complete search history.

(56) References Cited

U.S. PATENT DOCUMENTS

| 2,308,232 A | 1/1943 | Scheuing et al. |
| 2,460,144 A | 1/1949 | Moore |
| 3,056,836 A | 10/1962 | Hendrik |
| 3,341,594 A | 9/1967 | Otto et al. |
| 3,410,944 A | 11/1968 | Claassen et al. |
| 3,801,631 A | 4/1974 | Comer et al. |
| 3,910,934 A | 10/1975 | Sankey et al. |
| 3,952,101 A | 4/1976 | Jen et al. |
| 3,954,871 A | 5/1976 | Buu-Hoi et al. |
| 3,985,887 A | 10/1976 | Kaiser et al. |
| 4,024,156 A | 5/1977 | Bagli et al. |
| 4,119,710 A | 10/1978 | Engelhardt et al. |
| 4,223,137 A | 9/1980 | Yoshizaki et al. |
| 4,244,967 A | 1/1981 | Engelhardt et al. |
| 4,248,884 A | 2/1981 | Legrand et al. |
| 4,743,604 A | 5/1988 | Alig et al. |
| 4,835,315 A | 5/1989 | Lafon |
| 4,927,836 A | 5/1990 | Holloway et al. |
| 5,019,578 A | 5/1991 | Fisher et al. |
| 5,061,727 A | 10/1991 | Bloom et al. |
| 5,705,515 A | 1/1998 | Fisher et al. |
| 6,346,532 B1 | 2/2002 | Maruyama et al. |
| 6,403,612 B2 * | 6/2002 | Nantermet ............. A61K 45/06 514/317 |
| 7,795,310 B2 | 9/2010 | Lee et al. |
| 9,657,348 B2 | 5/2017 | Bengtsson |
| 9,784,726 B2 | 10/2017 | Bengtsson |
| 9,891,212 B2 | 2/2018 | Bengtsson |
| 10,288,602 B2 | 5/2019 | Bengtsson |
| 11,357,757 B2 | 6/2022 | Pelcman et al. |
| 2001/0044454 A1 | 11/2001 | Nantermet et al. |
| 2003/0018061 A1 | 1/2003 | Ogawa et al. |
| 2004/0105819 A1 | 6/2004 | Hale et al. |
| 2004/0266867 A1 | 12/2004 | Cheng et al. |
| 2005/0250944 A1 | 11/2005 | Chen |
| 2006/0223886 A1 | 10/2006 | Dargazanli et al. |
| 2008/0306160 A1 | 12/2008 | Kobayashi et al. |
| 2009/0181976 A1 | 7/2009 | Buschmann et al. |
| 2010/0022658 A1 | 1/2010 | Epstein et al. |
| 2010/0022659 A1 | 1/2010 | Meyerson et al. |
| 2010/0173928 A1 | 7/2010 | Sabatini et al. |

(Continued)

FOREIGN PATENT DOCUMENTS

| AT | 285583 B | 11/1970 |
| BE | 823841 A | 4/1975 |

(Continued)

OTHER PUBLICATIONS

Besev et al, Organic Letters, 4 (18), 3023-3025 (Year: 2002).*

(Continued)

*Primary Examiner* — Zinna Northington Davis

(74) *Attorney, Agent, or Firm* — McCarter & English, LLP; Steven G. Davis; Mei Bai

(57) ABSTRACT

There is herein provided a compound of formula (I) or a pharmaceutically acceptable salt thereof, wherein X, $R^1$, ring A, m and n have meanings as provided in the description.

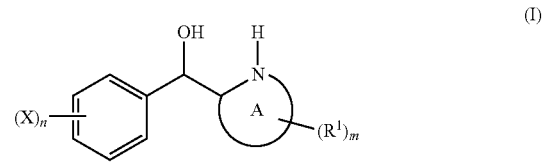

(I)

16 Claims, No Drawings

(56) References Cited

U.S. PATENT DOCUMENTS

| | | |
|---|---|---|
| 2011/0306552 A1 | 12/2011 | Rao et al. |
| 2013/0331433 A1 | 12/2013 | Thibonnier |
| 2017/0153225 A1 | 6/2017 | Bengtsson |
| 2019/0119196 A1 | 4/2019 | Pelcman et al. |
| 2019/0314301 A1 | 10/2019 | Pelcman et al. |
| 2020/0268687 A1 | 8/2020 | Pelcman et al. |
| 2020/0268688 A1 | 8/2020 | Pelcman et al. |
| 2020/0315993 A1 | 10/2020 | Pelcman et al. |
| 2021/0030731 A1 | 2/2021 | Pelcman et al. |
| 2021/0338603 A1 | 11/2021 | Pelcman et al. |
| 2022/0133703 A1 | 5/2022 | Pelcman et al. |
| 2022/0152004 A1 | 5/2022 | Pelcman et al. |

FOREIGN PATENT DOCUMENTS

| | | |
|---|---|---|
| CN | 103565784 A | 2/2014 |
| CN | 105078946 A | 11/2015 |
| CN | 106083837 A | 11/2016 |
| DE | 638650 C | 11/1936 |
| DE | 45721 A | 11/1966 |
| DE | 2015573 A1 | 10/1970 |
| DE | 2128258 A1 | 12/1971 |
| DE | 2157040 A1 | 5/1973 |
| DE | 2212600 A1 | 9/1973 |
| DE | 2259282 A1 | 6/1974 |
| DE | 2300614 A1 | 7/1974 |
| DE | 2413102 A1 | 10/1975 |
| DE | 2548053 A1 | 5/1976 |
| DE | 2700193 A1 | 7/1977 |
| DE | 2819458 A1 | 11/1978 |
| DE | 4209989 A1 | 10/1992 |
| EP | 0023385 A1 | 2/1981 |
| EP | 0043807 A2 | 1/1982 |
| EP | 0128120 A2 | 12/1984 |
| EP | 0195396 A1 | 9/1986 |
| EP | 0272976 A2 | 6/1988 |
| EP | 0290122 A1 | 11/1988 |
| EP | 0303546 A2 | 2/1989 |
| EP | 0357956 A2 | 3/1990 |
| EP | 0436435 A1 | 7/1991 |
| EP | 0543662 A2 | 5/1993 |
| EP | 0611003 A1 | 8/1994 |
| EP | 0659737 A2 | 6/1995 |
| EP | 1095932 A1 | 5/2001 |
| EP | 1277736 A1 | 1/2003 |
| EP | 1829534 A1 | 9/2007 |
| EP | 2426202 A1 | 3/2012 |
| FR | 1324914 A | 4/1963 |
| FR | 2647310 A1 | 11/1990 |
| GB | 1199630 A | 7/1970 |
| GB | 2054581 A | 2/1981 |
| GB | 2133986 A | 8/1984 |
| GB | 2151612 A | 7/1985 |
| JP | 52-105138 A | 9/1977 |
| JP | S56055355 A | 5/1981 |
| JP | H08-239349 A | 9/1996 |
| JP | 2005-097149 A | 4/2005 |
| JP | 2007-217368 A | 8/2007 |
| JP | 2008-505176 A | 2/2008 |
| NL | 7804582 A | 11/1978 |
| RU | 2095344 C1 | 11/1997 |
| WO | WO-1991/09596 | 7/1991 |
| WO | WO-1993/15041 | 8/1993 |
| WO | WO-1996/04234 | 2/1996 |
| WO | WO-1997/25311 | 7/1997 |
| WO | WO-1998/22480 | 5/1998 |
| WO | WO-1998/32753 | 7/1998 |
| WO | WO-1999/20607 | 4/1999 |
| WO | WO-1999/35279 | 7/1999 |
| WO | WO-1999/43326 | 9/1999 |
| WO | 1999/65311 A1 | 12/1999 |
| WO | WO-1999/65308 | 12/1999 |
| WO | WO-1999/65877 | 12/1999 |
| WO | WO-2000/075114 | 12/2000 |
| WO | WO-2001/74782 | 10/2001 |
| WO | WO-2002/032897 | 4/2002 |
| WO | WO-2003/032969 | 4/2003 |
| WO | 2003/101958 A2 | 12/2003 |
| WO | WO-2004/004451 | 1/2004 |
| WO | 2004/022566 A1 | 3/2004 |
| WO | WO-2004/071388 | 8/2004 |
| WO | WO-2004/110375 | 12/2004 |
| WO | WO-2005/013666 | 2/2005 |
| WO | WO-2005/025570 | 3/2005 |
| WO | 2005/037781 A2 | 4/2005 |
| WO | 2005/075458 A1 | 8/2005 |
| WO | 2005/108381 A1 | 11/2005 |
| WO | 2005/111002 A2 | 11/2005 |
| WO | WO-2005/102350 | 11/2005 |
| WO | WO-2005/110990 | 11/2005 |
| WO | WO-2005/114195 | 12/2005 |
| WO | 2006/04803 A1 | 1/2006 |
| WO | WO-2006/027579 | 3/2006 |
| WO | WO-2006/122788 | 11/2006 |
| WO | 2007/011065 A2 | 1/2007 |
| WO | 2007/026630 A1 | 3/2007 |
| WO | WO-2007/102011 | 9/2007 |
| WO | WO-2007/109882 | 10/2007 |
| WO | WO-2008/011453 | 1/2008 |
| WO | WO-2008/022038 | 2/2008 |
| WO | WO-2008/071948 | 6/2008 |
| WO | WO-2009/124166 | 10/2009 |
| WO | WO-2009/124167 | 10/2009 |
| WO | WO-2009/156413 | 12/2009 |
| WO | 2010/16939 A1 | 2/2010 |
| WO | 2011/037815 A1 | 3/2011 |
| WO | WO-2011/025960 | 3/2011 |
| WO | WO-2011/112867 | 9/2011 |
| WO | 2012/064269 A1 | 5/2012 |
| WO | 2014/108449 A1 | 7/2014 |
| WO | WO-2018/011588 | 1/2018 |
| WO | 2019/053425 A1 | 3/2019 |
| ZA | 8703195 | 10/1987 |

OTHER PUBLICATIONS

Ookawa et al, Journal of the Chemical Society, Perkin Transactions 1: Organic and Bio-Organic Chemistry (1972-1999), (7), 1465-71 (Year: 1987).*

Allen et al., Studies on the inhibition of glucose metabolism in isolated fat cells by beta-adrenergic blocking agents. Biochem Pharmacol. Jun. 1969;18(6):1347-54.

Bercher et al., Wirkung fluorierter Phenyläthanolamine auf eine durch Katecholamine induzierte Hyperglykämie bei Ratten [The effect of fluoridated phenylethanolamines on hyperglycemia induced by catecholamines in the rat]. Acta Biol Med Ger. 1975;34(4):667-74.

Cooperberg et al., Terbutaline and the prevention of nocturnal hypoglycemia in type 1 diabetes. Diabetes Care. Dec. 2008;31(12):2271-2.

Satoh, Glycemic effects of solanine in rats. Jpn J Pharmacol. Dec. 1967;17(4):652-8.

Star et al., Glucocorticoid-associated maternal hyperglycemia: a randomized trial of insulin prophylaxis. J Matern Fetal Med. Sep.-Oct. 2000;9(5):273-7.

Ahren et al., Adrenergic innervation of pancreatic islets and modulation of insulin secretion by the sympatho-adrenal system. Cell Tissue Res. 1981;216(1):15-30.

Alessi et al., Characterization of a 3-phosphoinositide-dependent protein kinase which phosphorylates and activates protein kinase Balpha. Curr Biol. Apr. 1, 1997;7(4):261-9.

Arch et al., Prospects for beta3-adrenoceptor agonists in the treatment of obesity and diabetes. International Journal of Obesity. 1996;20:191-199.

Baker et al., Chronic treatment with the beta(2)-adrenoceptor agonist prodrug BRL-47672 impairs rat skeletal muscle function by inducing a comprehensive shift to a faster muscle phenotype. J Pharmacol Exp Ther. Oct. 2006;319(1):439-46.

Barnes et al., Activation of GLUT1 by metabolic and osmotic stress: potential involvement of AMP-activated protein kinase (AMPK). J Cell Sci. Jun. 1, 2002;115(Pt 11):2433-42.

(56) References Cited

OTHER PUBLICATIONS

Baur et al., The identification of indacaterol as an ultralong-acting inhaled beta2-adrenoceptor agonist. J Med Chem. May 13, 2010;53(9):3675-84.

Beak et al., alpha.-Lithioamine synthetic equivalents: syntheses of diastereoisomers from the Boc-piperidines. J Org Chem. Apr. 1, 1990;55(9):2578-2580.

Bentzinger et al., Skeletal muscle-specific ablation of raptor, but not of rictor, causes metabolic changes and results in muscle dystrophy. Cell Metab. Nov. 2008;8(5):411-24.

Biel et al., Bronchodilators, N-substituted derivatives of 1-(3',4'-Dihydroxyphenyl)-2-aminoethanol (Arterenol). J Am Chem Soc. Jun. 1954;76:3149-53.

Brittain et al., Sympathomimetic bronchodilator drugs. Pharmacol Ther B. 1976;2(3):423-462.

Brown et al., A mammalian protein targeted by G1-arresting rapamycin-receptor complex. Nature. Jun. 30, 1994;369(6483):756-8.

Bryant et al., Regulated transport of the glucose transporter GLUT4. Nat Rev Mol Cell Biol. Apr. 2002;(4):267-77.

Cannon et al., Brown adipose tissue: function and physiological significance. Physiol Rev. Jan. 2004;84(1):277-359.

Carayannopoulos et al., GLUT8 is a glucose transporter responsible for insulin-stimulated glucose uptake in the blastocyst. Proc Natl Acad Sci U S A. Jun. 20, 2000;97(13):7313-8.

Castle et al., Attenuation of insulin resistance by chronic beta2-adrenergic agonist treatment possible muscle specific contributions. Life Sci. Jun. 22, 2001;69(5):599-611.

Chandler et al., Expression and localization of GLUT1 and GLUT12 in prostate carcinoma. Cancer. Apr. 15, 2003;97(8):2035-42.

Chariot et al., Effects of CRL 40827 and salbutamol on exocrine pancreatic secretion in rats. Eur J. Pharmacol. Jan. 27, 1988;146(1):17-25.

Chernogubova et al., Alpha1- and beta1-adrenoceptor signaling fully compensates for beta3-adrenoceptor deficiency in brown adipocyte norepinephrine-stimulated glucose uptake. Endocrinology. May 2005;146(5):2271-84.

Chernogubova et al., Norepinephrine increases glucose transport in brown adipocytes via beta3-adrenoceptors through a cAMP, PKA, and PI3-kinase-dependent pathway stimulating conventional and novel PKCs. Endocrinology. Jan. 2004;145(1):269-80.

Cioc et al., One-Pot Synthesis of N-Substituted beta-Amino Alcohols from Aldehydes and Isocyanides. Chemistry. 2015;21(21):7808-7813. Including supporting information.

Conde et al., beta-Adrenoceptor blocking activity of halogenated thienylethanolamine derivatives. J Med Chem. Jul. 1977;20(7):970-4.

Copp et al., TORC-specific phosphorylation of mammalian target of rapamycin (mTOR): phospho-Ser2481 is a marker for intact mTOR signaling complex 2. Cancer Res. Mar. 1, 2009;69(5):1821-7.

Cypress et al., Activation of Human Brown Adipose Tissue by a beta3-Adrenergic Receptor Agonist. Cell Metab. Jan. 2015. 21(1):33-38.

Dallner et al., Beta3-adrenergic receptors stimulate glucose uptake in brown adipocytes by two mechanisms independently of glucose transporter 4 translocation. Endocrinology. Dec. 2006;147(12):5730-9.

De Souza et al., Beta 3-adrenoceptor agonists as anti-diabetic and anti-obesity drugs in humans. Curr Pharm Des. Sep. 2001;7(14):1433-49.

Defronzo et al., Synergistic Interaction between Exercise and Insulin on Peripheral Glucose Uptake. J Clin Invest. Dec. 1981;68:1468-74.

Dehvari et al., beta(2)-Adrenoceptors increase translocation of GLUT4 via GPCR kinase sites in the receptor C-terminal tail. Br J Pharmacol. Mar. 2012;165(5):1442-56.

Drake et al., Trafficking of G protein-coupled receptors. Circ Res. Sep. 15, 2006;99(6):570-82.

Edmondson et al., Discovery of Vibegron: A Potent and Selective β3 Adrenergic Receptor Agonist for the Treatment of Overactive Bladder. J Med Chem. Jan. 28, 2016;59(2):609-23.

Elayan et al., Chronic beta2 adrenergic agonist, but not exercise, improves glucose handling in older type 2 diabetic mice. Cell Mol Neurobiol. Jul. 2012;32(5):871-7.

Engelhardt, Structure activity relationship in a series of new amino-halogen substituted phenyl-aminoethanols. Arzneimittelforschung. May 1972;22(5):869-76.

Evans et al., beta2-Adrenoceptor-mediated regulation of glucose uptake in skeletal muscle-ligand-directed signalling or a reflection of system complexity? Naunyn Schmiedebergs Arch Pharmacol. Sep. 2013;386(9):757-60.

Evron et al., GRK2: multiple roles beyond G protein-coupled receptor desensitization. Trends Pharmacol Sci. Mar. 2012;33(3):154-64.

Exton, Mechanisms of hormonal regulation of hepatic glucose metabolism. Diabetes Metab Rev. Jan. 1987;3(1):163-83.

Feldman et al., Active-Site Inhibitors of mTOR Target Rapamycin-Resistant Outputs of mTORC1 and mTORC2. PLoS Biol. Feb. 10, 2009;7(2):e38. 13 pages.

Fisher et al., BMS-187257, a Potent, Selective, and Novel Heterocyclic beta3 Adrenergic Receptor Agonist. Bioorganic & Medicinal Chemistry Letters. 1996;6(19):2253-8.

Garcia-Martinez et al., Ku-0063794 is a specific inhibitor of the mammalian target of rapamycin (mTOR). Biochem J. Jun. 12, 2009;421(1):29-42.

Gaster et al., GLUT4 is reduced in slow muscle fibers of type 2 diabetic patients: is insulin resistance in type 2 diabetes a slow, type 1 fiber disease? Diabetes. Jun. 2001;50(6):1324-9.

Gavai et al., BMS-196085: a potent and selective full agonist of the human beta(3) adrenergic receptor. Bioorg Med Chem Lett. Dec. 3, 2001;11(23):3041-4.

Gawlik et al., Targeted disruption of Slc2a8 (GLUT8) reduces motility and mitochondrial potential of spermatozoa. Mol Membr Biol. Apr. 2008;25(3):224-35.

Gilman, G proteins: transducers of receptor-generated signals. Annu Rev Biochem. 1987;56:615-49.

Green et al., Use of Akt inhibitor and a drug-resistant mutant validates a critical role for protein kinase B/Akt in the insulin-dependent regulation of glucose and system A amino acid uptake. J Biol Chem. Oct. 10, 2008;283(41):27653-67.

Greife et al., Effects of the phenethanolamine clenbuterol on protein and lipid metabolism in growing rats. J Anim Physiol a Anim Nutr. 1989;61:19-27.

Gusovsky, Measurement of second messengers in signal transduction: cAMP and inositol phosphates. Curr Protoc Neurosci. May 2001;Chapter 7:Unit7.12.

Harrison et al., Activation of cell surface glucose transporters measured by photoaffinity labeling of insulin-sensitive 3T3-L1 adipocytes. J Biol Chem. Feb. 25, 1992;267(6):3783-8.

Harrison et al., Suppressed intrinsic catalytic activity of GLUT1 glucose transporters in insulin-sensitive 3T3-L1 adipocytes. Proc Natl Acad Sci U S A. Sep. 1, 1991;88(17):7839-43.

Hawkins et al., Signalling through Class I PI3Ks in mammalian cells. Biochem Soc Trans. Nov. 2006;34(Pt 5):647-62.

Hebert et al., Direct evidence for ATP modulation of sugar transport in human erythrocyte ghosts. J Biol Chem. Aug. 5, 1986;261(22):10093-9.

Hresko et al., mTOR.RICTOR is the Ser473 kinase for Akt/protein kinase B in 3T3-L1 adipocytes. J Biol Chem. Dec. 9, 2005;280(49):40406-16.

Huang et al., The GLUT4 glucose transporter. Cell Metab. Apr. 2007;5(4):237-52.

Huang, An in vitro assay for the kinase activity of mTOR complex 2. Methods Mol Biol. 2012;821:75-86.

Hutchinson et al., Agonist effects of zinterol at the mouse and human beta(3)-adrenoceptor. Naunyn Schmiedebergs Arch Pharmacol. May 2006;373(2):158-68.

Hutchinson et al., alpha1A-adrenoceptors activate glucose uptake in L6 muscle cells through a phospholipase C-, phosphatidylinositol-3 kinase-, and atypical protein kinase C-dependent pathway. Endocrinology. Feb. 2005;146(2):901-12.

(56) References Cited

OTHER PUBLICATIONS

Hutchinson et al., AMP-activated protein kinase activation by adrenoceptors in L6 skeletal muscle cells: mediation by alpha1-adrenoceptors causing glucose uptake. Diabetes. Mar. 2006;55(3):682-90.

Inokuma et al., Uncoupling protein 1 is necessary for norepinephrine-induced glucose utilization in brown adipose tissue. Diabetes. May 2005;54(5):1385-91.

Jones et al., G protein-coupled receptor kinases 2 and 5 are differentially expressed in rat skeletal muscle and remain unchanged following beta2-agonist administration. Exp Physiol. Mar. 2003;88(2):277-84.

Jozwiak et al., Comparative molecular field analysis of the binding of the stereoisomers of fenoterol and fenoterol derivatives to the beta2 adrenergic receptor. J Med Chem. Jun. 2007;50(12):2903-15.

Kaiser et al., Adrenergic agents. 1. Synthesis and potential beta-adrenergic agonist activity of some catecholamine analogs bearing a substituted amino functionality in the meta position. J Med Chem. Jan. 1974;17(1):49-57.

Kleiman et al., Developmentally spliced PKCbetaII provides a possible link between mTORC2 and Akt kinase to regulate 3T3-L1 adipocyte insulin-stimulated glucose transport. Biochem Biophys Res Commun. Oct. 23, 2009;388(3):554-9.

Koshy et al., Quantitative Measurement of GLUT4 Translocation to the Plasma Membrane by Flow Cytometry. Jove, J Vis Exp, www.jove.com. 3 pages, (2010).

Kovala et al., Protein kinase A regulation of cAMP phosphodiesterase expression in rat skeletal myoblasts. J Biol Chem. Mar. 25, 1994;269(12):8680-5.

Kumar et al., Fat cell-specific ablation of rictor in mice impairs insulin-regulated fat cell and whole-body glucose and lipid metabolism. Diabetes. Jun. 2010;59(6):1397-406.

Lacey et al., Selective stimulation of glucagon secretion by beta 2-adrenoceptors in isolated islets of Langerhans of the rat. Br J Pharmacol. Jul. 1991;103(3):1824-8.

Lamming et al., A Central role for mTOR in lipid homeostasis. Cell Metab. Oct. 1, 2013;18(4):465-9.

Laplante et al., mTOR signaling in growth control and disease. Cell. Apr. 13, 2012;149(2):274-93.

Largis et al., Antidiabetic and antiobesity effects of a highly selective β3-adrenoceptor agonist (CL 316,243). Drug Development Research. Jun. 1994;32(2):69-76.

Lawrence et al., GLUT4 facilitates insulin stimulation and cAMP-mediated inhibition of glucose transport. Proc Natl Acad Sci U S A. Apr. 15, 1992;89(8):3493-7.

Lidell et al., Evidence for two types of brown adipose tissue in humans. Nat Med. May 2013;19(5):631-4.

Liggett et al., Characterization of beta-adrenergic receptors of human skeletal muscle obtained by needle biopsy. Am J Physiol. 1988;254:E795-8.

Liu et al., Biphasic effects of the beta-adrenoceptor agonist, BRL 37344, on glucose utilization in rat isolated skeletal muscle. Br J Pharmacol. Mar. 1996;117(6):1355-61.

Liu et al., Chronic norepinephrine infusion stimulates glucose uptake in white and brown adipose tissues. Am J Physiol. 1994;266:914-20.

Macaulay et al., Isoproterenol inhibits cyclic AMP-mediated but not insulin-mediated translocation of the GLUT4 glucose transporter isoform. Mol Cell Biochem. Dec. 7, 1994;141(1):27-33.

Macheda et al., Molecular and cellular regulation of glucose transporter (GLUT) proteins in cancer. J Cell Physiol. Mar. 2005;202(3):654-62.

Marette et al., Stimulation of glucose transport by insulin and norepinephrine in isolated rat brown adipocytes. Am J Physiol. Oct. 1989;257(4 Pt 1):C714-21.

Mathvink et al., Potent, selective 3-pyridylethanolamine beta3 adrenergic receptor agonists possessing a thiazole benzenesulfonamide pharmacophore. Bioorg Med Chem Lett. Sep. 4, 2000;10(17):1971-3.

Mills et al., Beta-blockers and glucose control. Drug Intell Clin Pharm. Apr. 1985;19(4):246-51.

Murata et al., Indinavir inhibits the glucose transporter isoform Glut4 at physiologic concentrations. AIDS. Apr. 12, 2002;16(6):859-63.

Nave et al., Mammalian target of rapamycin is a direct target for protein kinase B: identification of a convergence point for opposing effects of insulin and amino-acid deficiency on protein translation. Biochem J. Dec. 1, 1999;344 Pt 2:427-31.

Nedergaard et al., New powers of brown fat: fighting the metabolic syndrome. Cell Metab. Mar. 2, 2011;13(3):238-40.

Nedergaard et al., PPARgamma in the control of brown adipocyte differentiation. Biochim Biophys Acta. May 30, 2005;1740(2):293-304.

Nedergaard et al., Three years with adult human brown adipose tissue. Ann N.Y. Acad Sci. 2011;1212:E20-E36.

Nedergaard et al., Unexpected evidence for active brown adipose tissue in adult humans. Am J Physiol Endocrinol Metab. 2007;293:E444-E452.

Neve et al., Turnover of beta 1- and beta 2-adrenergic receptors after down-regulation or irreversible blockade. Mol Pharmacol. Aug. 1986;30(2):104-11.

Nevzorova et al., Characterization of the beta-adrenoceptor subtype involved in mediation of glucose transport in L6 cells. Br J Pharmacol. Sep. 2002;137(1):9-18.

Nevzorova et al., Multiple signalling pathways involved in beta2-adrenoceptor-mediated glucose uptake in rat skeletal muscle cells. Br J Pharmacol. Feb. 2006;147(4):446-54.

Ngala et al., beta2-adrenoceptor agonists can both stimulate and inhibit glucose uptake in mouse soleus muscle through ligand-directed signalling. Naunyn Schmiedebergs Arch Pharmacol. Sep. 2013;386(9):761-73.

Ngala et al., Beta2-adrenoceptors and non-beta-adrenoceptors mediate effects of BRL37344 and clenbuterol on glucose uptake in soleus muscle: studies using knockout mice. Br J Pharmacol. Dec. 2009;158(7):1676-82.

Ngala et al., Metabolic responses to BRL37344 and clenbuterol in soleus muscle and C2C12 cells via different atypical pharmacologies and beta2-adrenoceptor mechanisms. Br J Pharmacol. Oct. 2008;155(3):395-406.

Ning et al., A new, one-step synthesis of 1-heteroaryl-2-alkylaminoethanols. Tetrahedron Letters. 2010;51:843-845.

Nobles et al., Distinct phosphorylation sites on the beta(2)-adrenergic receptor establish a barcode that encodes differential functions of beta-arrestin. Sci Signal. Aug. 9, 2011;4(185):ra51.

Nugent et al., Potentiation of glucose uptake in 3T3-L1 adipocytes by PPAR gamma agonists is maintained in cells expressing a PPAR gamma dominant-negative mutant: evidence for selectivity in the downstream responses to PPAR gamma activation. Mol Endocrinol. Oct. 2001;15(10):1729-38.

Palmada et al., SGK1 kinase upregulates GLUT1 activity and plasma membrane expression. Diabetes. Feb. 2006;55(2):421-7.

Pan et al., Effects of clenbuterol on insulin resistance in conscious obese Zucker rats. Am J Physiol Endocrinol Metab. Apr. 2001;280(4):E554-61.

Parmee et al., Discovery of L-755,507: a subnanomolar human beta 3 adrenergic receptor agonist. Bioorg Med Chem Lett. May 5, 1998;8(9):1107-12.

Phung et al., Pathological angiogenesis is induced by sustained Akt signaling and inhibited by rapamycin. Cancer Cell. Aug. 2006;10(2):159-70.

Plazinska et al., Molecular interactions between fenoterol stereoisomers and derivatives and the beta2-adrenergic receptor binding site studied by docking and molecular dynamics simulations. J Mol Model. Nov. 2013;19(11):4919-30.

Ploug et al., Kinetics of glucose transport in rat muscle: effects of insulin and contractions. Am J Physiol. 1987;253:12-20.

Polak et al., Adipose-specific knockout of raptor results in lean mice with enhanced mitochondrial respiration. Cell Metab. Nov. 2008;8(5):399-410.

(56) References Cited

OTHER PUBLICATIONS

PubChem CID: CID=4225365, 2-(Cyclohexylmethylamino)-1-phenylethanol, 2-[(cyclohexylmethyl)amino]-1-phenylethanol; 2-(cyclohexylmethylamino)-1-phen HMS1755E04, 1 page, Dec. 1, 2018.
PubChem CID: CID=83307546, SCHEMBL19329935; AKOS023017379. 4-[2-(Cyclohexylmethylamino)-1-hydroxyethyl]phenol. Dec. 12, 2001.
Pubchem, Compound CID: 60051619, SCHEMBL19329904, 1 page, Aug. 20, 2012.
Pubchem, Compound CID: 89173082, SCHEMBL13799302, 1 page, Feb. 13, 2015.
Rao et al., Synthesis, antimicrobial and molecular docking studies of enantiomerically pure N-alkylated beta-amino alcohols from phenylpropanolamines. Bioorg Med Chem Lett. Jul. 2014;24(14):3057-63.
Reinicke et al., Cellular distribution of Glut-1 and Glut-5 in benign and malignant human prostate tissue. J Cell Biochem. Feb. 2012;113(2):553-62.
Rodnick et al., Interaction of insulin and exercise on glucose transport in muscle. Diabetes Care. Nov. 1992;15(11):1679-89.
Rovira et al., mTOR Inhibition: Reduced Insulin Secretion and Sensitivity in a Rat Model of Metabolic Syndrome. Transplant Direct. Jan. 22, 2016;2(2):e65, 9 pages.
Rowland et al., Mapping insulin/GLUT4 circuitry. Traffic. Jun. 2011;12(6):672-81.
Rydzewski, Real World Drug Discovery, a Chemist's Guide to Biotech and Pharmaceutical Research. Elsevier, Amsterdam. pp. 42-43, (2008).
Salvador et al., Inhibition by butoxamine, propranolol and MJ1999 of the glycogenolytic action of the catecholamines in the rat. Biochem Pharmacol. Oct. 1967;16(10):2037-41.
Santulli et al., Pinpointing beta adrenergic receptor in ageing pathophysiology: victim or executioner? Evidence from crime scenes. Immun Ageing. Mar. 15, 2013;10(1):10.
Sarabia et al., Glucose uptake in human and animal muscle cells in culture. Biochem Cell Biol. Feb. 1990;68(2):536-42.
Sarbassov et al., Prolonged rapamycin treatment inhibits mTORC2 assembly and Akt/PKB. Mol Cell. Apr. 21, 2006;22(2):159-68.
Sarbassov et al., Rictor, a novel binding partner of mTOR, defines a rapamycin-insensitive and raptor-independent pathway that regulates the cytoskeleton. Curr Biol. Jul. 27, 2004;14(14):1296-302.
Sekulic et al., A direct linkage between the phosphoinositide 3-kinase-AKT signaling pathway and the mammalian target of rapamycin in mitogen-stimulated and transformed cells. Cancer Res. Jul. 1, 2000;60(13):3504-13.
Sennitt et al., The contribution of classical (beta1/2-) and atypical beta-adrenoceptors to the stimulation of human white adipocyte lipolysis and right atrial appendage contraction by novel beta3-adrenoceptor agonists of differing selectivities. J Pharmacol Exp Ther. Jun. 1998;285(3):1084-95.
Shah et al., The role of glucose transporters in brain disease: diabetes and Alzheimer's Disease. Int J Mol Sci. Oct. 3, 2012;13(10):12629-55.
Shan et al., Effects of GLUT4 expression on insulin resistance in patients with advanced liver cirrhosis. J Zhejiang Univ Sci B. Aug. 2011;12(8):677-82.
Shenoy et al., G-Protein Coupled Receptor—A Potential New Drug Target to Combat Diabetic Syndrome: An Overview. IJPSR. 2011;2(10):2490-2500.
Shibata et al., Cold exposure reverses inhibitory effects of fasting on peripheral glucose uptake in rats. Am J Physiol. Jul. 1989;257(1 Pt 2):R96-101.
Shimizu et al., Activation of brown adipose tissue thermogenesis in recovery from anesthetic hypothermia in rats. Am J Physiol. Aug. 1991;261(2 Pt 2):R301-4.
Simpson et al., The facilitative glucose transporter GLUT3: 20 years of distinction. Am J Physiol Endocrinol Metab. 2008;295:E242-E253.
Sobel et al., Abolition of crypticity of Arthrobacter pyridinolis toward glucose and alpha-glucosides by tricarboxylic acid cycle intermediates. J Bacteriol. Oct. 1973;116(1):271-8.
Spiller et al., A descriptive study of adverse events from clenbuterol misuse and abuse for weight loss and bodybuilding. Subst Abus. 2013;34(3):306-12.
Sprenger et al., Biophysical techniques for detection of cAMP and cGMP in living cells. Int J Mol Sci. Apr. 12, 2013;14(4):8025-46.
Stanford et al., Brown adipose tissue regulates glucose homeostasis and insulin sensitivity. J Clin Invest. Jan. 2013;123(1):215-23.
Taha et al., The insulin-dependent biosynthesis of GLUT1 and GLUT3 glucose transporters in L6 muscle cells is mediated by distinct pathways. Roles of p21ras and pp70 S6 kinase. J Biol Chem. Oct. 20, 1995;270(42):24678-81.
Tanis et al., Solvent and in situ catalyst preparation impacts upon Noyori reductions of aryl-chloromethyl ketones: application to syntheses of chiral 2-amino-1-aryl-ethanols. Tetrahedron: Asymmetry. Aug. 28, 2006;17(14):2154-82.
Tanis et al., The design and development of 2-aryl-2-hydroxy ethylamine substituted 1H,7H-pyrido[1,2,3-de]quinoxaline-6-carboxamides as inhibitors of human cytomegalovirus polymerase. Bioorg Med Chem Lett. Mar. 15, 2010;20(6):1994-2000.
Taverna et al., Reversible association of cytochalasin B with the human erythrocyte membrane. Inhibition of glucose transport and the stoichiometry of cytochalasin binding. Biochim Biophys Acta. Oct. 11, 1973;323(2):207-19.
Thong et al., Turning signals on and off: GLUT4 traffic in the insulin-signaling highway. Physiology (Bethesda). Aug. 2005;20:271-84.
Torgan et al., Exercise training and clenbuterol reduce insulin resistance of obese Zucker rats. Am J Physiol. Mar. 1993;264(3 Pt 1):E373-9.
Tritos et al., Clinical review 97: Syndromes of severe insulin resistance. J Clin Endocrinol Metab. Sep. 1998;83(9):3025-30.
Unger, Die Wirkung von butedrin auf den Blutzucker. The Effect of Butedrine on Blood Sugar. Zschr Inn Med. Jour Inn Med. Apr. 8, 1961;16(17):742-745.
Vardanega-Peicher et al., Time sequence of changes in the responsiveness of glycogen breakdown to adrenergic agonists in perfused liver of rats with insulin-induced hypoglycemia. Braz J Med Biol Res. Jul. 2000;33(7):805-13.
Violin et al., G-protein-coupled receptor kinase specificity for beta-arrestin recruitment to the beta2-adrenergic receptor revealed by fluorescence resonance energy transfer. J Biol Chem. Jul. 21, 2006;281(29):20577-88.
Watson-Wright et al., The Muscle Slice—A New Preparation for the Characterization of beta-Adrenergic Binding in Fast- and Slow-twitch Skeletal Muscle. Muscle & Nerve.1986;9:416-22.
Woo et al., Stereochemistry of an agonist determines coupling preference of beta2-adrenoceptor to different G proteins in cardiomyocytes. Mol Pharmacol. Jan. 2009;75(1):158-65.
Yamamoto et al., Beta(2)-Adrenergic activation increases glycogen synthesis in L6 skeletal muscle cells through a signalling pathway independent of cyclic AMP. Diabetologia. Jan. 2007;50(1):158-67.
Zeng et al., Rapamycin derivatives reduce mTORC2 signaling and inhibit AKT activation in AML. Blood. Apr. 15, 2007;109(8):3509-12.
Zhu et al., Discovery of benzamides as potent human β3 adrenergic receptor agonists. Bioorg Med Chem Lett. Jan. 1, 2016;26(1):55-9.
Ziegler et al., Endogenous epinephrine protects against obesity induced insulin resistance. Auton Neurosci. Jul. 5, 2011;162(1-2):32-4.
Ziegler et al., Epinephrine and the metabolic syndrome. Curr Hypertens Rep. Feb. 2012;14(1):1-7.
Zierath, In vitro studies of human skeletal muscle: hormonal and metabolic regulation of glucose transport. Acta Physiol Scand Suppl. 1995;626:1-96.
Zinzalla et al., Activation of mTORC2 by association with the ribosome. Cell. Mar. 4, 2011;144(5):757-68.
International Search Report and Written Opinion for Application No. PCT/GB2018/052593, dated Nov. 6, 2018, 11 pages.
U.S. Appl. No. 16/908,312, filed Jun. 22, 2020, 2020-0315993, Published.

(56) References Cited

OTHER PUBLICATIONS

Chen et al., Syntheses of 2,5- and 2,6-difluoronorepinephrine, 2,5-difluoraepinephrine, and 2,6-difluorophenylephrine: effect of disubstitution with fluorine on adrenergic activity. J Med Chem. Nov. 26, 1993;36(24):3947-55.
Lu et al., Syntheses of (R)- and (S)-2- and 6-fluoronorepinephrine and (R)- and (S)-2- and 6-fluoroepinephrine: effect of stereochemistry on fluorine-induced adrenergic selectivities. J Med Chem. Apr. 20, 2000;43(8):1611-9.
Luthy et al., Lead-oriented synthesis: Investigation of organolithium-mediated routes to 3-D scaffolds and 3-D shape analysis of a virtual lead-like library. Bioorg Med Chem. Jun. 1, 2015;23(11):2680-94.
Mathvink et al., Discovery of a potent, orally bioavailable beta(3) adrenergic receptor agonist, (R)-N-[4-[2-[[2-hydroxy-2-(3-pyridinyl)ethyl]amino]ethyl]phenyl]-4-[4-[4-(trifluoromethyl)phenyl]thiazol-2-yl]benzenesulfonamide. J Med Chem. Oct. 19, 2000;43(21):3832-6.
McCarty et al., Central Stimulants. a,a-Disubstituted 2-Piperidinemethanols and 1,1-Disubstituted Heptahydroöxazolo [3,4-a]pyridines. J Am Chem Soc. 1957;79:472-480.
Sanner, Stereoselective condensations of a'-lithio pyrrolidine amidines. Tetrahedron Letters. 1989;30(15):1909-1912.
Ye et al., Dual catalysis for enantioselective convergent synthesis of enantiopure vicinal amino alcohols. Nat Commun. Jan. 29, 2018;9(1):410, 9 pages.
Ye et al., One-Pot Cascade Hydration-Asymmetric Transfer Hydrogenation as a Practical Strategy to Construct Chiral beta-Adrenergic Receptor Blockers. ChemCatChem. Jun. 15, 2015;7(12):1801-1805.
Lands, The Effect on Blood Pressure and Toxicity of 1-{3-Fluorophenyl)-2-Aminoethanol and Related Compounds. Journal of Pharmacology and Experimental Therapeutics. Dec. 1, 1952;106(4):440-443.
CAS RN 2155248-91-0. Chemcats entry date: Jan. 15, 2019. 1 page.
CAS RN 2274711-69-0. Chemcats entry date: Jan. 15, 2019. 1 page.
CAS RN 2278127-42-5. Chemcats entry date: Jan. 15, 2019. 1 page.
CAS RN 2287791-82-4. Chemcats entry date: Jan. 15, 2019. 1 page.
CAS RN 2289315-62-2. Chemcats entry date: Jan. 15, 2019. 1 page.
U.S. Appl. No. 15/324,580, filed Jan. 6, 2017, 2017-0153225, Abandoned.
U.S. Appl. No. 16/082,750, filed Sep. 6, 2018, 2019-0119196, Published.
U.S. Appl. No. 16/317,009, filed Jan. 10, 2019, 2019-0314301, Abandoned.
U.S. Appl. No. 16/908,312, filed Jun. 22, 2020, 2020-0315993, Abandoned.
U.S. Appl. No. 17/320,774, filed May 14, 2021, Pending.
U.S. Appl. No. 16/646,497, filed Mar. 11, 2020, 2020-0268688, Published.
U.S. Appl. No. 16/646,492, filed Mar. 11, 2020, 2020-0268687, Published.
U.S. Appl. No. 16/645,286, filed Mar. 6, 2020, 2021-0030731, Published.
U.S. Appl. No. 17/439,668, filed Sep. 15, 2021, Pending.
Ashmore et al., Effects of Dichloroisoproterenol on Blood Sugar and Plasma Free Fatty Acids. Proceedings of the Society for Experimental Biology and Medicine. 1962;109:291-294.
Chait et al., Diabetes and atherosclerosis: is there a role for hyperglycemia? J Lipid Res. Apr. 2009;50 Suppl(Suppl):S335-9.
U.S. Appl. No. 14/759,572, filed Jul. 7, 2015, U.S. Pat. No. 9,784,726 Issued.
U.S. Appl. No. 15/727,851, filed Oct. 9, 2017, U.S. Pat. No. 10,288,602, Issued.
U.S. Appl. No. 14/759,747, filed Apr. 8, 2015, U.S. Pat. No. 9,657,348, Issued.
U.S. Appl. No. 15/104,830, filed Jun. 15, 2016, U.S. Pat. No. 9,891,212, Issued.
U.S. Appl. No. 15/324,580, filed Jan. 6, 2017, Publication No. 2017-0153225, Abandoned.
U.S. Appl. No. 16/082,750, filed Sep. 6, 2018, Publication No. 2019-0119196, Published.
U.S. Appl. No. 16/317,009, filed Jan. 10, 2019, Publication No. 2019-0314301, Abandoned.
U.S. Appl. No. 16/908,312, filed Jun. 22, 2020, Publication No. 2020-0315993, Abandoned.
U.S. Appl. No. 17/320,774, filed May 14, 2021, Publication No. 2021-0338603, Published.
U.S. Appl. No. 16/646,497, filed Mar. 11, 2020, Publication No. 2020-0268688, Published.
U.S. Appl. No. 16/646,492, filed Mar. 11, 2020, Publication No. 2020-0268687, Published.
U.S. Appl. No. 16/645,286, filed Mar. 6, 2020, U.S. Pat. No. 11,357,757, Issued.
U.S. Appl. No. 17/575,175, filed Jan. 13, 2022, Publication No. 2022-0133703, Published.
U.S. Appl. No. 17/439,638, filed Sep. 15, 2021, Pending.
U.S. Appl. No. 17/439,668, filed Sep. 15, 2021, Publication No. 2022-0150004, Published.

* cited by examiner

BETA-HYDROXY HETEROCYCLIC AMINES AND THEIR USE IN THE TREATMENT OF HYPERGLYCAEMIA

CROSS-REFERENCE TO RELATED APPLICATIONS

This application is a U.S. national stage filing, under 35 U.S.C. § 371(c), of International Application No. PCT/GB2018/052593, filed on Sep. 13, 2018, which claims priority to United Kingdom Patent Application No. 1714740.6, filed on Sep. 13, 2017.

FIELD OF THE INVENTION

The present invention relates to novel compounds and compositions, and their use in the treatment of hyperglycaemia and disorders characterised by hyperglycaemia, such as type 2 diabetes. In particular, the invention relates to novel compounds, compositions and methods for the treatment of conditions such as type 2 diabetes through activation of the $\beta_2$-adrenergic receptor. Importantly, such compounds are thought to have a beneficial side-effect profile as they do not exert their effect through significant cAMP release.

BACKGROUND OF THE INVENTION

The listing or discussion of an apparently prior-published document in this specification should not necessarily be taken as an acknowledgement that the document is part of the state of the art or is common general knowledge.

Hyperglycaemia, or high blood sugar is a condition in which an excessive amount of glucose circulates in the blood plasma. If not treated, hyperglycaemia can be a serious problem, potentially developing into life-threatening conditions such as ketoacidosis. For example, chronic hyperglycemia may cause injury to the heart, and is strongly associated with heart attacks and death in subjects with no coronary heart disease or history of heart failure. There are various causes of hyperglycaemia, including diabetes and severe insulin resistance.

Severe insulin resistance (SIR) is a condition wherein the patent experiences very low levels of (or, in extreme cases, no significant) response to insulin. There are several syndromes characterized by SIR, including Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndrome, pseudoacromegaly, and lipodystrophy. The majority of these conditions have genetic causes, such as mutations in the insulin receptor gene. The prevalence for Donohue's syndrome, Rabson-Mendenhall syndrome and Type A syndrome of insulin resistance, has been reported to vary from about 50 reported cases to 1 in 100,000. However, since some diseases are severe and extremely rare, it is likely that many patients do not get diagnosed before they die, particularly in less developed areas of the world. Thus, the exact number of patients with these syndromes is difficult to assess.

The current standard for hyperglycaemia treatment in patients having SIR is a controlled diet, supplemented with drugs affecting insulin receptor sensitivity, such as metformin, or insulin supplement. However, particularly for disorders caused by mutations in the insulin receptor gene, this treatment is not sufficiently effective and ultimately proves unsuccessful.

Diabetes comprises two distinct diseases, type 1 (or insulin-dependent diabetes) and type 2 (insulin-independent diabetes), both of which involve the malfunction of glucose homeostasis. Type 2 diabetes affects more than 400 million people in the world and the number is rising rapidly. Complications of type 2 diabetes include severe cardiovascular problems, kidney failure, peripheral neuropathy, blindness and, in the later stages of the disease, even loss of limbs and, ultimately death. Type 2 diabetes is characterized by insulin resistance in skeletal muscle and adipose tissue, and there is presently no definitive cure. Most treatments used today are focused on remedying dysfunctional insulin signalling or inhibiting glucose output from the liver but many of those treatments have several drawbacks and side effects. There is thus a great interest in identifying novel insulin-independent ways to treat type 2 diabetes.

In type 2 diabetes, the insulin-signalling pathway is blunted in peripheral tissues such as adipose tissue and skeletal muscle. Methods for treating type 2 diabetes typically include lifestyle changes, as well as insulin injections or oral medications to regulate glucose homeostasis. People with type 2 diabetes in the later stages of the disease develop 'beta-cell failure' i.e. the inability of the pancreas to release insulin in response to high blood glucose levels. In the later stages of the disease patients often require insulin injections in combination with oral medications to manage their diabetes. Further, most common drugs have side effects including downregulation or desensitization of the insulin pathway and/or the promotion of lipid incorporation in adipose tissue, liver and skeletal muscle. There is thus a great interest in identifying novel ways to treat metabolic diseases including type 2 diabetes that do not include these side effects.

Following a meal, increased blood glucose levels stimulate insulin release from the pancreas. Insulin mediates normalization of the blood glucose levels. Important effects of insulin on glucose metabolism include facilitation of glucose uptake into skeletal muscle and adipocytes, and an increase of glycogen storage in the liver. Skeletal muscle and adipocytes are responsible for insulin-mediated glucose uptake and utilization in the fed state, making them very important sites for glucose metabolism.

The signalling pathway downstream from the insulin receptor has been difficult to understand in detail. In brief, control of glucose uptake by insulin involves activation of the insulin receptor (IR), the insulin receptor substrate (IRS), the phosphoinositide 3-kinase (PI3K) and thus stimulation of phosphatidylinositol (3,4,5)-triphosphate (PIP3), the mammalian target of rapamycin (also called the mechanistic target of rapamycin, mTOR), Akt/PKB (Akt) and TBC1D4 (AS160), leading to translocation of the glucose transporter 4 (GLUT4) to the plasma membrane. Akt activation is considered necessary for GLUT4 translocation.

It should be noted that skeletal muscles constitute a major part of the body weight of mammals and have a vital role in the regulation of systemic glucose metabolism, being responsible for up to 85% of whole-body glucose disposal. Glucose uptake in skeletal muscles is regulated by several intra- and extracellular signals. Insulin is the most well studied mediator but others also exist. For example, AMP activated kinase (AMPK) functions as an energy sensor in the cell, which can increase glucose uptake and fatty acid oxidation. Due to the great influence skeletal muscles have on glucose homeostasis it is plausible that additional mechanisms exist. In the light of the increased prevalence of type 2 diabetes, it is of great interest to find and characterize novel insulin-independent mechanisms to increase glucose uptake in muscle cells.

Blood glucose levels may be regulated by both insulin and catecholamines, but they are released in the body in response to different stimuli. Whereas insulin is released in response to the rise in blood sugar levels (e.g. after a meal), epinephrine and norepinephrine are released in response to various internal and external stimuli, such as exercise, emotions and stress, and also for maintaining tissue homeostasis. Insulin is an anabolic hormone that stimulates many processes involved in growth including glucose uptake, glycogen and triglyceride formation, whereas catecholamines are mainly catabolic.

Although insulin and catecholamines normally have opposing effects, it has been shown that they have similar actions on glucose uptake in skeletal muscle (Nevzorova et al., *Br. J. Pharmacol*, 137, 9, (2002)). In particular, it has been reported that catecholamines stimulate glucose uptake via adrenergic receptors (Nevzorova et al., *Br. J. Pharmacol*, 147, 446, (2006); Hutchinson, Bengtsson Endocrinology 146, 901, (2005)) to supply muscle cells with an energy-rich substrate. Thus it is likely that in mammals, including humans, the adrenergic and the insulin systems can work independently to regulate the energy needs of skeletal muscle in different situations. Since insulin also stimulates many anabolic processes, including some that promote undesired effects such as stimulation of lipid incorporation into tissues, leading to e.g. obesity, it would be beneficial to be able to stimulate glucose uptake by other means; for example, by stimulation of the adrenergic receptors (ARs).

All ARs are G protein-coupled receptors (GPCRs) located in the cell membrane and characterized by an extracellular N-terminus, followed by seven transmembrane α-helices (TM-1 to TM-7) connected by three intracellular (IL-1 to IL-3) and three extracellular loops (EL-1 to EL-3), and finally an intracellular C-terminus. There are three different classes of ARs, with distinct expression patterns and pharmacological profiles: $\alpha_1$-, $\alpha_2$- and β-ARs. The $\alpha_1$-ARs comprise the $\alpha_{1A}$, $\alpha_{1B}$ and $\alpha_{1D}$ subtypes while $\alpha_2$-ARs are divided into $\alpha_{2A}$, $\alpha_{2B}$ and $\alpha_{2C}$. The β-ARs are also divided into the subtypes $\beta_1$, $\beta_2$, and $\beta_3$, of which $\beta_2$-AR is the major isoform in skeletal muscle cells. ARs are G protein coupled receptors (GPCRs) that signal through classical secondary messengers such as cyclic adenosine monophosphate (cAMP) and phospholipase C (PLC).

Many effects occurring downstream of ARs in skeletal muscles have been attributed to classical secondary messenger signalling, such as increase in cAMP levels, PLC activity and calcium levels. Stimulation involving the classical secondary messengers has many effects in different tissues. For example, it increases heart rate, blood flow, airflow in lungs and release of glucose from the liver, which all can be detrimental or be considered unwanted side effects if stimulation of ARs should be considered as a type 2 diabetes treatment. Adverse effects of classical AR agonists are, for example, tachycardia, palpitation, tremor, sweats, agitation and increased glucose levels in the blood (glucose output from the liver). It would thus be beneficial to be able to activate ARs without activating these classical secondary messengers, such as cAMP, to increase glucose uptake in peripheral tissues without stimulating the unwanted side effects.

Glucose uptake is mainly stimulated via facilitative glucose transporters (GLUT) that mediate glucose uptake into most cells. GLUTs are transporter proteins that mediate transport of glucose and/or fructose over the plasma membrane down the concentration gradient. There are fourteen known members of the GLUT family, named GLUT1-14, divided into three classes (Class I, Class II and Class III) dependent on their substrate specificity and tissue expression. GLUT1 and GLUT4 are the most intensively studied isoforms and, together with GLUT2 and GLUT3, belong to Class I which mainly transports glucose (in contrast to Class II that also transports fructose). GLUT1 is ubiquitously expressed and is responsible for basal glucose transport. GLUT4 is only expressed in peripheral tissues such as skeletal muscle, cardiac muscle and adipose tissues. GLUT4 has also been reported to be expressed in, for example, the brain, kidney, and liver. GLUT4 is the major isoform involved in insulin stimulated glucose uptake. The mechanism whereby insulin signalling increases glucose uptake is mainly via GLUT4 translocation from intracellular storage to the plasma membrane. It is known that GLUT4 translocation is induced by stimulation of the $\beta_2$-adrenergic receptor.

Thus, a possible treatment of a condition involving dysregulation of glucose homeostasis or glucose uptake in a mammal, such as type 2 diabetes, would involve the activation of the $\beta_2$-adrenergic receptor leading to GLUT4 translocation to the plasma membrane and promotion of glucose uptake into skeletal muscle leading to normalization of whole body glucose homeostasis. In addition, it would be advantageous if the treatment does not involve signalling through cAMP as this would lead to a favourable side-effect profile.

The vasodilator 4-(2-(butylamino)-1-hydroxyethyl)phenol, which has been used in the treatment of peripheral vascular disorders, has been found to initially increase blood sugar and has been contraindicated in diabetes and pre-diabetes (see Unger, H., *Zeitschrift für die Gesamte Innere Medizin and Ihre Grenzgebiete*, 16, 742 (1961)).

DESCRIPTION OF THE INVENTION

We have now surprisingly found that certain β-hydroxy heterocyclic amines acting as agonists at the $\beta_2$-adrenergic receptor increase glucose uptake in skeletal muscle.

In addition, we have found that this effect is not mediated through significant cAMP release, such that many of the commonly described side effects seen with traditional $\beta_2$-adrenergic agonists (e.g. tachycardia, palpitation, tremor, sweats, agitation, and the like) can be reduced.

The use of such compounds in medicine represents a promising strategy for the treatment of conditions characterized by high blood sugar levels (i.e. hyperglycaemia), such as type 2 diabetes.

Compounds of the Invention

In a first aspect of the invention, there is provided a compound of formula I

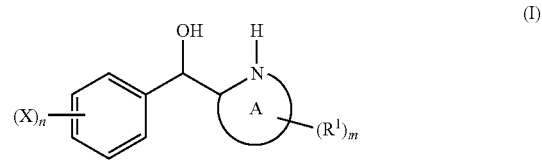

or a pharmaceutically acceptable salt thereof, wherein:
ring A represents a 4- to 8-membered heterocycloalkyl;
each $R^1$ independently represents $C_{1-6}$ alkyl optionally substituted by one or more halo;

each X independently represents halo, $R^a$, —CN, —N$_3$, —N(R$^b$)R$^c$, —NO$_2$, —ONO$_2$, —OR$^d$, —S(O)$_p$R$^e$ or —S(O)$_q$ N(R$^f$)R$^g$;

$R^a$ represents C$_{1-6}$ alkyl optionally substituted by one or more groups independently selected from G;

each R$^b$, R$^c$, R$^d$, R$^e$, R$^f$ and R$^g$ independently represents H or C$_{1-6}$ alkyl optionally substituted by one or more groups independently selected from G;

or alternatively any of R$^b$ and R$^c$ and/or R$^f$ and R$^g$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl optionally substituted by one or more halo, and =O;

G represents halo, —CN, —N(R$^{a1}$)R$^{b1}$, —OR$^{c1}$, —S(O)$_p$ R$^{d1}$, —S(O)$_q$N(R$^{e1}$)R$^{f1}$ or =O;

each R$^{a1}$, R$^{b1}$, R$^{c1}$, R$^{d1}$, R$^{e1}$ and R$^{f1}$ independently represents H or C$_{1-6}$ alkyl optionally substituted by one or more halo;

or alternatively any of R$^{a1}$ and R$^{b1}$ and/or R$^{e1}$ and R$^{f1}$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl optionally substituted by one or more halo, and =O;

m represents 0 to 9;
n represents 0 to 5;
each p independently represents 0, 1 or 2; and
each q independently represents 1 or 2, which compounds (including pharmaceutically acceptable salts) may be referred to herein as "compounds of the invention".

For the avoidance of doubt, the skilled person will understand that references herein to compounds of particular aspects of the invention (such as the first aspect of the invention, e.g. compounds of formula I) will include references to all embodiments and particular features thereof, which embodiments and particular features may be taken in combination to form further embodiments.

Unless indicated otherwise, all technical and scientific terms used herein have the same meaning as commonly understood by one of ordinary skill in the art to which this invention pertains.

Pharmaceutically acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

Particular acid addition salts that may be mentioned include carboxylate salts (e.g. formate, acetate, trifluoroacetate, propionate, isobutyrate, heptanoate, decanoate, caprate, caprylate, stearate, acrylate, caproate, propiolate, ascorbate, citrate, glucuronate, glutamate, glycolate, α-hydroxybutyrate, lactate, tartrate, phenylacetate, mandelate, phenylpropionate, phenylbutyrate, benzoate, chlorobenzoate, methylbenzoate, hydroxybenzoate, methoxybenzoate, dinitrobenzoate, o-acetoxy-benzoate, salicylate, nicotinate, isonicotinate, cinnamate, oxalate, malonate, succinate, suberate, sebacate, fumarate, malate, maleate, hydroxymaleate, hippurate, phthalate or terephthalate salts), halide salts (e.g. chloride, bromide or iodide salts), sulphonate salts (e.g. benzenesulphonate, methyl-, bromo- or chloro-benzenesulphonate, xylenesulphonate, methanesulphonate, ethanesulphonate, propanesulphonate, hydroxy-ethanesulphonate, 1- or 2-naphthalene-sulphonate or 1,5-naphthalenedisulphonate salts) or sulphate, pyrosulphate, bisulphate, sulphite, bisulphite, phosphate, monohydrogenphosphate, dihydrogenphosphate, metaphosphate, pyrophosphate or nitrate salts, and the like.

Particular base addition salts that may be mentioned include salts formed with alkali metals (such as Na and K salts), alkaline earth metals (such as Mg and Ca salts), organic bases (such as ethanolamine, diethanolamine, triethanolamine, tromethamine and lysine) and inorganic bases (such as ammonia and aluminium hydroxide). More particularly, base addition salts that may be mentioned include Mg, Ca and, most particularly, K and Na salts.

Particular pharmaceutically acceptable salts that may be mentioned include acetate salts.

Further pharmaceutically acceptable salts that may be mentioned include maleate and hydrochloride (HCl) salts.

For the avoidance of doubt, compounds of the first aspect of the invention may exist as solids, and thus the scope of the invention includes all amorphous, crystalline and part crystalline forms thereof, and may also exist as oils. Where compounds of the first aspect of the invention exist in crystalline and part crystalline forms, such forms may include solvates, which are included in the scope of the invention. Compounds of the first aspect of the invention may also exist in solution.

Compounds of the first aspect of the invention may contain double bonds and may thus exist as E (entgegen) and Z (zusammen) geometric isomers about each individual double bond. All such isomers and mixtures thereof are included within the scope of the invention.

Compounds of the first aspect of the invention may also exhibit tautomerism. All tautomeric forms and mixtures thereof are included within the scope of the invention.

Compounds of the first aspect of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers (i.e. enantiomers) may be isolated by separation of a racemic or other mixture of the compounds using conventional, e.g. fractional crystallisation or HPLC, techniques. Alternatively the desired optical isomers may be obtained from appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution); for example, with a homochiral acid followed by separation of the diastereomeric derivatives by conventional means such as chromatography, or by reaction with an appropriate chiral reagent or chiral catalyst all under conditions known to the skilled person. All stereoisomers and mixtures thereof are included within the scope of the invention.

As used herein, the term heterocycloalkyl may refer to non-aromatic, saturated and monocyclic groups wherein at least one atom comprised in the ring is a heteroatom (i.e. saturated heterocyclic groups). In particular, such groups may comprise from 1 to 4 heteroatoms, such as heteroatoms selected from O, S and N, which N may be present in secondary or tertiary degrees of substitution.

For the avoidance of doubt, ring A, as described in compounds of formula I, contains an essential nitrogen atom and an essential carbon atom, as represented in the 2-position of ring A (i.e. in the position alpha to both the essential nitrogen atom of the A ring and the carbon bearing the essential —OH group).

For the avoidance of doubt, ring A may be substituted by a number of $R^1$ groups, as defined herein, which number is defined by m, as defined herein. The skilled person will understand that the (maximum) number and position of such substituents will be dictated by the nature of the heterocyclic ring, such as by the size of the ring and the number and type of heteroatoms comprised therein. Thus, where m is defined as 0 to 9, it will be understood that the value 9 represents a theoretical maximum when considering the heterocyclic rings that may be present as ring A, and that for certain heterocyclic groups representing ring A the actual maximum value for m may be lower, as will be readily determined by the skilled person. Moreover, the skilled person will understand that such substituents may be present on suitable moieties comprised within ring A, such as C (carbon) moieties and secondary N (nitrogen) moieties.

In particular, ring A as defined herein may comprise one or two heteroatoms (including the essential NH moiety), which may be selected (in addition to the essential NH moiety) from O, S and N (e.g. O and N, such as N). Thus, in addition to the essential NH moiety, ring A as defined herein may comprise up to one additional heteroatom, which may be selected from O, S and N (e.g. O and N, such as N).

In particular, ring A as defined herein may be 4- to 6-membered. For example, ring A as defined herein may be 4- to 6-membered comprising one or two heteroatoms (i.e. up to one additional heteroatom), which may be selected from O, S and N (e.g. O and N, such as N).

More particularly, ring A as defined herein may be 5- or 6-membered. For example, ring A as defined herein may be 5- or 6-membered comprising one or two heteroatoms (i.e. up to one additional heteroatom), which may be selected from O, S and N (e.g. O and N, such as N).

Particular heterocycloalkyl groups that may be mentioned (e.g. in relation to ring A as defined for compounds of formula I, including all embodiments thereof) include azetidinyl (e.g. azetidine-2-yl, wherein position 1 is the N atom), pyrrolidinyl (e.g. pyrrolidine-2yl), piperidinyl (e.g. piperidin-2-yl) and azepanyl (e.g. azepan-2-yl). More particular heterocycloalkyl groups that may be mentioned include pyrrolidinyl (e.g. pyrrolidine-2-yl) and piperidinyl (e.g. piperidin-2-yl).

As used herein, references to halo and/or halogen groups will each independently refer to fluoro, chloro, bromo and iodo (for example, fluoro (F) and chloro (Cl), such as F).

Unless otherwise specified, $C_{1-z}$ alkyl groups (where z is the upper limit of the range) defined herein may be straight-chain or, when there is a sufficient number (i.e. a minimum of three) of carbon atoms, be branched-chain, and/or cyclic (so forming a $C_{3-z}$-cycloalkyl group). When there is a sufficient number (i.e. a minimum of four) of carbon atoms, such groups may also be part cyclic. Part cyclic alkyl groups that may be mentioned include cyclopropylmethyl and cyclohexylethyl. When there is a sufficient number of carbon atoms, such groups may also be multicyclic (e.g. bicyclic or tricyclic) or spirocyclic. Such alkyl groups may also be saturated or, when there is a sufficient number (i.e. a minimum of two) of carbon atoms, be unsaturated (forming, for example, a $C_{2-z}$ alkenyl or a $C_{2-z}$ alkynyl group). Particular alkyl groups that may be mentioned include saturated alkyl groups.

For the avoidance of doubt, as used herein, references to heteroatoms will take their normal meaning as understood by one skilled in the art. Particular heteroatoms that may be mentioned include phosphorus, selenium, tellurium, silicon, boron, oxygen, nitrogen and sulphur (e.g. oxygen, nitrogen and sulphur).

For the avoidance of doubt, references to polycyclic (e.g. bicyclic or tricyclic) groups (e.g. when employed in the context of cycloalkyl groups) will refer to ring systems wherein at least two scissions would be required to convert such rings into a straight chain, with the minimum number of such scissions corresponding to the number of rings defined (e.g. the term bicyclic may indicate that a minimum of two scissions would be required to convert the rings into a straight chain). For the avoidance of doubt, the term bicyclic (e.g. when employed in the context of alkyl groups) may refer to groups in which the second ring of a two-ring system is formed between two adjacent atoms of the first ring, and may also refer to groups in which two non-adjacent atoms are linked by an alkylene group, which later groups may be referred to as bridged.

The present invention also embraces isotopically-labelled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Hence, the compounds of the invention also include deuterated compounds, i.e. in which one or more hydrogen atoms are replaced by the hydrogen isotope deuterium.

For the avoidance of doubt, in cases in which the identity of two or more substituents in a compound of the invention may be the same, the actual identities of the respective substituents are not in any way interdependent. For example, in the situation in which two or more X groups are present, those X groups may be the same or different. Similarly, where two or more X groups are present and each represent halo, the halo groups in question may be the same or different. Likewise, when more than one $R^a$ is present and each independently represents $C_{1-6}$ alkyl substituted by one or more G group, the identities of each G are in no way interdependent.

The skilled person will appreciate that compounds of the invention that are the subject of this invention include those that are stable. That is, compounds of the invention include those that are sufficiently robust to survive isolation, e.g. from a reaction mixture, to a useful degree of purity.

All embodiments of the invention and particular features mentioned herein may be taken in isolation or in combination with any other embodiments and/or particular features mentioned herein (hence describing more particular embodiments and particular features as disclosed herein) without departing from the disclosure of the invention.

In certain embodiments of the first aspect of the invention, there is provided a compound of formula IA (i.e. the compound of formula I may be a compound of formula IA)

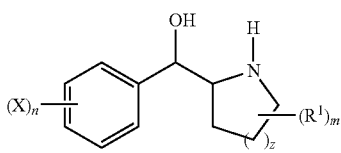

(IA)

or a pharmaceutically acceptable salt thereof, wherein:
$R^1$, X and n are as defined herein;
z represents 0 to 2; and wherein when z represents 0 then m represents 0 to 5, or when z represents 1 then m represents 0 to 7 or when z represents 2 then m represents 0 to 9.

For the avoidance of doubt, the skilled person will understand that:

when z represents 0 (i.e the ring containing the essential nitrogen atom is an azetidine ring), then m may be 0, 1, 2, 3, 4 or 5 (e.g. 0 or 1), such as 1, 2, 3, 4 or 5 (i.e. 1 to 5);

when z represents 1 (i.e the ring containing the essential nitrogen atom is a pyrrolidine ring), then m may be 0, 1, 2, 3, 4, 5, 6 or 7 (e.g. 0 or 1), such as 1, 2, 3, 4, 5, 6 or 7 (i.e. 1 to 7); and when z represents 2 (i.e the ring containing the essential nitrogen atom is a piperidine ring), then m may be 0, 1, 2, 3, 4, 5, 6, 7, 8 or 9 (e.g. 0 or 1), such as 1, 2, 3, 4, 5, 6, 7, 8 or 9 (i.e. 1 to 9).

In particular embodiments, z represents 1 or 2.
In certain embodiments, z represents 1.
In certain embodiments, z represents 2.
In certain embodiments, where the heteroaryl group representing ring A is a piperidine (i.e. where z represents 2):
ring A is not substituted in the 4-position; and/or
$R^1$ represents $C_{2-6}$ alkyl, particularly where m represents 1 to 9.

In certain embodiments, where the heteroaryl group representing ring A is a piperidine (i.e. where z represents 2), ring A is not substituted in the 4-position.

In other particular embodiments, $R^1$ represents $C_{1-6}$ alkyl optionally substituted by one or more F (e.g. two or three), such as $C_{1-3}$ alkyl optionally substituted by three F (e.g. where the three F are attached to the terminal carbon of the $C_{1-3}$ alkyl, e.g. 3,3,3-trifluoropropyl).

In more particular embodiments, $R^1$ represents $C_{1-6}$ alkyl, such as $C_{1-3}$ alkyl.

In certain embodiments, where z represents 2, $R^1$ represents at least $C_2$ alkyl, e.g. $C_{2-6}$ alkyl, such as $C_{2-3}$ alkyl.

In particular embodiments, $R^1$ represents $C_{1-6}$ alkyl (e.g. $C_{3-6}$ alkyl), particularly wherein the carbon bound to the ring containing the essential N atom is unbranched, e.g. represented by a —$CH_2$— moiety.

Particular $R^1$ groups that may be mentioned include those in which the alkyl group (for example, a $C_{1-6}$ alkyl group) is linear or part-cyclic (particularly, wherein the group is part-cyclic, such that the carbon bound to the ring containing the essential N atom is unbranched, e.g. —$CH_2$— moiety).

Other particular $R^1$ groups that may be mentioned include those in which the alkyl group (e.g. the $C_{1-6}$ alkyl) is linear (e.g. methyl, ethyl, n-propyl, n-butyl, n-pentyl or n-hexyl).

In certain embodiments, $R^1$ represents methyl, ethyl, n-propyl, isopropyl, n-butyl, sec-butyl, tert-butyl, 2-pentyl, cyclopentyl, —$CH_2$-cyclopropyl, n-hexyl or cyclohexyl.

In yet further embodiments of the first aspect of the invention, $R^1$ represents methyl, ethyl or n-propyl.

In particular embodiments that may be mentioned, where z represents 1, $R^1$ represents $C_{2-6}$ alkyl.

In more particular embodiments, $R^1$ represents $C_{2-6}$ alkyl, such as $C_{2-3}$ alkyl.

In yet more particular embodiments, $R^1$ represents $C_{2-6}$ alkyl (e.g. $C_{2-3}$ alkyl), particularly wherein the carbon bound to the ring containing the essential N atom is unbranched, e.g. represented by a —$CH_2$— moiety.

Particular $R^1$ groups that may be mentioned include those in which the alkyl group (for example, a $C_{2-6}$ alkyl group) is linear or part-cyclic (particularly, wherein the group is part-cyclic, such that the carbon bound to the ring containing the essential N atom is unbranched, e.g. —$CH_2$— moiety).

Other particular $R^1$ groups that may be mentioned include those in which the alkyl group (e.g. the $C_{2-6}$ alkyl) is linear (e.g. ethyl, n-propyl, n-butyl, n-pentyl or n-hexyl).

In certain embodiments, $R^1$ represents ethyl, n-propyl, isopropyl, n-butyl, sec-butyl, tert-butyl, 2-pentyl, cyclopentyl, —$CH_2$-cyclopropyl, n-hexyl or cyclohexyl.

In yet further embodiments of the first aspect of the invention, $R^1$ represents n-propyl.

In certain embodiments, $R^1$ does not represent tert-butyl.

The skilled person will understand that the prefixes "n-", "sec-" and "tert-" when applied to alkyl groups indicate the terms "normal", "secondary" and "tertiary". The term "normal" indicates a linear alkyl group where the point of attachment of the group to the rest of a molecule is through a carbon atom at the end of the carbon chain and thus that that carbon atom is bound to one other carbon atom. The term "secondary" indicates that the point of attachment of the rest of the molecule to the alkyl group is through a carbon atom adjacent to the end of the carbon chain and thus that that carbon is itself bound to two other carbon atoms. The term "tertiary" indicates that the point of attachment of the alkyl group to the rest of a molecule is through a carbon atom that is bound to three other carbon atoms.

In certain embodiments of the first aspect of the invention, there is provided the compound of formula IA wherein when z represents 0, m represents 0 to 4 (e.g. 1) and, where present, $R^1$ represents $C_{1-6}$ alkyl, (e.g. methyl, ethyl or n-propyl), such as $C_{2-6}$ alkyl (e.g. ethyl or n-propyl, particularly n-propyl). In such embodiments, $R^1$ may be located in the 3- or 4-positions of the ring containing the essential nitrogen atom (with the point of attachment to the essential hydroxyl benzyl moiety being the 2-position). In particular embodiments, the $R^1$ may be in the 4-position of the ring containing the essential nitrogen atom.

In alternative embodiments of the first aspect of the invention, there is provided a compound of formula IA wherein when z represents 1, m represents 0 to 6 (e.g. 1) and $R^1$ represents $C_{1-6}$ alkyl (e.g. methyl, ethyl or n-propyl, such as ethyl or n-propyl, particularly n-propyl), such as $C_{2-6}$ alkyl (e.g. ethyl or n-propyl). In such embodiments, $R^1$ may be located in the 3-, 4- or 5-positions of the ring containing the essential nitrogen atom. In particular embodiments, the $R^1$ may be in the 5-position of the ring containing the essential nitrogen atom (with the point of attachment to the essential hydroxyl benzyl moiety being the 2-position).

In further alternative embodiments of the first aspect of the invention, there is provided a compound of formula IA wherein when z represents 2, m represents 0 to 8 (e.g. 1) and $R^1$ represents $C_{1-6}$ alkyl (e.g. methyl, ethyl or n-propyl, such as ethyl or n-propyl, particularly n-propyl), such as $C_{2-6}$ alkyl (e.g. ethyl or n-propyl, particularly n-propyl). In such embodiments, $R^1$ may be located in the 2-, 3-, 4-, 5-, or 6-positions of the ring containing the essential nitrogen atom. In particular embodiments, the $R^1$ may be in the 6-position of the ring containing the essential nitrogen atom (with the point of attachment to the essential hydroxyl benzyl moiety being the 2-position).

In particular embodiments of the first aspect of the invention, there is provided a compound of formula IA wherein when z represents 0, m represents 1 and $R^1$ represents $C_{1-3}$ alkyl (e.g. $C_{2-3}$ alkyl), then the $R^1$ substituent is located in the 4-position of the ring containing the essential nitrogen atom (with the point of attachment to the essential hydroxyl benzyl moiety being the 2-position).

In alternative particular embodiments of the first aspect of the invention, there is provided a compound of formula IA wherein when z and m represent 1, and $R^1$ represents $C_{1-3}$ alkyl (e.g. $C_{2-3}$ alkyl), then the $R^1$ substituent is located in the 5-position of the ring containing the essential nitrogen atom (with the point of attachment to the essential hydroxyl benzyl moiety being the 2-position).

In further alternative embodiments of the first aspect of the invention, there is provided the the compound of formula IA wherein when z represents 2, m represents 1 and $R^1$ represents $C_{1-3}$ alkyl (e.g. $C_{2-3}$ alkyl), then the $R^1$ substituent is located in the 6-position of the ring containing the essential nitrogen atom (with the point of attachment to the essential hydroxyl benzyl moiety being the 2-position).

Accordingly, in preferred embodiments, wherein m represents 1, $R^1$ represents $C_{1-3}$ alkyl (e.g. $C_{2-3}$ alkyl) and may be located in:

when z represents 0, the 4-position of the ring containing the essential nitrogen atom (i.e. the 4-position of an azetidine ring); or when z represents 1, the 5-position of the ring containing the essential nitrogen atom (i.e. the 5-position of a pyrrolidine ring); or when z represents 2, the 6-position of the ring containing the essential nitrogen atom (i.e. the 6-position of a piperidine ring).

Thus, in particular embodiments of the first aspect of the invention, there is provided a compound of formula IB

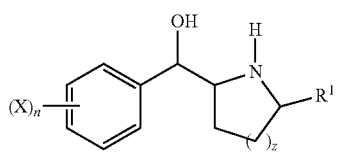

(IB)

or a pharmaceutically acceptable salt thereof, wherein $R^1$, X, n and z are as defined herein.

In certain embodiments of the compounds of the invention (i.e. compounds of formulae I, IA or IB) wherein each X independently represents halo (e.g. F or Cl), $R^a$, —CN, —$N_3$, —$N(R^b)R^c$, —$NO_2$ or —$OR^d$, wherein $R^a$ represents $C_{1-4}$ alkyl optionally substituted by one or more F, and wherein $R^b$, $R^c$ and $R^d$ each independently represent H or $C_{1-4}$ alkyl optionally substituted by one or more F.

For example, each X may independently represent halo, $R^a$, —CN, —$N_3$, —$N(R^b)R^c$, —$NO_2$ or —$OR^d$, wherein $R^a$ represents $C_{1-4}$ alkyl optionally substituted by one or more F, and $R^b$, $R^c$ and $R^d$ each independently represent H or $C_{1-4}$ alkyl optionally substituted by one or more F.

In further embodiments, each X may independently represent halo, $R^a$, —CN, —$N_3$, —$NH_2$, —$NO_2$ or —$OR^d$, wherein $R^a$ represents $C_{1-4}$ alkyl optionally substituted by one or more F, and each $R^d$ independently represents H or $C_{1-4}$ alkyl optionally substituted by one or more F (e.g. H).

In more particular embodiments, each X independently represents F, Cl, $R^a$, —$NH_2$, —CN or —OH, wherein $R^a$ represents $C_{1-4}$ alkyl (e.g. $C_{1-2}$ alkyl) optionally substituted by one or more F (for example $R^a$ represents —$CHF_2$ or —$CF_3$ (e.g. —$CF_3$)).

In yet more particular embodiments, each X independently represents F, Cl, $R^a$, —$NH_2$ or —OH, wherein $R^a$ represents $C_{1-2}$ alkyl optionally substituted by one or more F (for example $R^a$ represents —$CH_3$, —$CHF_2$ or —$CF_3$ (e.g. —$CF_3$)).

In further particular embodiments, each X independently represents F, Cl, $R^a$, or —OH, wherein $R^a$ represents $C_{1-2}$ alkyl optionally substituted by one or more F (e.g. —$CF_3$).

In yet further particular embodiments, each X independently represents F, Cl, —$NH_2$, —$CF_3$ or —OH. In a further embodiment, each X independently represents —OH.

In a certain embodiment, each X independently represents Cl or F (e.g. where n represents 0, 1 or 2, such as 1). In a further embodiment, each X independently represents F (e.g. where n represents 0, 1 or 2, such as 1).

In certain embodiments, where more than one X group is present (i.e. n represents 2 to 4, such as where n represents 2), only one X group may represent —$OR^d$. For example, in certain embodiments, where more than one X group is present (i.e. n represents 2 to 4, such as where n represents 2), only one X group may represent —OH.

In some embodiments of the compounds of the invention, n represents 0, 1, 2 or 3 (for example 1 or 2, e.g. 1).

In certain embodiments of the compounds of the invention, n represents 0, 1 or 2 (e.g. 0 or 1).

In other embodiments of the compounds of the invention, n represents 1, 2 or 3 (e.g. 1 or 2).

In particular embodiments of the compounds of the invention, n represents 0 or 1 (e.g. 1).

In certain embodiments, wherein n represents 0 to 3 (e.g. 3), each X independently represents halo (e.g. F or Cl, such as F), —$NH_2$, —$CF_3$ or —OH. In further certain embodiments, wherein n represents 3, each X independently represents F, —$NH_2$ or —OH. In such embodiments, the X groups may be located in the 3-, 4- and 5-positions of the essential benzene ring.

In certain embodiments, wherein n represents 0 to 2 (e.g. 2), each X independently represents F, Cl, —$NH_2$, or —OH. In such embodiments, the X groups may be located in the 3- and 4-positions, or the 3- and 5-positions of the essential benzene ring.

In certain embodiments, wherein n represents 0 to 2 (e.g. 2), each X independently represents F or —OH. In such embodiments, the X groups may be located in the 3- and 4-positions, or the 3- and 5-positions of the essential benzene ring.

In certain embodiments, where n represents 1, X represents Cl, F or —OH (e.g. Cl or F, such as F). In such embodiments, the X group may be located in 3-position of the essential benzene ring.

In further embodiments:

n represents 2 or 3 and/or (e.g. and)

each X independently represents halo (e.g. F or Cl, such as F), —$NH_2$, —$CF_3$ or —OH, particularly where such X groups are located in the 3-, 4- and 5-positions of the essential benzene ring.

In further embodiments, there is provided a compound of formula I, or a pharmaceutically acceptable salt thereof, wherein the essential benzene ring is unsubstituted in the 2- and 6-positions.

In particular embodiments of the first aspect of the invention:

each X independently represents halo, $R^a$ or $-OR^d$;

$R^a$ represents $C_{1-4}$alkyl optionally substituted by one or more F;

$R^d$ represents H or $C_{1-4}$alkyl optionally substituted by one or more F; and/or (e.g. and)

n represents 0, 1, 2 or 3.

In more particular embodiments:

each X independently represents F, Cl, $R^a$ or $-OH$;

$R^a$ represents $C_{1-2}$alkyl optionally substituted by one or more F; and/or (e.g. and)

n represents 0, 1 or 2 (e.g. 1 or 2).

In yet more particular embodiments:

each X independently represents F, Cl, $-CH_3$ or $-OH$;

n represents 1 or 2 (e.g. 1); and/or (e.g. and) at least one X is in the 3- or in the 4-position on the phenyl group to which it is attached.

Examples of more particular embodiments include those wherein:

X independently represents F or $-OH$ which substituents are in the 3- and 4-position on the phenyl group to which they are attached; and n represents 2.

Examples of more particular embodiments include those wherein:

X independently represents F is in the 3- and 5-position on the phenyl group to which they are attached; and n represents 2.

Other examples of more particular embodiments include those wherein X represents F, Cl, $R^a$ or $-OH$, $R^a$ represents $C_{1-2}$ alkyl optionally substituted by one or more F (for example, $R^a$ may represent $-CH_3$, $-CF_3$ or $-CHF_2$ (e.g. $-CHF_2$)) and n represents 1.

Yet more examples of more particular embodiments include those wherein X represents F or $-OH$ (e.g. $-OH$) and n represents 1. Examples of such embodiments include those wherein the X substituents are in the 3- and 4-position on the phenyl group to which they are attached.

Further examples of more particular embodiments include those wherein:

X represents F or $-OH$ (e.g. $-OH$) in the 3-position on the phenyl group to which it is attached; and n represents 1.

More examples of more particular embodiments include those wherein:

X represents Cl, F or $-OH$ (e.g. F) in the 3-position on the phenyl group to which it is attached; and n represents 1.

More examples of more particular embodiments include those wherein:

X represents Cl or F in the 2-position on the phenyl group to which it is attached; and n represents 1.

Alternative further examples of more particular embodiments include those wherein:

X represents F or $-OH$ (e.g. $-OH$) in the 4-position on the phenyl group to which it is attached; and n represents 1.

In particular embodiments that may be mentioned, at least one X is present (i.e. n represents at least 1) and represents other than $-OH$.

In more particular embodiments that may be mentioned, at least one X is present and represents F.

In a particular embodiment of the first aspect of the invention, there is provided a compound of formula IB wherein:

n and z represents 1

$R^1$ represents $-CH_3$ or n-propyl (e.g. n-propyl); and

X represents F or $-OH$ (e.g. F) and is in the 4-position on the phenyl group to which it is attached.

In another particular example of the first aspect of the invention, there is provided a compound of formula IB wherein:

n and represents 1

$R^1$ represents H;

$R^2$ represents $-CH_3$ or n-propyl; and

X represents F or $-OH$ (e.g. F) and is in the 3-position on the phenyl group to which it is attached.

In certain embodiments that may be mentioned, when n represents 2 or more (i.e. more than one X substituent is present), no more than one X may represent a group selected from $-N(R^b)R^c$ and $-OR^d$ (particularly where $R^b$, $R^c$ and $R^d$ represent H).

For the avoidance of doubt, in a particular example of a compound of formula IB wherein n represents 1, z represents 2, $R^1$ represents H, $R^2$ represents n-propyl, and X is F and is in the 4-position on the phenyl group to which it is attached, the compound of formula I may be depicted as:

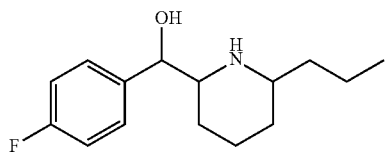 [SMILES: CCCC1CCCC(C(O)c2ccc(F)cc2)N1]

In further particular embodiments of the compounds of the invention, the compound of formula I is a compound of formula IC

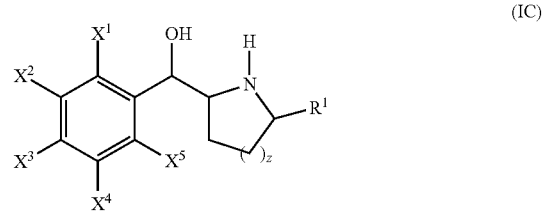

(IC)

wherein z and $R^1$ are as defined herein (for the avoidance of doubt, including all embodiments thereof), and $X^1$, $X^2$, $X^3$, $X^4$ and $X^5$ each independently represent H or X, wherein X is as defined herein (including all embodiments thereof).

In certain embodiments, there is provided a compound of formula IC, wherein:

$X^1$ and $X^5$ each independently represent H, F or Cl; and $X^2$, $X^3$ and $X^4$ each independently represent H, halo (e.g. F or Cl, such as F), $R^a$, $-CN$, $-N_3$, $-N(R^b)R^c$, $-NO_2$ or $-OR^d$, wherein $R^a$ represents $C_{1-4}$ alkyl optionally substituted by one or more F, and wherein $R^b$, $R^c$ and $R^d$ each independently represent H or $C_{1-4}$ alkyl optionally substituted by one or more F.

In particular embodiments, there is provided a compound of formula IC, wherein $X^1$ represents H.

In further embodiments, there is provided a compound of formula IC, wherein $X^3$ represents H, F, $-NH_2$ or $-OH$.

In particular embodiments, there is provided a compound of formula IC, wherein $X^3$ represents H, F or $-OH$.

In more particular embodiments, there is provided a compound of formula IC, wherein $X^3$ represents F or $-OH$.

In yet more particular embodiments, there is provided a compound of formula IC, wherein $X^3$ represents F.

In certain embodiments, there is provided a compound of formula IC, wherein $X^2$ represents Cl, F or $-OH$ (e.g. F), such as wherein $X^1$, $X^3$, $X^4$ and $X^5$ represent H.

Thus, in further embodiments, there is provided a compound of formula IC, wherein:

$X^1$ represents H; and $X^5$ represents H, F, Cl or —$CH_3$; and $X^2$, $X^3$ and $X^4$ each independently represent H, halo, $R^a$, —CN, —$N_3$, —N($R^b$)$R^c$, —$NO_2$ or —$OR^d$, wherein $R^a$ represents $C_{1-4}$ alkyl optionally substituted by one or more F, and wherein $R^b$, $R^c$ and $R^d$ each independently represent H or $C_{1-4}$ alkyl optionally substituted by one or more F.

In particular embodiments:

$X^1$, $X^2$ and $X^5$ each represent H; and $X^3$ and $X^4$ each independently represent H, halo, $R^a$, —CN, —$NH_2$, or —OH, wherein $R^a$ represents $C_{1-2}$ alkyl optionally substituted by one or more F (for example, $R^a$ may represent —$CF_3$ or —$CHF_2$).

In further particular embodiments:

$X^1$, $X^2$ and $X^5$ each represent H; and $X^3$ and $X^4$ each independently represent H, halo, —$NH_2$, —CN or —OH.

In more particular embodiments:

$X^1$, $X^2$ and $X^5$ each represent H; and $X^3$ and $X^4$ each independently represent H, halo (e.g. F, Cl), —$NH_2$ or —OH.

In yet more particular embodiments:

$X^1$, $X^2$ and $X^5$ each represent H; and $X^3$ and $X^4$ each independently represent H, F, Cl, —$NH_2$ or —OH.

In yet more particular embodiments:

$X^1$, $X^2$ and $X^5$ each represent H; and $X^3$ and $X^4$ each independently represent H, F or —OH.

In certain embodiments:

$X^1$, $X^2$, $X^3$, $X^4$ and $X^5$ each represent H; or $X^1$, $X^2$, $X^3$ and $X^5$ represent H and $X^4$ represents F or —OH (e.g. F);

$X^1$, $X^2$, $X^4$ and $X^5$ represent H and $X^3$ represents F or —OH (e.g. F).

In alternative embodiments:

$X^1$ and $X^5$ each represent H;

$X^2$ and $X^4$ each independently represent halo, $R^a$, —CN, —$N_3$, —N($R^b$)$R^c$, —$NO_2$ or —$OR^d$;

wherein $R^a$ represents $C_{1-4}$ alkyl optionally substituted by one or more F, and wherein $R^b$, $R^c$ and $R^d$ each independently represents H or $C_{1-4}$ alkyl optionally substituted by one or more F; and $X^3$ represents H, halo, $R^a$, —CN, —$N_3$, —N($R^b$)$R^c$, —$NO_2$ or —$OR^d$; wherein $R^a$ represents $C_{1-4}$ alkyl optionally substituted by one or more F, and wherein $R^b$, $R^c$ and $R^d$ each independently represents H or $C_{1-4}$ alkyl optionally substituted by one or more F.

In further alternative embodiments:

$X^1$ and $X^5$ each represent H;

$X^2$ and $X^4$ each independently represent F, Cl, $R^a$ or $OR^d$; wherein $R^a$ represents $C_{1-2}$ alkyl optionally substituted by one or more F, and wherein $R^d$ represents H or $C_{1-2}$ alkyl optionally substituted by one or more F; and $X^3$ represents H, —N($R^b$)$R^c$ or —$OR^d$; wherein $R^b$, $R^c$ and $R^d$ each independently represent H or $C_{1-2}$ alkyl optionally substituted by one or more F.

In yet more particular embodiments:

$X^1$ and $X^5$ each represent H;

$X^2$ and $X^4$ each independently represent F, Cl, —$CF_3$ or —OH; and $X^3$ represents H, —$NH_2$ or —OH.

In yet more alternative embodiments:

$X^1$ and $X^5$ each represent H;

$X^2$ and $X^4$ each independently represent F or —OH; and $X^3$ represents H or —OH.

In certain embodiments:

$X^1$, $X^3$ and $X^5$ each represent H; and $X^2$ and $X^4$ each represent F.

In further embodiments:

$X^1$, $X^3$ and $X^4$ each represent H; and $X^2$ and $X^3$ each represent F.

In further embodiments:

$X^1$, $X^3$, $X^4$ and $X^5$ represent H; and $X^2$ represents H, F or —OH.

In further embodiments:

$X^1$, $X^3$, $X^4$ and $X^5$ represent H; and $X^2$ represents H, Cl, F or —OH (e.g. Cl, F or —OH, such as F).

In further embodiments:

$X^2$, $X^3$, $X^4$ and $X^5$ represent H; and $X^1$ represents H, Cl or F (e.g. Cl or F, such as F).

In further embodiments:

$X^1$, $X^2$, $X^4$ and $X^5$ represent H; and $X^3$ represents H or F (e.g. F).

The skilled person will understand that particular X groups (and the positions and number thereof, such as may correspond to $X^1$ to $X^5$ groups in compounds of formula IC) that may be mentioned include those present in the examples provided herein.

Similarly, the skilled person will understand that particular $R^1$, $R^2$ and $R^3$ groups that may be mentioned include those present in the examples provided herein.

For example, in a particular embodiment of a compound of formula IC:

$R^1$ represents methyl or n-propyl;

n represents 1; and

X represents —OH and is in the 3-position on the phenyl group to which it is attached (i.e. in a compound of formula IC, $X^1$, $X^3$, $X^4$ and $X^5$ represent H and $X^2$ represents —OH).

As described herein, compounds of the first aspect of the invention may also contain one or more asymmetric carbon atoms and may therefore exhibit optical and/or diastereoisomerism. Moreover, it has been found that certain such optical and/or diastereoisomers may show increased utility in the treatment of hyperglycaemia or disorders characterized by hyperglycaemia (such as type 2 diabetes), as described herein.

The skilled person will understand that the compound of formula I may be such that the carbon substituted with the essential —OH group is in the (R) configuration or the (S) configuration, as understood by those skilled in the art.

In particular embodiments, the carbon substituted with the essential —OH group is in the (R) configuration.

For example, the compound of formula I may be a compound of formulae ID or IE

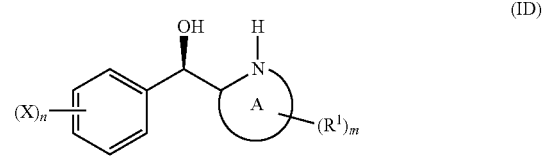

(ID)

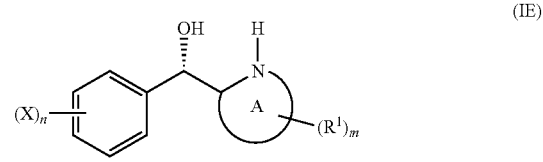

(IE)

wherein n, m, A, X and R¹ are as described herein (i.e. as described in the first aspect of the invention, including all embodiments and particular features, and combinations thereof).

In a particular embodiment, the compound of formula I is a compound of formula ID.

As such, the compound of formula ID may be a compound of formula IF, and the compound of formula IE may be a compound of formula IG

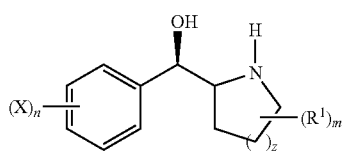

(IF)

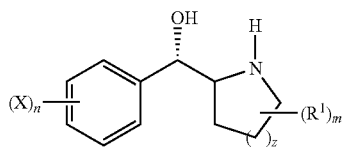

(IG)

wherein:
n, z, X and R¹ are as defined herein,
such as wherein
z represents 0, 1 or 2,
n represents 1 or 2 and X represents F or —OH and is in the 3- and/or (e.g or) 4-position of the phenyl group, and
R¹ is as defined herein (e.g. methyl, ethyl or n-propyl, such as ethyl or n-propyl, particularly n-propyl).

In particular embodiments, the compound of formula I is a compound of formula IF.

In particular, the compound of formula IF may be a compound of formula IH, and the compound of formula IG may be a compound of formula IJ

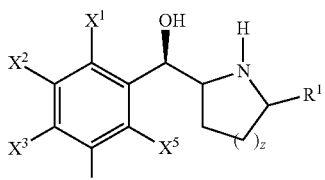

(IH)

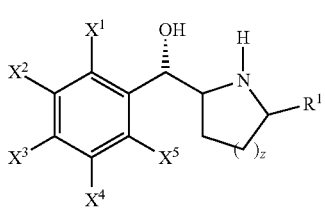

(IJ)

wherein z, $X^1$, $X^2$, $X^3$, $X^4$, $X^5$, $R^1$ and $R^2$ are as described herein (i.e. as described in the first aspect of the invention, including all embodiments and particular features, and combinations thereof).

In a particular embodiment, the compound of formula I is a compound of formula IH.

The skilled person will understand that, in addition to the carbon bearing the essential hydroxy group, compounds of the invention may comprise further stereocentres. For the avoidance of doubt, unless specified, the stereochemistry at all stereocentres (including stereochemistry present in positions other than the carbon bearing the essential hydroxy group) may be in either configuration (i.e. in the R or S configuration), or may be present in compounds as a mixture thereof (e.g. a racemic mixture).

In particular embodiments, the compound of formula IH is a compound of formula IK or a compound of formula IL

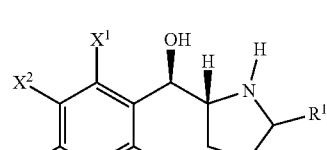

(IK)

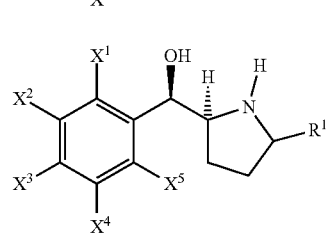

(IL)

wherein $X^1$, $X^2$, $X^3$, $X^4$, $X^5$, $R^1$ and z are as defined in herein (i.e. as described in the first aspect of the invention, including all embodiments and particular features, and combinations thereof).

In further particular embodiments, the compound of formula IK is a compound of formula IM or a compound of formula IN, and the compound of formula IL is a compound of formula IO or a compound of formula IP

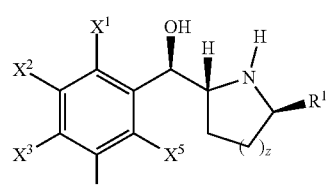

(IM)

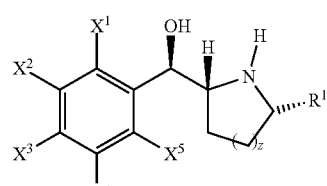

(IN)

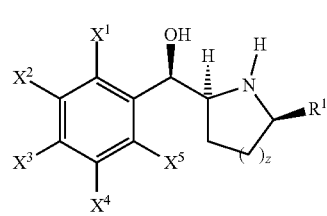

(IO)

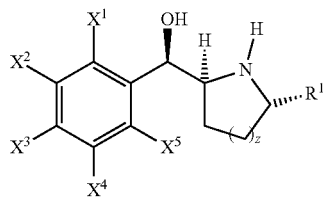

(IP)

wherein $X^1$, $X^2$, $X^3$, $X^4$, $X^5$, $R^1$ and z are as defined herein (i.e. as described in the first aspect of the invention, including all embodiments and particular features, and combinations thereof).

In particular embodiments of the invention, there is provided a compound of any one of formulae IA to IP wherein:
$X^1$ and $X^5$ each represent H;
$X^2$ represents H, F or —OH;
$X^3$ and $X^4$ each independently H or F
z represents 0; and
$R^1$ represents H, methyl, ethyl or n-propyl (e.g. ethyl or n-propyl, such as n-propyl).

In alternative embodiments of the invention, there is provided a compound of any one of formulae IA to IP wherein:
$X^1$ and $X^5$ each represent H;
$X^2$ represents H, F or —OH;
$X^3$ and $X^4$ each independently H or F
z represents 1; and
$R^1$ represents H, methyl, ethyl or n-propyl (e.g. ethyl or n-propyl, such as n-propyl).

In further alternative embodiments of the invention, there is provided a compound of any one of formulae IA to IP wherein:
$X^1$ and $X^5$ each represent H;
$X^2$ represents H, F or —OH;
$X^3$ and $X^4$ each independently H or F
z represents 2; and
$R^1$ represents H, methyl, ethyl or n-propyl (e.g. ethyl or n-propyl, such as n-propyl).

In particular embodiments, the compound of the invention is not a compound selected from the list consisting of:
(5-methylpyrrolidin-2-yl)(phenyl)methanol;
(S)-(3,4-dichlorophenyl)((2S,5S)-5-methylpyrrolidin-2-yl)methanol;
rel-(1R)-((2S)-4-methylpyrrolidin-2-yl)(phenyl)methanol;
(1S)-((2R)-4-methylpyrrolidin-2-yl)(phenyl)methanol;
(S)-((2R,4S)-4-methylpyrrolidin-2-yl)(phenyl)methanol;
(S)-((2R,4R)-4-methylpyrrolidin-2-yl)(phenyl)methanol;
(4-methylpyrrolidin-2-yl)(phenyl)methanol;
(3-methylpyrrolidin-2-yl)(phenyl)methanol;
(6-methylpiperidin-2-yl)(phenyl)methanol;
(R)-(4-methoxyphenyl)((2R,6S)-6-methylpiperidin-2-yl)methanol;
rel-(R)-(4-methoxyphenyl)((2R,6S)-6-methylpiperidin-2-yl)methanol;
rel-(S)-(4-methoxyphenyl)((2S,6R)-6-methylpiperidin-2-yl)methanol;
4-(hydroxy(6-methylpiperidin-2-yl)methyl)benzene-1,2-diol;
2-amino-4-(hydroxy(6-methylpiperidin-2-yl)methyl)phenol;
2-hydroxy-5-(hydroxy(6-methylpiperidin-2-yl)methyl)benzamide;
2-(2-hydroxy-5-(hydroxy(6-methylpiperidin-2-yl)methyl)phenyl)acetamide;
4-(hydroxy(5-methylpiperidin-2-yl)methyl)benzene-1,2-diol;
2-amino-4-((5-butylpiperidin-2-yl)(hydroxy)methyl)phenol;
5-((5-butylpiperidin-2-yl)(hydroxy)methyl)-2-hydroxybenzamide;
2-(5-((5-butylpiperidin-2-yl)(hydroxy)methyl)-2-hydroxyphenyl)acetamide;
(3-methylpiperidin-2-yl)(phenyl)methanol;
4-(hydroxy(3-methylpiperidin-2-yl)methyl)benzene-1,2-diol;
(4-methylpiperidin-2-yl)(phenyl)methanol;
4-(hydroxy(4-methylpiperidin-2-yl)methyl)benzene-1,2-diol;
(4-(tert-butyl)piperidin-2-yl)(phenyl)methanol;
rel-(S)-((2R,4S)-4-(tert-butyl)piperidin-2-yl)(phenyl)methanol;
rel-(S)-((2S,4R)-4-(tert-butyl)piperidin-2-yl)(phenyl)methanol; and
(4-ethylpiperidin-2-yl)(phenyl)methanol.

In more particular embodiments, the compound of the invention is not a compound selected from the list consisting of:
(5-methylpyrrolidin-2-yl)(phenyl)methanol;
(S)-(3,4-dichlorophenyl)((2S,5S)-5-methylpyrrolidin-2-yl)methanol;
rel-(1R)-((2S)-4-methylpyrrolidin-2-yl)(phenyl)methanol;
(1S)-((2R)-4-methylpyrrolidin-2-yl)(phenyl)methanol;
(S)-((2R,4S)-4-methylpyrrolidin-2-yl)(phenyl)methanol;
(S)-((2R,4R)-4-methylpyrrolidin-2-yl)(phenyl)methanol;
(4-methylpyrrolidin-2-yl)(phenyl)methanol;
(3-methylpyrrolidin-2-yl)(phenyl)methanol;
(6-methylpiperidin-2-yl)(phenyl)methanol;
(R)-(4-methoxyphenyl)((2R,6S)-6-methylpiperidin-2-yl)methanol;
rel-(R)-(4-methoxyphenyl)((2R,6S)-6-methylpiperidin-2-yl)methanol;
rel-(S)-(4-methoxyphenyl)((2S,6R)-6-methylpiperidin-2-yl)methanol;
4-(hydroxy(6-methylpiperidin-2-yl)methyl)benzene-1,2-diol;
2-amino-4-(hydroxy(6-methylpiperidin-2-yl)methyl)phenol;
2-hydroxy-5-(hydroxy(6-methylpiperidin-2-yl)methyl)benzamide;
2-(2-hydroxy-5-(hydroxy(6-methylpiperidin-2-yl)methyl)phenyl)acetamide;
4-(hydroxy(5-methylpiperidin-2-yl)methyl)benzene-1,2-diol;
2-amino-4-((5-butylpiperidin-2-yl)(hydroxy)methyl)phenol;
5-((5-butylpiperidin-2-yl)(hydroxy)methyl)-2-hydroxybenzamide;
2-(5-((5-butylpiperidin-2-yl)(hydroxy)methyl)-2-hydroxyphenyl)acetamide;
(3-methylpiperidin-2-yl)(phenyl)methanol;
4-(hydroxy(3-methylpiperidin-2-yl)methyl)benzene-1,2-diol;
(4-methylpiperidin-2-yl)(phenyl)methanol;
4-(hydroxy(4-methylpiperidin-2-yl)methyl)benzene-1,2-diol;
(4-(tert-butyl)piperidin-2-yl)(phenyl)methanol;
rel-(S)-((2R,4S)-4-(tert-butyl)piperidin-2-yl)(phenyl)methanol;
rel-(S)-((2S,4R)-4-(tert-butyl)piperidin-2-yl)(phenyl)methanol; and (4-ethylpiperidin-2-yl)(phenyl)methanol,
and pharmaceutically acceptable salts thereof.

In yet more particular embodiments, the compound of the invention is not a compound selected from the list consisting of:
(5-methylpyrrolidin-2-yl)(phenyl)methanol;
3,4-dichlorophenyl(5-methylpyrrolidin-2-yl)methanol;
4-methylpyrrolidin-2-yl(phenyl)methanol;
4-methylpyrrolidin-2-yl(phenyl)methanol;
4-methylpyrrolidin-2-yl(phenyl)methanol;
4-methylpyrrolidin-2-yl(phenyl)methanol;
4-methylpyrrolidin-2-yl(phenyl)methanol;
3-methylpyrrolidin-2-yl(phenyl)methanol;
6-methylpiperidin-2-yl(phenyl)methanol;
4-methoxyphenyl(6-methylpiperidin-2-yl)methanol;
4-methoxyphenyl(6-methylpiperidin-2-yl)methanol;
4-methoxyphenyl(6-methylpiperidin-2-yl)methanol;
4-(hydroxy(6-methylpiperidin-2-yl)methyl)benzene-1,2-diol;
2-amino-4-(hydroxy(6-methylpiperidin-2-yl)methyl)phenol;
2-hydroxy-5-(hydroxy(6-methylpiperidin-2-yl)methyl)benzamide;
2-(2-hydroxy-5-(hydroxy(6-methylpiperidin-2-yl)methyl)phenyl)acetamide;
4-(hydroxy(5-methylpiperidin-2-yl)methyl)benzene-1,2-diol;
2-amino-4-((5-butylpiperidin-2-yl)(hydroxy)methyl)phenol;
5-((5-butylpiperidin-2-yl)(hydroxy)methyl)-2-hydroxybenzamide;
2-(5-((5-butylpiperidin-2-yl)(hydroxy)methyl)-2-hydroxyphenyl)acetamide;
(3-methylpiperidin-2-yl)(phenyl)methanol;
4-(hydroxy(3-methylpiperidin-2-yl)methyl)benzene-1,2-diol;
(4-methylpiperidin-2-yl)(phenyl)methanol;
4-(hydroxy(4-methylpiperidin-2-yl)methyl)benzene-1,2-diol;
(4-(tert-butyl)piperidin-2-yl)(phenyl)methanol;
4-(tert-butyl)piperidin-2-yl(phenyl)methanol;
4-(tert-butyl)piperidin-2-yl(phenyl)methanol; and
4-ethylpiperidin-2-yl(phenyl)methanol,
and pharmaceutically acceptable salts thereof.

In a certain embodiment, the compound of the invention is not 4-ethylpiperidin-2-yl(phenyl)methanol, or a pharmaceutically acceptable salt thereof (e.g. the HCl salt).

In further embodiments, the compound of the invention is not (or, is also not) 4-(hydroxy(piperidin-2-yl)methyl)benzene-1,2-diol, or a pharmaceutically acceptable salt thereof.

Particular compounds of the first aspect of the invention that may be mentioned include the compounds of the examples provided herein, and pharmaceutically acceptable salts thereof. Thus, compounds of the invention that may be mentioned include:
3-fluorophenyl(6-propylpiperidin-2-yl)methanol;
3,5-difluorophenyl(6-propylpiperidin-2-yl)methanol;
3,4-difluorophenyl(6-propylpiperidin-2-yl)methanol;
3-(hydroxy(6-propylpiperidin-2-yl)methyl)phenol;
3-fluorophenyl(5-propylpyrrolidin-2-yl)methanol;
3-(hydroxy(5-propylpyrrolidin-2-yl)methyl)phenol;
3-(hydroxy(5-methylpyrrolidin-2-yl)methyl)phenol; and
5-methylpyrrolidin-2-yl(phenyl)methanol,
and pharmaceutically acceptable salts thereof.

More particular compounds of the invention (particularly, compounds of formulae ID to IP) that may be mentioned include:

(R)-(3-fluorophenyl)((2R,6R)-6-propylpiperidin-2-yl)methanol;
(R)-(3-fluorophenyl)((2R,6S)-6-propylpiperidin-2-yl)methanol;
(R)-(3,5-difluorophenyl)((2R,6S)-6-propylpiperidin-2-yl)methanol;
(R)-(3,4-difluorophenyl)((2R,6S)-6-propylpiperidin-2-yl)methanol;
3-((R)-hydroxy((2R,6S)-6-propylpiperidin-2-yl)methyl)phenol;
3-((R)-hydroxy((2R,6R)-6-propylpiperidin-2-yl)methyl)phenol;
(R)-(3-fluorophenyl)((2R,5R)-5-propylpyrrolidin-2-yl)methanol;
3-((R)-hydroxy((2R,5R)-5-propylpyrrolidin-2-yl)methyl)phenol;
3-((R)-hydroxy(5-methylpyrrolidin-2-yl)methyl) phenol; and
(R)-(5-methylpyrrolidin-2-yl)(phenyl)methanol,
and pharmaceutically acceptable salts thereof.

Yet more particular compounds of formula I that may be mentioned include:
(R)-(3-fluorophenyl)((2R,6R)-6-propylpiperidin-2-yl)methanol;
(R)-(3-fluorophenyl)((2R,6S)-6-propylpiperidin-2-yl)methanol;
(R)-(3,5-difluorophenyl)((2R,6S)-6-propylpiperidin-2-yl)methanol;
(R)-(3,4-difluorophenyl)((2R,6S)-6-propylpiperidin-2-yl)methanol;
3-((R)-hydroxy((2R,6S)-6-propylpiperidin-2-yl)methyl)phenol;
3-((R)-hydroxy((2R,6R)-6-propylpiperidin-2-yl)methyl)phenol;
(R)-(3-fluorophenyl)((2R,5R)-5-propylpyrrolidin-2-yl)methanol;
3-((R)-hydroxy((2R,5R)-5-propylpyrrolidin-2-yl)methyl)phenol;
3-((R)-hydroxy((2S,5S)-5-methylpyrrolidin-2-yl)methyl)phenol;
3-((R)-hydroxy((2R,5R)-5-methylpyrrolidin-2-yl)methyl)phenol;
(R)-((2S,5S)-5-methylpyrrolidin-2-yl)(phenyl)methanol; and
(R)-((2R,5R)-5-methylpyrrolidin-2-yl)(phenyl)methanol,
and pharmaceutically acceptable salts thereof.

Further compounds of formula I that may be mentioned include:
3-Fluorophenyl(6-propylpiperidin-2-yl)methanol;
3-(Hydroxy(6-propylpiperidin-2-yl)methyl)phenol;
4-Fluorophenyl(-6-propylpiperidin-2-yl)methanol;
2-Fluorophenyl(6-propylpiperidin-2-yl)methanol;
2-Fluorophenyl(6-propylpiperidin-2-yl)methanol;
3-Fluorophenyl(-6-propylpiperidin-2-yl)methanol;
3-(Hydroxy(6-propylpiperidin-2-yl)methyl)phenol;
3-Chlorophenyl(6-propylpiperidin-2-yl)methanol;
3-Chlorophenyl(6-propylpiperidin-2-yl)methanol;
2-Fluorophenyl(6-propylpiperidin-2-yl)methanol;
2-Fluorophenyl(6-propylpiperidin-2-yl)methanol;
2-Chlorophenyl(6-propylpiperidin-2-yl)methanol;
4-Fluorophenyl(6-propylpiperidin-2-yl)methanol;
4-Fluorophenyl(6-propylpiperidin-2-yl)methanol;
3,5-Difluorophenyl(6-propylpiperidin-2-yl)methanol;
3,4-Difluorophenyl)(6-propylpiperidin-2-yl)methanol;
3-Fluorophenyl(6-propylpiperidin-2-yl)methanol;
3-Chlorophenyl(6-propylpiperidin-2-yl)methanol;
3-Chlorophenyl(6-propylpiperidin-2-yl)methanol;

3-(Hydroxy(6-propylpiperidin-2-yl)methyl)phenol;
3-(Hydroxy(6-propylpiperidin-2-yl)methyl)phenol;
3-Fluorophenyl(6-propylpiperidin-2-yl)methanol;
3-Fluorophenyl(6-propylpiperidin-2-yl)methanol;
3-Chlorophenyl(6-propylpiperidin-2-yl)methanol;
3-Hydroxyphenyl(6-propylpiperidin-2-yl)methanol;
3-Hydroxyphenyl(6-propylpiperidin-2-yl)methanol;
3-Fluorophenyl(5-propylpyrrolidin-2-yl)methanol;
3-(Hydroxy(5-propylpyrrolidin-2-yl)methyl)phenol;
3-Fluorophenyl(5-propylpyrrolidin-2-yl)methanol;
3-Fluorophenyl(5-propylpyrrolidin-2-yl)methanol;
3-Fluorophenyl(5-propylpyrrolidin-2-yl)methanol;
3-Fluorophenyl(5-propylpyrrolidin-2-yl)methanol;
3-Fluorophenyl(5-propylpyrrolidin-2-yl)methanol;
3-(Hydroxy(5-propylpyrrolidin-2-yl)methyl)phenol;
3-Chlorophenyl(5-propylpyrrolidin-2-yl)methanol; and
3-Chlorophenyl(5-propylpyrrolidin-2-yl)methanol,
and pharmaceutically acceptable salts thereof.

Yet further compounds of formula I that may be mentioned include:
(S)-(3-Fluorophenyl)((2R,6R)-6-propyl piperidin-2-yl)methanol;
3-((S)-Hydroxy((2R,6R)-6-propyl piperidin-2-yl)methyl)phenol;
(R)-(4-Fluorophenyl)((2R,6R)-6-propylpiperidin-2-yl)methanol;
(R)-(2-Fluorophenyl)((2R,6R)-6-propylpiperidin-2-yl)methanol;
(S)-(2-Fluorophenyl)((2R,6R)-6-propyl piperidin-2-yl)methanol;
(S)-(3-Fluorophenyl)((2R,6S)-6-propylpiperidin-2-yl)methanol;
3-((R)-Hydroxy((2R,6R)-6-propylpiperidin-2-yl)methyl)phenol;
(R)-(3-Chlorophenyl)((2R,6S)-6-propylpiperidin-2-yl)methanol;
(S)-(3-Chlorophenyl)((2R,6S)-6-propylpiperidin-2-yl)methanol;
(R)-(2-Fluorophenyl)((2R,6S)-6-propylpiperidin-2-yl)methanol;
(S)-(2-Fluorophenyl)((2R,6S)-6-propylpiperidin-2-yl)methanol;
(R)-(2-Chlorophenyl)((2R,6S)-6-propylpiperidin-2-yl)methanol;
(R)-(4-Fluorophenyl)((2R,6S)-6-propylpiperidin-2-yl)methanol;
(S)-(4-Fluorophenyl)((2R,6S)-6-propylpiperidin-2-yl)methanol;
(S)-(3,5-Difluorophenyl)((2R,6S)-6-propylpiperidin-2-yl)methanol;
(S)-(3,4-Difluorophenyl)((2R,6S)-6-propylpiperidin-2-yl)methanol;
(R)-(3-Fluorophenyl)((2S,6R)-6-propylpiperidin-2-yl)methanol;
(R)-(3-Chlorophenyl)((2S,6R)-6-propylpiperidin-2-yl)methanol;
(S)-(3-Chlorophenyl)((2S,6R)-6-propylpiperidin-2-yl)methanol;
3-((R)-hydroxy((2S,6R)-6-propylpiperidin-2-yl)methyl)phenol;
3-((S)-hydroxy((2S,6R)-6-propylpiperidin-2-yl)methyl)phenol;
(R)-(3-Fluorophenyl)((2S,6S)-6-propylpiperidin-2-yl)methanol;
(S)-(3-Fluorophenyl)((2S,6S)-6-propylpiperidin-2-yl)methanol;
(R)-(3-Chlorophenyl)((2S,6S)-6-propylpiperidin-2-yl)methanol;
(R)-(3-Hydroxyphenyl)((2S,6S)-6-propylpiperidin-2-yl)methanol;
(S)-(3-Hydroxyphenyl)((2S,6S)-6-propylpiperidin-2-yl)methanol;
(S)-(3-Fluorophenyl)((2R,5R)-5-propylpyrrolidin-2-yl)methanol;
3-((S)-Hydroxy((2R,5R)-5-propylpyrrolidin-2-yl)methyl)phenol;
(R)-(3-fluorophenyl)((2S,5S)-5-propylpyrrolidin-2-yl)methanol;
(S)-(3-Fluorophenyl)((2S,5S)-5-propylpyrrolidin-2-yl)methanol;
(R)-(3-Fluorophenyl)((2S,5R)-5-propylpyrrolidin-2-yl)methanol;
(S)-(3-Fluorophenyl)((2S,5R)-5-propylpyrrolidin-2-yl)methanol;
(R)-(3-Fluorophenyl)((2R,5S)-5-propylpyrrolidin-2-yl)methanol;
3-((R)-Hydroxy((2R,5S)-5-propylpyrrolidin-2-yl)methyl)phenol;
(R)-(3-Chlorophenyl)((2R,5R)-5-propylpyrrolidin-2-yl)methanol; and
(R)-(3-Chlorophenyl)((2R,5R)-5-propylpyrrolidin-2-yl)methanol,
and pharmaceutically acceptable salts thereof.

The skilled person will understand that references to specific stereoisomer(s) of a compound of formula I (e.g. in the case of compounds of formula I, where the carbon substituted by the essential —OH group is in the R configuration, as represented by compounds of formulae ID, IF, IH, IK, IL, IM, IN, IO, IP) will refer to the specific stereoisomer present in the substantial absence of the other (corresponding) stereoisomer(s) (e.g. in the case of compounds of formula I, where the carbon substituted by the essential —OH group is in the opposite configuration, i.e. the S configuration).

For example, references to a compound of formula IH will refer to that compound being present being present in the substantial absence of the corresponding opposite stereoisomer (i.e a compound of formula IJ).

As used herein, references to the substantial absence of the corresponding opposite stereoisomer will refer to the desired stereoisomer (e.g. in the case of compounds of formula I, where the carbon substituted by the essential —OH group is in the (R) configuration) being present at a purity of at least 80% (e.g. at least 90%, such as at least 95%) relative to the opposite stereoisomer (e.g. in the case of compounds of formula I, where the carbon substituted by the essential —OH group is in the S configuration). Alternatively, in such instances, compounds may be indicated to be present in the substantial absence of the compound in the other configuration (i.e. (S) configuration), which may indicate that the compound in the relevant configuration is present in an enantiomeric excess (e.e.), or when two or more stereogenic centres are defined, in a diastereomeric excess (d.e.), of at least 90% (such as at least 95%, at least 98% or, particularly, at least 99%, for example at least 99.9%).

For the avoidance of doubt, where the stereochemistry of more than one position is specified, the compound will be present in the substantial absence of all other diastereoisomers.

For the avoidance of doubt, where the stereochemistry of a particular position is not specified, compounds of the invention will include compounds wherein that position has either available stereochemical configuration, and mixtures (e.g. racemic mixtures) thereof. Thus, compounds referred to as having a specific stereochemistry at a defined position (e.g. in the case of compounds of formula I, the carbon substituted by the essential —OH group being in the R configuration) may also have stereochemistry at one or more other positions, and so may exist as mixtures of enantiomers or diastereoisomers in relation to the stereochemistry at those positions.

Medical Uses

As indicated herein, the compounds of the invention, and therefore compositions and kits comprising the same, are useful as pharmaceuticals.

Thus, according to a second aspect of the invention there is provided a compound of the first aspect of the invention, as hereinbefore defined (i.e. a compound as defined in the first aspect of the invention, including all embodiments and particular features thereof), for use as a pharmaceutical (or for use in medicine).

For the avoidance of doubt, references to compounds as defined in the first aspect of the invention will include references to compounds of formula I (including all embodiments thereof) and pharmaceutically acceptable salts thereof.

Similarly, in a further embodiment of the second aspect of the invention, the compound of the invention is not 4-ethylpiperidin-2-yl(phenyl)methanol, or a pharmaceutically acceptable salt thereof (e.g. the HCl).

In further embodiments of the second aspect of the invention, the compound of the invention is not (or, is also not) 4-(hydroxy(piperidin-2-yl)methyl)benzene-1,2-diol, or a pharmaceutically acceptable salt thereof.

As indicated herein, the compounds of the invention may be of particular use in treating hyperglycaemia or a disorder characterized by hyperglycaemia.

Thus, in a third aspect of the invention, there is provided a compound of the first aspect of the invention, as hereinbefore defined, for use in the treatment of hyperglycaemia or a disorder characterized by hyperglycaemia.

In an alternative third aspect of the invention, there is provided the use of a compound of formula I, or a pharmaceutically acceptable salt thereof, in the manufacture of a medicament for use in the treatment of hyperglycaemia or a disorder characterized by hyperglycaemia.

In a further alternative third aspect of the invention, there is provided a method of treating hyperglycaemia or a disorder characterized by hyperglycaemia comprising administering to a patient in need thereof a therapeutically effective amount of a compound of formula I, or a pharmaceutically acceptable salt thereof.

For the avoidance of doubt, the term "hyperglycaemia" as used herein will be understood by those skilled in the art to refer to a condition wherein an excessive amount of glucose circulates in blood plasma of the subject experiencing the same. In particular, it may refer to a subject (e.g a human subject) having blood glucose levels higher than about 10.0 mmol/L (such as higher than about 11.1 mmol/L, e.g. higher than about 15 mmol/L), although it may also refer to a subject (e.g a human subject) having blood glucose levels higher than about 7 mmol/L for an extended period of time (e.g. for greater than 24 hours, such as for greater than 48 hours).

The skilled person will understand that references to the treatment of a particular condition (or, similarly, to treating that condition) take their normal meanings in the field of medicine. In particular, the terms may refer to achieving a reduction in the severity of one or more clinical symptom associated with the condition. For example, in the case of type 2 diabetes, the term may refer to achieving a reduction of blood glucose levels. In particular embodiments, in the case of treating hyperglycaemia or conditions characterised by hyperglycaemia, the term may refer to achieving a reduction of blood glucose levels (for example, to or below about 10.0 mmol/mL (e.g. to levels in the range of from about 4.0 mmol/L to about 10.0 mmol/L), such as to or below about 7.5 mmol/mL (e.g. to levels in the range of from about 4.0 mmol/L to about 7.5 mmol/L) or to or below about 6 mmol/mL (e.g. to levels in the range of from about 4.0 mmol/L to about 6.0 mmol/L)).

As used herein, references to patients will refer to a living subject being treated, including mammalian (e.g. human) patients. Thus, in particular embodiments of the first aspect of the invention, the treatment is in a mammal (e.g. a human).

As used herein, the term therapeutically effective amount will refer to an amount of a compound that confers a therapeutic effect on the treated patient. The effect may be objective (i.e. measurable by some test or marker) or subjective (i.e. the subject gives an indication of and/or feels an effect).

Although compounds of the first aspect of the invention may possess pharmacological activity as such, certain pharmaceutically-acceptable (e.g. "protected") derivatives of compounds of the invention may exist or be prepared which may not possess such activity, but may be administered parenterally or orally and thereafter be metabolised in the body to form compounds of the invention. Such compounds (which may possess some pharmacological activity, provided that such activity is appreciably lower than that of the active compounds to which they are metabolised) may therefore be described as "prodrugs" of compounds of the invention.

As used herein, references to prodrugs will include compounds that form a compound of the invention, in an experimentally-detectable amount, within a predetermined time, following enteral or parenteral administration (e.g. oral or parenteral administration). All prodrugs of the compounds of the first aspect of the invention are included within the scope of the invention.

For the avoidance of doubt, the compounds of the first aspect of the invention are useful because they possess pharmacological activity, and/or are metabolised in the body following oral or parenteral administration to form compounds that possess pharmacological activity. In particular, as described herein, compounds of the first aspect of the invention are useful in the treatment of hyperglycaemia or disorders characterized by hyperglycaemia (such as type 2 diabetes), which terms will be readily understood by one of skill in the art (as described herein).

In a particular embodiment, the treatment is of a disorder (which may also be referred to as a condition or disease) characterised by hyperglycaemia.

In particular embodiments, compounds of the invention (i.e. compounds of formula I, including all embodiments thereof) are for use in the treatment of type 2 diabetes (or useful in the manufacture of a medicament for such treatment, or useful in a method for such treatment, as described herein).

In particular embodiments of the first aspect of the invention, the disorder is type 2 diabetes, such as type 2 diabetes of a sub-type selected from the list consisting of maturity-onset diabetes in the young (MODY), ketosis-prone diabetes in adults, latent autoimmune diabetes of adults (LADA), and gestational diabetes.

In further particular embodiments, the treatment of type 2 diabetes is in a non-obese patient.

For the avoidance of doubt, the skilled person will understand that patients with a Body Mass Index (BMI) of greater than 30 are considered to be obese.

In particular embodiments, the treatment may be of hyperglycaemia in a patent who is at risk of developing type 2 diabetes, which condition may be defined as pre-diabetes. Thus, compounds of the invention may be useful in the prevention of type 2 diabetes (e.g. in a patient having pre-diabetes).

As used herein, the term prevention (and, similarly, preventing) includes references to the prophylaxis of the disease or disorder (and vice-versa). As such, references to prevention may also be references to prophylaxis, and vice versa. In particular, the term may refer to achieving a reduction in the likelihood of the patient (or healthy subject) developing the condition (for example, at least a 10% reduction, such as at least a 20%, 30% or 40% reduction, e.g. at least a 50% reduction).

In more particular embodiments, the type 2 diabetes is characterised by the patient displaying severe insulin resistance (SIR).

In further embodiments, the treatment may be of hyperglycaemia in a patient having type 1 diabetes. Thus, compounds of the invention may be useful in the treatment of hyperglycaemia in type 1 diabetes.

The skilled person will understand that compounds of the invention may be useful in treating hyperglycaemia in patients having impaired insulin production, such as in patients having cystic fibrosis. Thus, in further embodiments, the disorder characterized by hyperglycaemia is cystic fibrosis-related diabetes.

In particular embodiments that may be mentioned, the disorder characterised by hyperglycaemia is (or is characterized by) severe insulin resistance (SIR), which may be understood by those in the art to refer to disorders wherein typically the subject has normal, or in some cases increased, insulin production but significantly reduced insulin sensitivity. In particular instances, such patients may be non-obese (e.g. being of a healthy weight). Thus, in particular embodiments, such treatments are performed in patients who are not defined as being obese (e.g. in patients who are defined as being of a healthy weight).

For example, SIR may be identified in a patient based in said patient having fasting insulin>150 pmol/L and/or a peak insulin on glucose tolerance testing of >1,500 pmol/L, particularly in individuals with a BMI<30 kg/m$^2$ (which patient may otherwise have normal glucose tolerance).

More particularly, SIR may be characterised by the patient having no significant response to the presence of insulin, which may result from a defect (e.g. a genetic defect) in the function of the insulin receptor.

Particular disorders that may be characterised by SIR include: Rabson-Mendenhall syndrome, Donohue's syndrome (leprechaunism), Type A and Type B syndromes of insulin resistance, the HAIR-AN (hyperandrogenism, insulin resistance, and acanthosis nigricans) syndromes, pseudoacromegaly, and lipodystrophy.

More particular disorders that may be characterised by SIR include Donohue's syndrome and Type A syndrome of insulin resistance and, yet more particularly, Rabson-Mendenhall syndrome.

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of type 2 diabetes, such as treatment with one or more other therapeutic agent that is useful in the treatment of type 2 diabetes as known to those skilled in the art, such as therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that:

(i) are capable of reducing blood sugar levels; and/or (ii) are insulin sensitizers; and/or (iii) enhance insulin release, all of which are described herein below.

In alternative embodiments, compounds of the first aspect of the invention (i.e. compounds of the invention) may be useful in the treatment of a non-alcoholic fatty liver disease (NAFLD).

Non-alcoholic fatty liver disease (NAFLD) is defined by excessive fat accumulation in the form of triglycerides (steatosis) in the liver (designated as an accumulation of greater than 5% of hepatocytes histologically). It is the most common liver disorder in developed countries (for example, affecting around 30% of US adults) and most patients are asymptomatic. If left untreated, the condition may progressively worsen and may ultimately lead to cirrhosis of the liver. NAFLD is particularly prevalent in obese patents, with around 80% thought to have the disease.

A sub-group of NAFLD patients (for example, between 2 and 5% of US adults) exhibit liver cell injury and inflammation in addition to excessive fat accumulation. This condition, designated as non-alcoholic steatohepatitis (NASH), is virtually indistinguishable histologically from alcoholic steatohepatitis. While the simple steatosis seen in NAFLD does not directly correlate with increased short-term morbidity or mortality, progression of this condition to NASH dramatically increases the risks of cirrhosis, liver failure and hepatocellular carcinoma. Indeed, NASH is now considered to be one of the main causes of cirrhosis (including cryptogenic cirrhosis) in the developed world.

The exact cause of NASH has yet to be elucidated, and it is almost certainly not the same in every patient. It is most closely related to insulin resistance, obesity, and the metabolic syndrome (which includes diseases related to diabetes mellitus type 2, insulin resistance, central (truncal) obesity, hyperlipidaemia, low high-density lipoprotein (HDL) cholesterol, hypertriglyceridemia, and hypertension). However, not all patients with these conditions have NASH, and not all patients with NASH suffer from one of these conditions. Nevertheless, given that NASH is a potentially fatal condition, leading to cirrhosis, liver failure and hepatocellular carcinoma, there exists a clear need for an effective treatment.

In particular embodiments, compounds of the invention (i.e. compounds of formula I, including all embodiments thereof) are for use in the treatment of a non-alcoholic fatty liver disease (or useful in the manufacture of a medicament for such treatment, or useful in a method for such treatment, as described herein).

The process by which the triglyceride fat accumulates in liver cells is called steatosis (i.e. hepatic steatosis). The skilled person will understand that the term "steatosis" encompasses the abnormal retention of fat (i.e. lipids) within a cell. Thus, in particular embodiments of the first aspect of the invention, the treatment or prevention is of a fatty liver disease which is characterized by steatosis.

During steatosis, excess lipids accumulate in vesicles that displace the cytoplasm of the cell. Over time, the vesicles can grow large enough to distort the nucleus, and the condition is known as macrovesicular steatosis. Otherwise, the condition may be referred to as microvesicular steatosis. Steatosis is largely harmless in mild cases; however, large accumulations of fat in the liver can cause significant health issues. Risk factors associated with steatosis include diabetes mellitus, protein malnutrition, hypertension, obesity, anoxia, sleep apnea and the presence of toxins within the cell.

As described herein, fatty liver disease is most commonly associated with alcohol or a metabolic syndrome (for example, diabetes, hypertension, obesity or dyslipidemia). Therefore, depending on the underlying cause, fatty liver disease may be diagnosed as alcohol-related fatty liver disease or non-alcoholic fatty liver disease (NAFLD).

Particular diseases or conditions that are associated with fatty liver disease that are not related to alcohol include metabolic conditions such as diabetes, hypertension, obesity, dyslipidemia, abetalipoproteinemia, glycogen storage diseases, Weber-Christian disease, acute fatty liver of pregnancy, and lipodystrophy. Other non-alcohol related factors related to fatty liver diseases include malnutrition, total parenteral nutrition, severe weight loss, refeeding syndrome, jejunoileal bypass, gastric bypass, polycystic ovary syndrome and diverticulosis.

The compounds of the invention have been found to be particularly useful in the treatment or prevention of NAFLD, which may be referred to as a fatty liver disease which is not alcohol related. A fatty liver disease which is "not alcohol related" may be diagnosed wherein alcohol consumption of the patient is not considered to be a main causative factor. A typical threshold for diagnosing a fatty liver disease as "not alcohol related" is a daily consumption of less than 20 g for female subjects and less than 30 g for male subjects.

If left untreated, subjects suffering from fatty liver disease may begin to experience inflammation of the liver (hepatitis). It has been postulated that one of the possible causes of this inflammation may be lipid peroxidative damage to the membranes of the liver cells. Inflammation of a fatty liver can lead to a number of serious conditions and it is therefore desirable to treat or prevent fatty liver disease before inflammation occurs. Thus, in particular embodiments of the first aspect of the invention, the treatment or prevention is of a NAFLD which is associated with inflammation.

Non-alcoholic steatohepatitis (NASH) is the most aggressive form of NAFLD, and is a condition in which excessive fat accumulation (steatosis) is accompanied by inflammation of the liver. If advanced, NASH can lead to the development of scar tissue in the liver (fibrosis) and, eventually, cirrhosis. As described above, the compounds of the invention have been found to be useful in the treatment or prevention of NAFLD, particularly when accompanied by inflammation of the liver. It follows that the compounds of the invention are also useful in the treatment or prevention of NASH. Therefore, in a further embodiment of the first aspect of the invention, the treatment or prevention is of non-alcoholic steatohepatitis (NASH).

The skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of a fatty liver disease, as described herein, such as treatment with one or more other therapeutic agent that is useful in the treatment of a fatty liver disease as known to those skilled in the art; for example, therapies comprising requiring the patient to undergo a change of diet and/or undertake exercise regiments, and/or surgical procedures designed to promote weight loss (such as gastric band surgery).

In particular, treatment with compounds of the invention may be performed in combination with (e.g. in a patient who is also being treated with) one or more (e.g. one) additional compounds (i.e. therapeutic agents) that are capable of reducing the level of fat (e.g. triglycerides) in the liver.

References to treatment of a fatty liver disease may refer to achieving a therapeutically significant reduction of fat (e.g. triglycerides levels) in liver cells (such as a reduction of at least 5% by weight, e.g. a reduction of at least 10%, or at least 20% or even 25%).

Pharmaceutical Compositions

As described herein, compounds of the first and, therefore, the second and third aspects of the invention are useful as pharmaceuticals. Such compounds may be administered alone or may be administered by way of known pharmaceutical compositions/formulations.

In a fourth aspect of the invention, there is provided a pharmaceutical composition comprising a compound as defined in the second or third aspect of the invention, and optionally one or more pharmaceutically acceptable adjuvant, diluent and/or carrier.

The skilled person will understand that references herein to compounds of the first aspect of the invention being for particular uses (and, similarly, to uses and methods of use relating to compounds of the invention) may also apply to pharmaceutical compositions comprising compounds of the invention as described herein.

In a fifth aspect of the invention, there is provided a pharmaceutical composition for use in the treatment of hyperglycaemia or a disorder characterized by hyperglycaemia (as defined herein, such as type 2 diabetes) comprising a compound as defined in the first aspect of the invention, and optionally one or more pharmaceutically acceptable adjuvant, diluent and/or carrier.

In an alternative fifth aspect of the invention, there is provided a pharmaceutical composition for use in the treatment or prevention of a non-alcoholic fatty liver disease, as defined herein.

In an alternative fifth aspect of the invention, there is provided a pharmaceutical composition for use in the treatment or prevention of a non-alcoholic fatty liver disease, as defined herein.

The skilled person will understand that compounds of the first (and, therefore, second and third) aspect of the invention may act systemically and/or locally (i.e. at a particular site).

The skilled person will understand that compounds and compositions as described in the first to fifth aspects of the invention will normally be administered orally, intravenously, subcutaneously, buccally, rectally, dermally, nasally, tracheally, bronchially, sublingually, intranasally, topically, by any other parenteral route or via inhalation, in a pharmaceutically acceptable dosage form. Pharmaceutical compositions as described herein will include compositions in the form of tablets, capsules or elixirs for oral administration, suppositories for rectal administration, sterile solutions or suspensions for parenteral or intramuscular administration, and the like. Alternatively, particularly where such compounds of the invention act locally, pharmaceutical compositions may be formulated for topical administration.

Thus, in particular embodiments of the fourth and fifth aspects of the invention, the pharmaceutical formulation is provided in a pharmaceutically acceptable dosage form, including tablets or capsules, liquid forms to be taken orally or by injection, suppositories, creams, gels, foams, inhalants (e.g. to be applied intranasally), or forms suitable for topical administration. For the avoidance of doubt, in such embodiments, compounds of the invention may be present as a solid (e.g. a solid dispersion), liquid (e.g. in solution) or in other forms, such as in the form of micelles.

For example, in the preparation of pharmaceutical formulations for oral administration, the compound may be mixed with solid, powdered ingredients such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or compressed into tablets.

Soft gelatin capsules may be prepared with capsules containing one or more active compounds (e.g. compounds of the first and, therefore, second and third aspects of the invention, and optionally additional therapeutic agents), together with, for example, vegetable oil, fat, or other suitable vehicle for soft gelatin capsules. Similarly, hard gelatine capsules may contain such compound(s) in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the compound(s) mixed with a neutral fat base; (ii) in the form of a gelatin rectal capsule which contains the active substance in a mixture with a vegetable oil, paraffin oil, or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions, containing the compound(s) and the remainder of the formulation consisting of sugar or sugar alcohols, and a mixture of ethanol, water, glycerol, propylene glycol and polyethylene glycol. If desired, such liquid preparations may contain colouring agents, flavouring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of the compound(s) in a pharmaceutically acceptable solvent. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The skilled person will understand that compounds of the invention, and pharmaceutically-acceptable salts thereof, may be administered (for example, as formulations as described hereinabove) at varying doses, with suitable doses being readily determined by one of skill in the art. Oral, pulmonary and topical dosages (and subcutaneous dosages, although these dosages may be relatively lower) may range from between about 0.01 µg/kg of body weight per day (µg/kg/day) to about 200 µg/kg/day, preferably about 0.01 to about 10 µg/kg/day, and more preferably about 0.1 to about 5.0 µg/kg/day. For example, when administered orally, treatment with such compounds may comprise administration of a formulations typically containing between about 0.01 µg to about 2000 mg, for example between about 0.1 µg to about 500 mg, or between 1 µg to about 100 mg (e.g. about 20 µg to about 80 mg), of the active ingredient(s). When administered intravenously, the most preferred doses will range from about 0.001 to about 10 µg/kg/hour during constant rate infusion. Advantageously, treatment may comprise administration of such compounds and compositions in a single daily dose, or the total daily dosage may be administered in divided doses of two, three or four times daily (e.g. twice daily with reference to the doses described herein, such as a dose of 10 mg, 20 mg, 30 mg or 40 mg twice daily, or 10 µg, 20 µg, 30 µg or 40 µg twice daily).

In any event, the skilled person (e.g. the physician) will be able to determine the actual dosage which will be most suitable for an individual patient, which is likely to vary with the route of administration, the type and severity of the condition that is to be treated, as well as the species, age, weight, sex, renal function, hepatic function and response of the particular patient to be treated. The above-mentioned dosages are exemplary of the average case; there can, of course, be individual instances where higher or lower dosage ranges are merited, and such are within the scope of this invention.

As described herein above, the skilled person will understand that treatment with compounds of the first aspect of the invention may further comprise (i.e. be combined with) further (i.e. additional/other) treatment(s) for the same condition. In particular, treatment with compounds of the invention may be combined with other means for the treatment of hyperglycaemia or a disorder characterized by hyperglycaemia (as defined herein, such as type 2 diabetes), such as treatment with one or more other therapeutic agent that is useful in the treatment of hyperglycaemia or a disorder characterized by hyperglycaemia (as defined herein, such as type 2 diabetes).

In particular embodiments of the fourth and fifth aspects of the invention, the pharmaceutical composition may further comprise one or more additional (i.e. other) therapeutic agent.

In more particular embodiments, the one or more additional therapeutic agent is an agent for the treatment of type 2 diabetes as known to those skilled in the art, such as metformin, sulfonylureas (e.g. carbutamide, acetohexamide, chlorpropamide, tolbutamide. glipizide (glucotrol), gliclazide, glibenclamide, glyburide (Micronase), glibornuride, gliquidone, glisoxepide, glyclopyramide, glimepiride (Amaryl), glimiprime, JB253 or JB558), thiazolidinediones (e.g. pioglitazone, rosiglitazone (Avandia), lobeglitazone (Duvie) and troglitazone (Rezulin)), dipeptidyl peptidase-4 inhibitors (e.g. sitagliptin, vildagliptin, saxagliptin, linagliptin, anagliptin, teneligliptin, alogliptin, trelagliptin, gemigliptin, dutogliptin and omarigliptin), SGLT2 inhibitors (e.g. dapagliflozin, empagliflozin, canagliflozin, ipragliflozin, tofogliflozin, sergliflozin etabonate, remogliflozin etabonate, and ertugliflozin), and glucagon-like peptide-1 (GLP-1) analogues.

The skilled person will understand that combinations of therapeutic agents may also described as a combination product and/or provided as a kit-of-parts.

In a sixth aspect of the invention, there is provided a combination product comprising:

(A) a compound as defined in the first aspect of the invention; and (B) one or more additional therapeutic agent,
wherein each of components (A) and (B) is formulated in admixture, optionally with one or more a pharmaceutically-acceptable adjuvant, diluent or carrier.

In a seventh aspect of the invention, there is provided a kit-of-parts comprising:

(a) a compound as defined in the first (or second and/or third) aspect of the invention, (or a pharmaceutical composition comprising the same) or a pharmaceutical composition as defined in the fourth or fifth aspect of the invention; and (b) one or more other therapeutic agent, optionally in admixture with one or more pharmaceutically-acceptable adjuvant, diluent or carrier, which components (a) and (b) are each provided in a form that is suitable for administration in conjunction with the other.

In particular embodiments (e.g. of the sixth and seventh aspects of the invention), the additional therapeutic agent is a therapeutic agent that is useful for the treatment of hyperglycaemia or a disorder characterized by hyperglycaemia (e.g. type 2 diabetes), as known to those skilled in the art (such as those described herein).

For example, in particular embodiments of the fourth to fifth aspects of the invention, the additional therapeutic agent is an agent that:

(i) is capable of reducing blood sugar levels; and/or
(ii) is an insulin sensitizer; and/or
(iii) is able to enhance insulin release, which agents will be readily identified by those skilled in the art and include, in particular, such therapeutic agents that are commercially available (e.g. agents that the subject of a marketing authorization in one or more territory, such as a European or US marketing authorization).

The skilled person will understand that references to therapeutic agents capable of reducing blood glucose levels may refer to compounds capable of reducing levels of blood by at least 10% (such as at least 20%, at least 30% or at least 40%, for example at least 50%, at least 60%, at least 70% or at least 80%, e.g. at least 90%) when compared to the blood glucose levels prior to treatment with the relevant compound.

In alternative embodiments of the sixth and seventh aspects of the invention, the additional therapeutic agent is an agent for the treatment or prevention of a non-alcoholic fatty liver disease (such as NASH), which agents will be readily identified by those skilled in the art and include, in particular, such therapeutic agents that are commercially available (e.g. agents that the subject of a marketing authorization in one or more territory, such as a European or US marketing authorization).

Preparation of Compounds/Compositions

Pharmaceutical compositions/formulations, combination products and kits as described herein may be prepared in accordance with standard and/or accepted pharmaceutical practice.

Thus, in a further aspect of the invention there is provided a process for the preparation of a pharmaceutical composition/formulation, as hereinbefore defined, which process comprises bringing into association a compound of the invention, as hereinbefore defined, with one or more pharmaceutically-acceptable adjuvant, diluent or carrier.

In further aspects of the invention, there is provided a process for the preparation of a combination product or kit-of-parts as hereinbefore defined, which process comprises bringing into association a compound of the invention, as hereinbefore defined, or a pharmaceutically acceptable salt thereof with the other therapeutic agent that is useful in the treatment of hyperglycaemia or a disorder characterized by hyperglycaemia (e.g. type 2 diabetes), and at least one pharmaceutically-acceptable adjuvant, diluent or carrier.

As used herein, references to bringing into association will mean that the two components are rendered suitable for administration in conjunction with each other.

Thus, in relation to the process for the preparation of a kit of parts as hereinbefore defined, by bringing the two components "into association with" each other, we include that the two components of the kit of parts may be:

(i) provided as separate formulations (i.e. independently of one another), which are subsequently brought together for use in conjunction with each other in combination therapy; or (ii) packaged and presented together as separate components of a "combination pack" for use in conjunction with each other in combination therapy.

Compounds as defined in the first aspect of the invention (i.e. compounds of the invention) may be prepared in accordance with techniques that are well known to those skilled in the art, such as those described in the examples provided hereinafter.

For example, there is provided a process for the preparation of a compound of formula I, or a pharmaceutically acceptable salt thereof, as defined in the first aspect of the invention, which process comprises:

(i) reaction of a compound of formula II

wherein m, $R^1$ and ring A are as defined herein above, and wherein $M^1$ represents a suitable metal or metal halide (e.g. Li), with a compound of formula III

wherein n and X are as defined herein above, under conditions known to those skilled in the art, such as in a suitable solvent (e.g. diethyl ether) and optionally in the presence of a suitable base (such as TMEDA);

(ii) reaction of a compound of formula IV

wherein n and X are as defined herein, and wherein $M^2$ represents a suitable metal or metal halide (e.g. a metal bromide, such as MgBr), with a compound of formula V

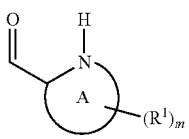

wherein m, R¹ and ring A are as defined herein, under conditions known to those skilled in the art, such as in a suitable solvent (e.g. THF);

(iii) for compounds wherein at least one X is present and represents —OH, deprotection of a compound of formula VI

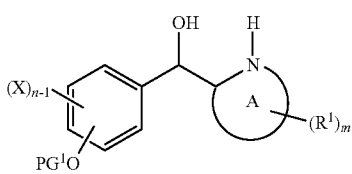

(VI)

wherein n, m and R¹ are as defined hereinabove, PG¹ represents a suitable protecting group as known to those skilled in the art (e.g. benzyl) under conditions known to those skilled in the art (for example, in the case of a benzyl protecting group, in the presence of hydrogen and a suitable catalyst or a suitable acid; in the case of alkyl, such as methyl, in the presence of BBr₃, HBr or alkyl sulfides);

(iv) for compounds wherein at least one X is present and represents —NH₂, deprotection of a compound of formula VII

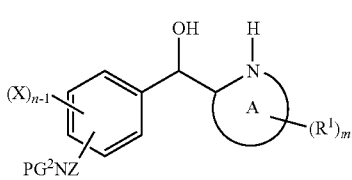

(VII)

wherein n, m, X and R¹ are as defined hereinabove, and Z represents H or PG³, wherein PG² and PG³ each represents a suitable protecting group as known to those skilled in the art (e.g. a carbamate protecting group, such as tert-butyloxycarbonyl (Boc), fluorenylmethyloxycarbonyl (Fmoc) or carboxybenzyl (Cbz), or an amide protecting group, such as acetyl and benzoyl), under conditions known to those skilled in the art (for example in the case of Boc, in the presence of a suitable acid (e.g. trifluoroacetic acid or HCl);

(v) for compounds wherein at least one X is present and represents NH₂, reduction of a compound of formula VIII

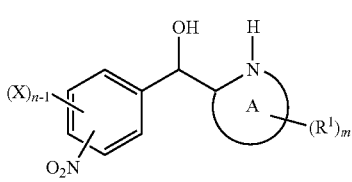

(VIII)

wherein n, X and R¹ are as defined hereinabove, under conditions known to those skilled in the art (for example, by hydrogenation, such as hydrogenation using hydrogen gas and a suitable catalyst as known to those skilled in the art (e.g. Pd—C, PtO₂, Raney-Nickel), Fe or Zn in acidic media (e.g. AcOH), borohydrides together with a suitable catalyst (e.g. NaBH₄ and Raney-Nickel), or agents such as SnCl₂, TiCl₃, SmI₂, and the like). Those skilled in the art will understand that certain functional groups, such as the essential —OH and/or the —NHR¹ groups) may need to be protected (and deprotected) one or more times during the reaction, which protections (and deprotections) may be performed using techniques known to those skilled in the art;

(vi) deprotection of a compound of formula IX

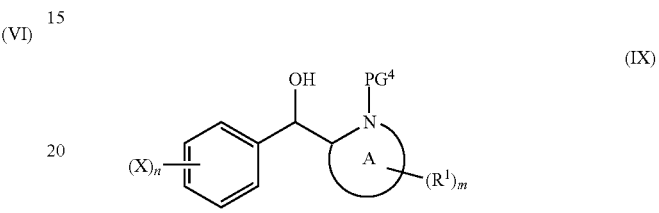

(IX)

wherein n, m, X and R¹ are as defined hereinabove, and PG⁴ represents a suitable protecting group as known to those skilled in the art (e.g. a carbamate protecting group, such as tert-butyloxycarbonyl (Boc), fluorenylmethyloxycarbonyl (Fmoc) or carboxybenzyl (Cbz), or an amide protecting group, such as acetyl and benzoyl), under conditions known to those skilled in the art (for example in the case of Boc, in the presence of a suitable acid (e.g. trifluoroacetic acid or HCl).

Compounds of formulae II, III, IV, V, VI, VII, VIII and IX are either commercially available, are known in the literature, or may be obtained either by analogy with the processes described herein, or by conventional synthetic procedures, in accordance with standard techniques, from available starting materials (e.g. appropriately substituted benzaldehydes, styrenes or phenacyl bromides (or phenacylchloride, and the like) using appropriate reagents and reaction conditions. In this respect, the skilled person may refer to inter alia "Comprehensive Organic Synthesis" by B. M. Trost and I. Fleming, Pergamon Press, 1991. Further references that may be employed include "Science of Synthesis", Volumes 9-17 (Hetarenes and Related Ring Systems), Georg Thieme Verlag, 2006.

The substituents X and R¹, as hereinbefore defined, may be modified one or more times, after or during the processes described above for preparation of compounds of formula I by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. The precursor groups can be changed to a different such group, or to the groups defined in formula I, at any time during the reaction sequence. The skilled person may also refer to "Comprehensive Organic Functional Group Transformations" by A. R. Katritzky, O. Meth-Cohn and C. W. Rees, Pergamon Press, 1995 and/or "Comprehensive Organic Transformations" by R. C. Larock, Wiley-VCH, 1999.

Such compounds may be isolated from their reaction mixtures and, if necessary, purified using conventional techniques as known to those skilled in the art. Thus, processes for preparation of compounds of the invention as described herein may include, as a final step, isolation and optionally purification of the compound of the invention (e.g. isolation and optionally purification of the compound of formula I).

The skilled person will understand that compounds of formula I having specific stereochemistry may be provided by reacting suitable starting materials having the required stereochemistry in processes as described herein. Further, the skilled person will understand that suitable starting materials having the required stereochemistry may be prepared by analogy with the processes described herein.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999).

Compounds as described herein (in particular, compounds as defined in the first and, therefore, second and third aspects of the invention) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise. In particular, such compounds may have the advantage that they are more efficacious and/or exhibit advantageous properties in vivo.

Without wishing to be bound by theory, compounds as described herein are thought to be potent agonists of the $\beta_2$-adrenergic receptor, which allows for increased glucose uptake in skeletal muscle cells.

In addition, compounds as described herein are thought to be agonists of the $\beta_2$-adrenergic receptor without (or with only a minimal effect in) inducing cAMP production. It is thought that this allows for the increased glucose uptake in skeletal muscle cells with lower levels of side effects than would result from other treatments. Further, combining compounds as described herein with therapeutic agents that are able to decrease blood glucose levels is thought to provide an effective combination therapy.

EXAMPLES

The present invention is illustrated by way of the following examples.

Chemicals and reagents were obtained from commercial suppliers and were used as received unless otherwise stated. All reactions involving moisture sensitive reagents were performed in oven or flame dried glassware under a positive pressure of nitrogen or argon.

Abbreviations

Abbreviations as used herein will be known to those skilled in the art. In particular, the following abbreviations may be used herein.

AcOH acetic acid
aq aqueous
atm atmosphere
Boc$_2$O di-tert-butyldicarbonate
BuLi butyl lithium
DIPEA N,N-diisopropylethylamine
DMAP 4-dimethylaminopyridine
DMF dimethylformamide
DMSO dimethylsulfoxide
eq equivalent
EtOAc ethyl acetate
HMPA hexamethylphosphoramide
MeCN acetonitrile
MeOH methanol
Pd—C palladium on carbon
rt room temperature
sat saturated
TFA trifluoroacetic acid
THF tetrahydrofuran
TMEDA N,N,N',N'-tetramethylethylenediamine

EXAMPLE COMPOUNDS

In the event that there is a discrepancy between nomenclature and the structure of compounds as depicted graphically, it is the latter that presides (unless contradicted by any experimental details that may be given and/or unless it is clear from the context).

Example 1: (R)-(3-Fluorophenyl)((2R,6R)-6-propylpiperidin-2-yl)methanol

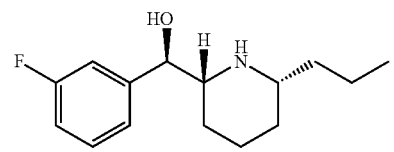 [SMILES: CCC[C@@H]1CCC[C@H]([C@H](O)c2cccc(F)c2)N1]

(a) tert-Butyl (R)-2-propylpiperidine-1-carboxylate

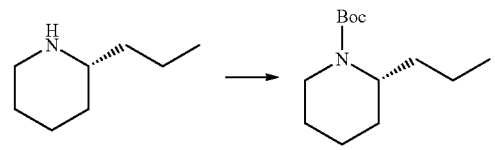

DIPEA (2.2 mL, 12.7 mmol) was added to a solution of (R)-(+)-coniine hydrochloride (0.52 g, 3.2 mmol) in CH$_2$Cl$_2$ (20 mL) at rt. After 10 min Boc$_2$O (0.76 g, 3.5 mmol) was added and the mixture was stirred at rt for 18 h. H$_2$O was added and the mixture was extracted with CH$_2$Cl$_2$. The combined extracts were dried over Na$_2$SO$_4$, concentrated and purified by chromatography to give the sub-title compound (0.72 g, 3.15 mmol, 99%).

(b) tert-Butyl (2R,6R)-2-formyl-6-propylpiperidine-1-carboxylate

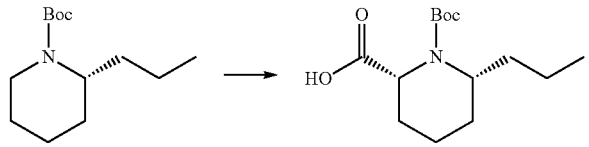 [SMILES: CCC[C@@H]1CCCCN1C(=O)OC(C)(C)C ; CCC[C@@H]1CCC[C@H](C(=O)O)N1C(=O)OC(C)(C)C]

sec-BuLi (1.3 M in cyclohexane, 1.6 mL, 2.1 mmol) was added dropwise to a stirred mixture of tert-butyl (R)-2-propylpiperidine-1-carboxylate (270 mg, 1.2 mmol), TMEDA (0.39 mL, 2.6 mmol) and Et$_2$O (5 mL) at −78° C. The mixture was allowed to warm to −40° C. over 1 h, kept at that temperature for 1 h and cooled to −78° C. DMF (0.92 mL, 11.9 mmol) was added in one portion and the mixture was slowly allowed to warm to −40° C. and stirred at that temperature for 1 h. H$_2$O (4 mL) was added and the mixture was allowed to warm to rt and extracted with Et$_2$O. The combined extracts were dried over Na$_2$SO$_4$ and concentrated. MeOH (6 mL) and K$_2$CO$_3$ were added to the residue and the mixture was stirred at rt for 2 h and poured into NH$_4$Cl (aq, sat). The mixture was extracted with CH$_2$Cl$_2$ and the combined extracts dried over Na$_2$SO$_4$, concentrated and purified by chromatography to give the sub-title compound (0.20 g, 0.78 mmol, 66%).

(c) tert-Butyl (2R,6R)-2-((R)-(3-fluorophenyl)(hydroxy)methyl)-6-propylpiperidine-1-carboxylate

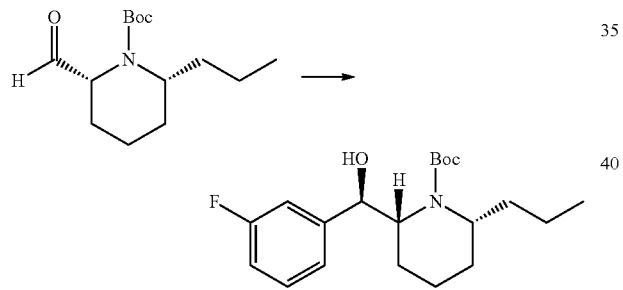

Fluorophenylmagnesium bromide (0.94 mmol in THF, prepared from 1-bromo-3-fluorobenzene and Mg) was added to a solution of tert-butyl (2R,6R)-2-formyl-6-propylpiperidine-1-carboxylate (0.20 mg, 0.78 mmol) in THF (5 mL) at −20° C. The mixture was stirred at −20° C. for 20 min and NH$_4$Cl (aq, sat, 5 mL) was added. The mixture was extracted with EtOAc and the combined extracts dried over Na$_2$SO$_4$, concentrated and purified by chromatography to give the sub-title compound (146 mg, 0.42 mmol, 53%).

(d) (R)-(3-Fluorophenyl)((2R,6R)-6-propylpiperidin-2-yl)methanol

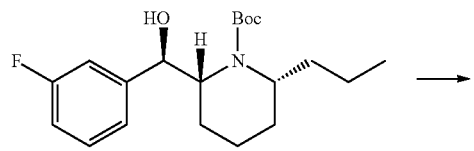

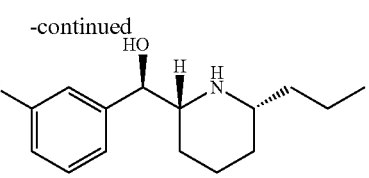

NaOH (0.64 mg, 16 mmol) in H$_2$O (0.5 mL) was added to a solution of tert-butyl (2R,6R)-2-((R)-(3-fluorophenyl)(hydroxy)methyl)-6-propylpiperidine-1-carboxylate (140 mg, 0.40 mmol) in EtOH (1 mL). The mixture was heated in a sealed vial at 120° C. for 20 h, cooled and concentrated. HCl (aq, 1 M) was added to adjust the pH to 7, and the mixture was extracted with EtOAc and the combined extracts dried over Na$_2$SO$_4$, concentrated and purified by chromatography to give the title compound (70 mg, 0.28 mmol, 70%).

$^1$H NMR (400 MHz, CDCl$_3$): δ 7.33-7.27 (m, 1H), 7.13-7.05 (m, 2H), 7.00-6.94 (m, 1H), 4.41 (d, J=7.2 Hz, 1H), 2.86 (br s, 2H), 2.73-2.65 (m, 1H), 2.55-2.47 (m, 1H), 1.81-1.74 (m, 1H), 1.71-1.63 (m, 1H), 1.43-1.27 (m, 5H), 1.27-1.14 (m, 2H), 1.09-0.97 (m, 1H), 0.90 (t, J=7.1 Hz, 3H).

Example 2: (R)-(3-Fluorophenyl)((2R,6S)-6-propylpiperidin-2-yl)methanol

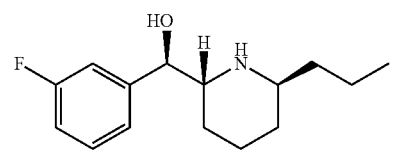 [SMILES: CCC[C@H]1CCC[C@H]([C@H](O)c2cccc(F)c2)N1]

(a) tert-Butyl (S)-2-propylpiperidine-1-carboxylate

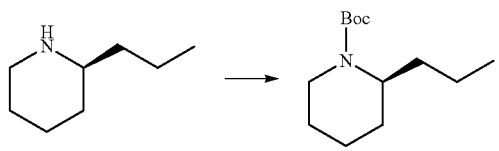

The sub-title compound was prepared in accordance with the procedure in Example 1, Step (a) from (S)-(+)-coniine hydrochloride.

(b) tert-Butyl (2R,6S)-2-((R)-(3-fluorophenyl)(hydroxy)methyl)-6-propylpiperidine-1-carboxylate

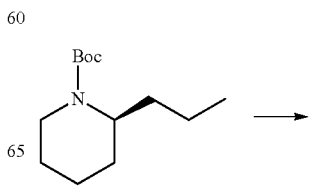

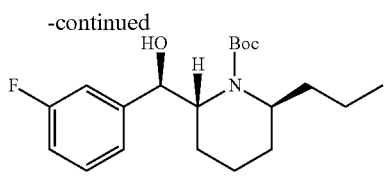

sec-BuLi (1.3 M in cyclohexane, 1.6 mL, 2.1 mmol) was added dropwise to a stirred mixture of tert-butyl (S)-2-propylpiperidine-1-carboxylate (270 mg, 1.2 mmol), TMEDA (0.39 mL, 2.6 mmol) and Et$_2$O (5 mL) at −78° C. The mixture was allowed to warm to −30° C. over 1 h, kept at that temperature for 1 h and cooled to −78° C. 3-fluorobenzaldehyde (0.12 mL, 1.1 mmol) was added dropwise and the mixture was stirred at −78° C. for 30 min. H$_2$O (4 mL) was added and the mixture was allowed to warm to rt and extracted with Et$_2$O. The combined extracts were dried over Na$_2$SO$_4$ and concentrated. The residue was purified by chromatography to give the sub-title compound (164 mg, 0.47 mmol, 42%).

(c) (R)-(3-Fluorophenyl)((2R,6S)-6-propylpiperidin-2-yl)methanol

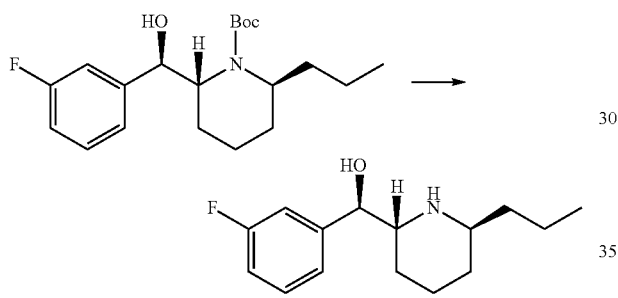

A mixture of tert-butyl (2R,6S)-2-((R)-(3-fluorophenyl)(hydroxy)methyl)-6-propylpiperidine-1-carboxylate (81 mg, 0.23 mmol), CeCl$_3$·7H$_2$O (129 mg, 0.35 mmol), NaI (44.9 mg, 0.30 mmol) and MeCN (4 mL) was heated in a sealed vial at 100° C. for 1 h. NaOH (aq, 1 M, 20 mL) and EtOAc (20 mL) was added and the mixture was shaken until it became colorless. The layers were separated and the organic phase was washed with H$_2$O, dried over Na$_2$SO$_4$ and concentrated. The residue was purified by chromatography to give the title compound (40 mg, 0.16 mmol, 69%).

$^1$H NMR (400 MHz, CDCl$_3$): δ 7.32-7.27 (m, 1H), 7.13-7.06 (m, 2H), 6.98-6.93 (m, 1H), 4.61 (d, J=9.1 Hz, 1H), 2.87-2.81 (m, 2H), 2.44 (s, 2H), 1.75-1.68 (m, 1H), 1.65-1.57 (m, 2H), 1.46-1.30 (m, 6H), 1.21-1.12 (m, 1H), 0.92 (t, J=7.0 Hz, 3H).

Example 3: (R)-(3,5-Difluorophenyl)((2R,6S)-6-propylpiperidin-2-yl)methanol

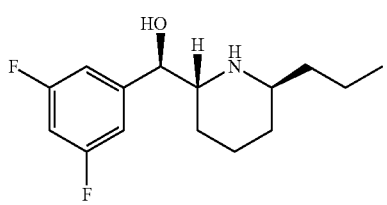 [SMILES: CCC[C@H]1CCC[C@H]([C@H](O)c2cc(F)cc(F)c2)N1]

The title compound was prepared in accordance with the procedure in Example 2, using 3,5-difluorobenzaldehyde in step (b).

$^1$H NMR (400 MHz, CDCl$_3$): δ 6.96-6.88 (m, 2H), 6.75-6.69 (m, 1H), 4.77 (d, J=9.3 Hz, 1H), 4.48 (br s, 2H), 3.23-3.17 (m, 1H), 3.07-3.02 (m, 1H), 1.92-1.84 (m, 1H), 1.68-1.56 (m, 3H), 1.55-1.34 (m, 6H), 0.94 (t, J=7.2 Hz, 3H).

Example 4: (R)-(3,4-Difluorophenyl)((2R,6S)-6-propylpiperidin-2-yl)methanol

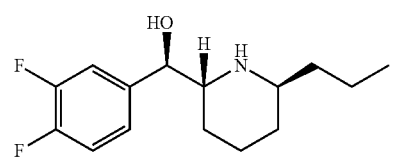 [SMILES: CCC[C@H]1CCC[C@H]([C@H](O)c2ccc(F)c(F)c2)N1]

The title compound was prepared in accordance with the procedure in Example 2, using 3,4-difluorobenzaldehyde in step (b).

$^1$H NMR (400 MHz, CDCl$_3$): δ 7.21 (ddd, J=11.3, 7.7, 2.0 Hz, 1H), 7.15-7.03 (m, 2H), 4.63 (d, J=9.3 Hz, 1H), 3.03 (br s, 2H), 2.97-2.91 (m, 1H), 2.86 (dt, J=9.7, 5.1 Hz, 1H), 1.81-1.72 (m, 1H), 1.64-1.57 (m, 2H), 1.53-1.44 (m, 1H), 1.45-1.31 (m, 5H), 1.29-1.20 (m, 1H), 0.93 (t, J=7.1 Hz, 3H).

Example 5: 3-((R)-Hydroxy((2R,6S)-6-propylpiperidin-2-yl)methyl)phenol Acetate

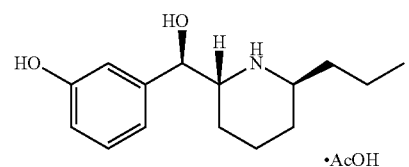 [SMILES: "·AcOH" ; CCC[C@H]1CCC[C@H]([C@H](O)c2cccc(O)c2)N1]

(a) tert-Butyl (2R,6S)-2-((R)-(3-(benzyloxy)phenyl)(hydroxy)methyl)-6-propyl-piperidine-1-carboxylate

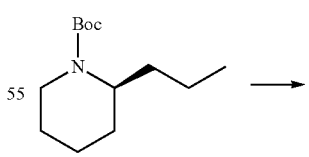

The sub-title compound was prepared in accordance with the procedure in Example 2, Step (b), using 3-benzyloxy-benzaldehyde.

(b) (R)-(3-(Benzyloxy)phenyl)((2R,6S)-6-propyl piperidin-2-yl)methanol

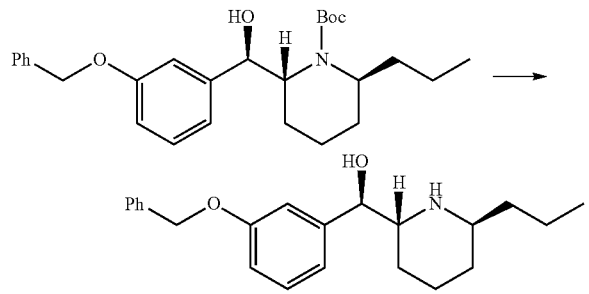

KOH (501 mg, 9.1 mmol) in H$_2$O (2 mL) was added to a solution of tert-butyl (2R,6S)-2-((R)-(3-(benzyloxy)phenyl)(hydroxy)methyl)-6-propylpiperidine-1-carboxylate (100 mg, 0.23 mmol) in EtOH (2 mL). The mixture was heated in a sealed vial at 140° C. for 7 d, cooled and partitioned between EtOAc and H$_2$O. The aq layer was extracted with EtOAc and the combined organic phases dried over Na$_2$SO$_4$, concentrated and purified by chromatography to give the title compound (30 mg, 0.088 mmol, 39%).

(c) 3-((R)-Hydroxy((2R,6S)-6-propylpiperidin-2-yl)methyl)phenol Acetate

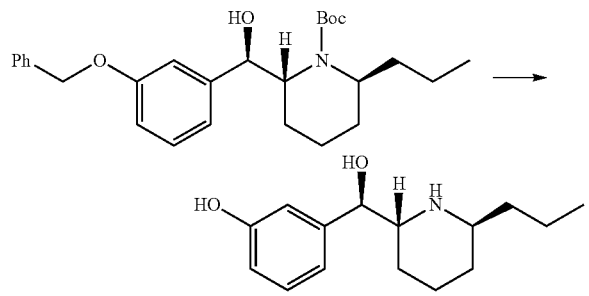

A mixture of (R)-(3-(benzyloxy)phenyl)((2R,6S)-6-propylpiperidin-2-yl)methanol (30 mg, 0.088 mmol), Pd—C (10%, 9.4 mg, 0.0088 mmol) and AcOH (2 mL) was hydrogenated at 9 atm and rt for 2 h. The mixture was filtered through Celite and the filter cake washed with AcOH. The filtrates were concentrated and purified by revere-phase chromatography to give the title compound (10 mg, 0.032 mmol, 37%).

$^1$H NMR (400 MHz, D$_2$O): δ 7.40-7.35 (m, 1H), 7.02-7.00 (m, 1H), 6.97-6.92 (m, 2H), 4.84 (d, J=9.5 Hz, 1H), 3.60-3.54 (m, 2H), 1.94 (s, 3H), 1.94-1.89 (m, 1H), 1.85-1.55 (m, 6H), 1.52-1.35 (m, 3H), 0.98 (t, J=7.3 Hz, 3H).

Example 6: 3-((R)-Hydroxy((2R,6R)-6-propylpiperidin-2-yl)methyl)phenol

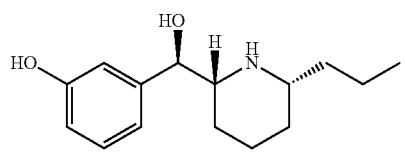 [SMILES: CCC[C@@H]1CCC[C@H]([C@H](O)c2cccc(O)c2)N1]

The title compound was obtained in accordance to Example 1, Steps (c) and (d), from tert-butyl (2R,6R)-2-formyl-6-propylpiperidine-1-carboxylate using 3-benzyloxymagnesium bromide in Step (c) followed by debenzylation in accordance with Example 5, Step (c). Purification by reverse phase chromatography in the last step gave the acetic acid salt (20%) as well as the free base (42%).

$^1$H NMR (400 MHz, CDCl$_3$): δ 7.14 (m, 1H), 7.06 (s, 1H), 6.77 (m, 1H), 6.73 (m, 1H), 6.49-5.01 (br s, 3H), 4.61 (d, J=9.4 Hz, 1H), 3.10-2.95 (m, 1H), 2.72-2.84 (m, 1H), 2.00 (s, 3H), 1.82 (m, 1H), 1.76-1.60 (m, 2H), 1.60-1.10 (m, 7H), 0.83 (t, J=7.1 Hz, 3H).

Example 7: (R)-(3-Fluorophenyl)((2R,5R)-5-propylpyrrolidin-2-yl)methanol Acetate

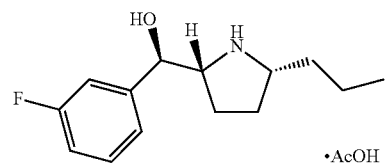 [SMILES: "·AcOH" ; CCC[C@@H]1CC[C@H]([C@H](O)c2cccc(F)c2)N1]

(a) 1-Benzyl 2-methyl (R)-5-oxopyrrolidine-1,2-dicarboxylate

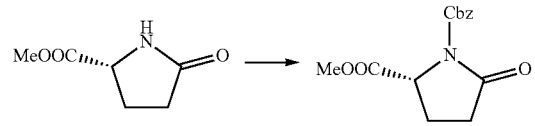 [SMILES: COC(=O)[C@H]1CCC(=O)N1 ; COC(=O)[C@H]1CCC(=O)N1C(=O)OCc1ccccc1]

Benzyl chloroformate (0.85 mL, 5.9 mmol) was added during 20 min to a solution of methyl (R)-5-oxopyrrolidine-2-carboxylate (500 mg, 3.5 mmol), DMAP (0.19 g, 1.6 mmol) and DIPEA (0.82 ml) in MeCN (7 mL) at rt. After 2 h additional portions of DMAP (0.19 g, 1.6 mmol), DIPEA (0.82 ml) and benzyl chloroformate (0.85 mL, 5.9 mmol) were added and stirring was continued for another 3 h. The mixture was concentrated and EtOAc was added to the residue. The mixture was washed with brine, dried over Na$_2$SO$_4$, concentrated and purified by chromatography to give the sub-title compound (775 mg, 2.8 mmol, 80%).

(b) Methyl (S)-3-(((benzyloxy)carbonyl)amino)-5-oxooctanoate

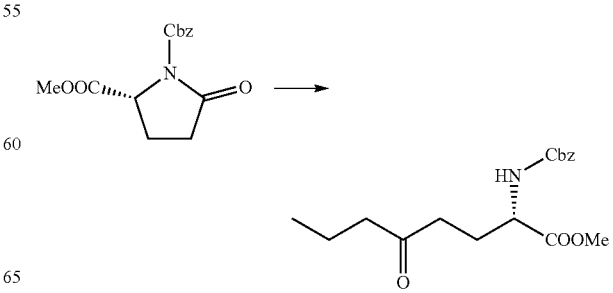

A solution of n-propylmagnesium chloride (1 M, 4.32 mL, 4.32 mmol) and TMEDA (0.47 mL, 4.32 mmol) in THF (4.32 mL) was added over 15 min to a solution of 1-benzyl 2-methyl (R)-5-oxopyrrolidine-1,2-dicarboxylate (400 mg, 1.44 mmol) in THF at −78° C. The mixture was stirred at −78° C. for 30 min and i-PrOH (2 mL) followed by NH₄Cl (aq, sat, 2 mL) were added. The cooling bath was removed and the mixture was stirred for 45 min partitioned between CH₂Cl₂ and H₂O. The aq layer was extracted with CH₂Cl₂ and the combined organic phases were dried over MgSO₄, concentrated and purified by chromatography to give the sub-title compound (267 mg, 0.80 mmol, 55%).

(c) 1-Benzyl 2-methyl (2R,5R)-5-propylpyrrolidine-1,2-dicarboxylate

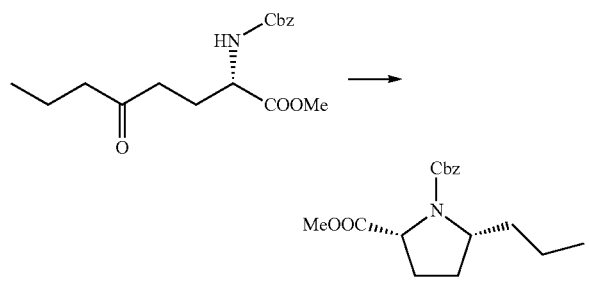

BF₃-Et₂O (0.144 mL, 1.15 mmol) was added dropwise to a solution of methyl (S)-3-(((benzyloxy)carbonyl)amino)-5-oxooctanoate (350 mg, 1.04 mmol) and Ph₃SiH (0.30 g, 1.15 mmol) in CH₂Cl₂ (3 mL) at −78° C. The mixture was stirred at −78° C. for 15 min, the cooling bath removed, and stirring was continued for 1 h. NaHCO₃ (aq, sat) and CH₂Cl₂ were added. The aq layer was extracted with CH₂Cl₂ and the combined organic phases were dried over MgSO₄, concentrated and purified by chromatography to give the sub-title compound (255 mg, 0.84 mmol, 80%).

(d) Benzyl (2R,5R)-2-(hydroxymethyl)-5-propylpyrrolidine-1-carboxylate

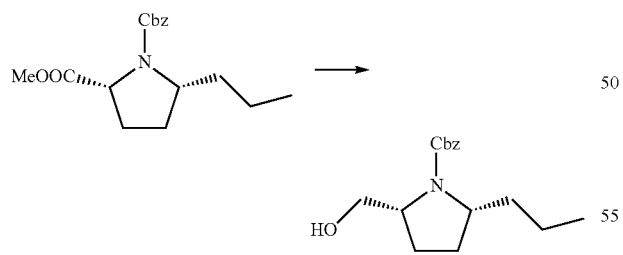

LiBH₄ (4 M in THF, 61 µL, 0.25 mmol) was added to a solution of 1-benzyl 2-methyl (2R,5R)-5-propylpyrrolidine-1,2-dicarboxylate (50 mg, 0.16 mmol) in THF (1 mL) at 0° C. The mixture was slowly allowed to come to rt overnight and cooled to 0° C. H₂O (2 mL) was added and the mixture was extracted with EtOAc. The combined organic phases were washed with brine, dried over MgSO₄ and concentrated to give the sub-title compound (43 mg, 0.16 mmol, 95%).

(e) Benzyl (2R,5R)-2-formyl-5-propylpyrrolidine-1-carboxylate

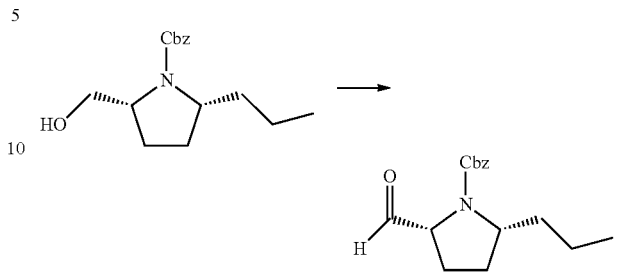

Dess-Martin periodinane (169 mg, 0.40 mmol) in CH₂Cl₂ (10 mL) was added to a solution of benzyl (2R,5R)-2-(hydroxymethyl)-5-propylpyrrolidine-1-carboxylate (92 mg, 0.33 mmol) in CH₂Cl₂ (4 mL). The mixture was stirred at rt for 1 h. CH₂Cl₂ was added and the mixture was washed with NaHCO₃ (aq, sat), brine, dried over MgSO₄, concentrated and purified by chromatography to give the sub-title compound (61 mg, 0.22 mmol, 67%).

(f) Benzyl (2R,5R)-2-((R)-(3-fluorophenyl)(hydroxy)methyl)-5-propylpyrrolidine-1-carboxylate

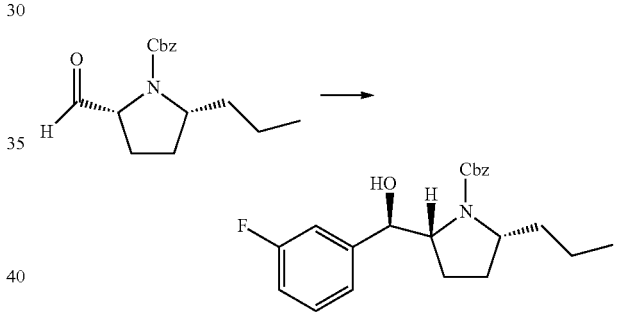

A solution of benzyl (2R,5R)-2-formyl-5-propylpyrrolidine-1-carboxylate (77 mg, 0.28 mmol) in THF (0.5 mL) was added to a stirred suspension of CeCl₃ (138 mg, 0.56 mmol) in THF (0.5 mL) The mixture was stirred at rt for 40 min and 3-fluorophenyl magnesium bromide (1 M in THF, 0.42 mL, 0.42 mmol) was added at −78° C. The mixture was stirred at rt for 2 h and NH₄Cl (aq, sat, 5 mL) followed by EtOAc and H₂O were added. The aq layer was extracted with EtOAc and the combined organic phases were dried over Na₂SO₄, concentrated and purified by chromatography to give the sub-title compound (39 mg, 0.10 mmol, 38%).

(g) (R)-(3-Fluorophenyl)((2R,5R)-5-propylpyrrolidin-2-yl)methanol Acetate

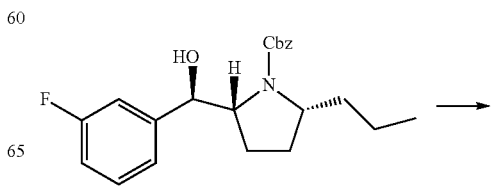

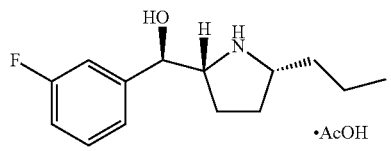

The title compound was prepared from benzyl (2R,5R)-2-((R)-(3-fluorophenyl)(hydroxy)-methyl)-5-propylpyrrolidine-1-carboxylate in accordance with the procedure in Example 5, Step (c).

$^1$H NMR (400 MHz, CDCl$_3$): δ 7.32-7.25 (m, 1H, overlapping), 7.16-7.08 (m, 2H), 7.00-6.92 (m, 1H), 6.55-5.82 (br s, 2H), 4.59 (d, J=7.6 Hz, 1H), 3.58-3.48 (m, 1H), 3.30-3.20 (m, 1H), 2.09-2.00 (s, 3H, overlapping), 2.00-1.92 (m, 1H, overlapping), 1.78-1.45 (m, 5H), 1.42-1.27 (m, 2H), 0.90 (t, J=7.3 Hz, 3H).

Example 8: 3-((R)-Hydroxy((2R,5R)-5-propylpyrrolidin-2-yl)methyl)phenol

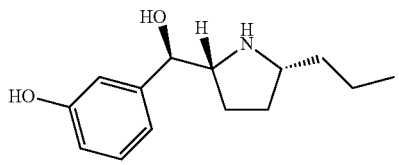 [SMILES: CCC[C@@H]1CC[C@H]([C@H](O)c2cccc(O)c2)N1]

The title compound was prepared from benzyl (2R,5R)-2-formyl-5-propylpyrrolidine-1-carboxylate and 3-benzyloxyphenylmagnesium bromide in accordance with the procedure in Example 7, Step (f), followed by debenzylation in accordance with the procedure in Example 5, Step (c).

$^1$H NMR (400 MHz, CDCl$_3$): δ 7.14-7.07 (m, 1H), 6.94 (s, 1H), 6.80-6.74 (m, 1H), 6.74-6.65 (m, 1H), 6.11-4.73 (br s, 2H), 4.64 (d, J=9.3 Hz, 1H), 3.75-3.62 (m, 1H), 3.41-3.28 (m, 1H), 2.09-1.91 (m, 1H), 1.79-1.57 (m, 5H), 1.40-1.17 (m, 2H), 0.87 (t, J=7.3 Hz, 3H).

Example 9: Racemic mixture of 3-((R)-Hydroxy((2S,5S)-5-methylpyrrolidin-2-yl)methyl)-phenol Acetate and 3-((S)-Hydroxy((2R,5R)-5-methylpyrrolidin-2-yl)methyl)phenol Acetate

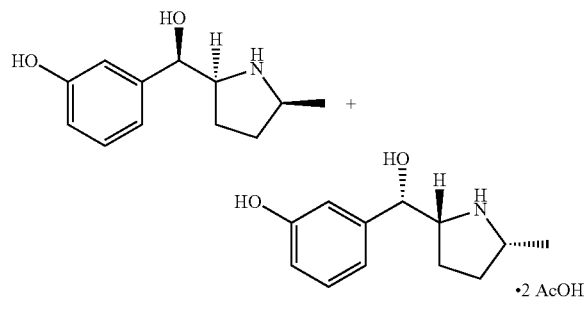

(a) 1-Bromo-2-tosylacetylene

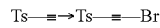

AgNO$_3$ (0.56 g, 3.3 mmol), followed by N-bromosuccinimide (6.5 g, 36.6 mmol) was added to a solution of tosylacetylene (6.0 g, 33.3 mmol) in acetone (140 mL) at rt. The mixture was stirred at rt for 1 h and filtered through Celite. The filtrate was concentrated and the residue purified by chromatography to give the sub-title compound (7.8 g, 30.1 mmol, 91%).

(b) tert-Butyl 2-bromo-3-tosyl-7-azabicyclo[2.2.1]hepta-2,5-diene-7-carboxylate

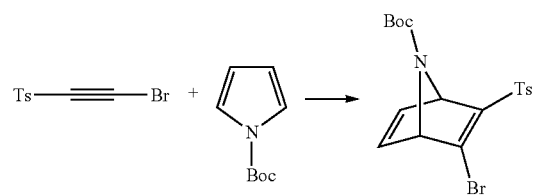 [SMILES: Cc1ccc(S(=O)(=O)C#CBr)cc1 ; CC(C)(C)OC(=O)n1cccc1 ; Cc1ccc(S(=O)(=O)C2=C(Br)C3C=CC2N3C(=O)OC(C)(C)C)cc1]

A mixture of 1-bromo-2-tosylacetylene (1 g, 3.9 mmol) and 1-tert-butoxycarbonylpyrrole (3.2 g, 19.3 mmol) was heated in a sealed vial at 90° C. for 2 h. The mixture was allowed to cool and purified by chromatography to give the sub-title compound (0.71 g, 1.67 mmol, 43%).

(c) tert-Butyl 5-oxo-6-tosyl-7-azabicyclo[2.2.1]hept-2-ene-7-carboxylate

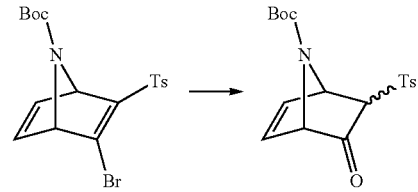 [SMILES: Cc1ccc(S(=O)(=O)C2=C(Br)C3C=CC2N3C(=O)OC(C)(C)C)cc1 ; Cc1ccc(S(=O)(=O)C2C(=O)C3C=CC2N3C(=O)OC(C)(C)C)cc1]

Triethylamine (2.6 mL, 18.9 mmol) was added to a solution of tert-butyl 2-bromo-3-tosyl-7-azabicyclo[2.2.1]hepta-2,5-diene-7-carboxylate (1.61 g, 3.8 mmol) in MeCN (50 mL) at rt. Diethylamine (0.47 mL, 4.5 mmol) was slowly added and the mixture was stirred at rt for 2 h. HCl (4 M, 16 mL) was added and the mixture was stirred at rt for 3 h. CH$_2$Cl$_2$ (140 mL) was added and the mixture was washed with H$_2$O. The aq phase was extracted with CH$_2$Cl$_2$ and the combined organic phases were dried over Na$_2$SO$_4$ and concentrated. The residue was purified by chromatography to give the sub-title compound (0.98 g, 2.7 mmol, 72%).

(d) (cis)-(endo)-tert-Butyl (5-hydroxy-6-tosyl-7-azabicyclo[2.2.1]hept-2-ene-7-carboxylate

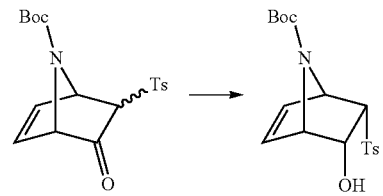 [SMILES: Cc1ccc(S(=O)(=O)C2C(=O)C3C=CC2N3C(=O)OC(C)(C)C)cc1 ; Cc1ccc(S(=O)(=O)C2C(O)C3C=CC2N3C(=O)OC(C)(C)C)cc1]

LiBH₄ (4 M in THF, 0.69 mL, 0.28 mmol) was added rapidly to a solution of tert-butyl 5-oxo-6-tosyl-7-azabicyclo[2.2.1]hept-2-ene-7-carboxylate (1 g, 2.75 mmol) in THF (20 mL) at −78° C. After 15 min at −78° C., NH₄Cl (aq, sat, 3 mL) was added and the stirred mixture was allowed to come to rt. EtOAc was added and the mixture was washed with H₂O, brine and concentrated. The residue was purified by chromatography to give the sub-title compound (670 mg, 1.83 mmol, 67%).

(e) (cis)-(endo)-tert-Butyl 2-hydroxy-3-tosyl-7-azabicyclo[2.2.1]heptane-7-carboxylate

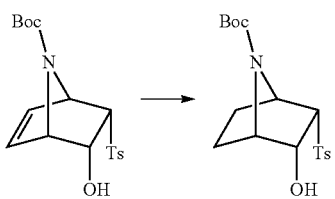 [SMILES: Cc1ccc(S(=O)(=O)C2C(O)C3C=CC2N3C(=O)OC(C)(C)C)cc1 ; Cc1ccc(S(=O)(=O)C2C(O)C3CCC2N3C(=O)OC(C)(C)C)cc1]

Hydrogen was bubbled through a mixture of (cis)-(endo)-tert-Butyl (5-hydroxy-6-tosyl-7-azabicyclo[2.2.1]hept-2-ene-7-carboxylate (670 mg, 1.83 mmol), Pd—C (10%, 195 mg, 0.18 mmol) and MeOH (18 mL) at rt over 1 h. The mixture was filtered through Celite and concentrated to give the sub-title compound in a quantitative yield that was used in the next step without any further purification.

(f) (cis)-tert-Butyl 2-formyl-5-(tosylmethyl)pyrrolidine-1-carboxylate

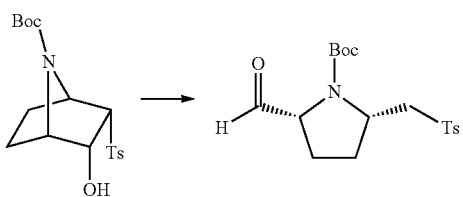 [SMILES: Cc1ccc(S(=O)(=O)C2C(O)C3CCC2N3C(=O)OC(C)(C)C)cc1 ; Cc1ccc(S(=O)(=O)C[C@@H]2CC[C@H](C=O)N2C(=O)OC(C)(C)C)cc1]

NaOH (2.3 M in MeOH, 0.15 mL, 0.35 mmol) was added to a solution of (cis)-(endo)-tert-butyl 2-hydroxy-3-tosyl-7-azabicyclo[2.2.1]heptane-7-carboxylate (0.51 g, 1.39 mmol) in MeOH (20 mL) at rt. The mixture was stirred at rt for 16 h, whereafter NH₄Cl (aq, sat) and EtOAc were added. The layers were separated and the aq phase extracted with EtOAc. The combined organic phases were dried over Na₂SO₄ and concentrated to give the sub-title compound (0.51 mg, 1.37 mmol, 99%), which was used in the next step without any further purification.

(g) (syn)-tert-Butyl 2-(3-(benzyloxy)phenyl)(hydroxy)methyl)-5-(tosylmethyl)-pyrrolidine-1-carboxylate and (anti)-tert-Butyl 2-(3-(benzyloxy)phenyl)(hydroxy)methyl)-5-(tosylmethyl)pyrrolidine-1-carboxylate

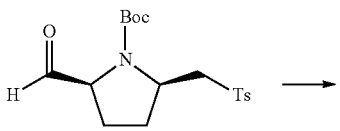

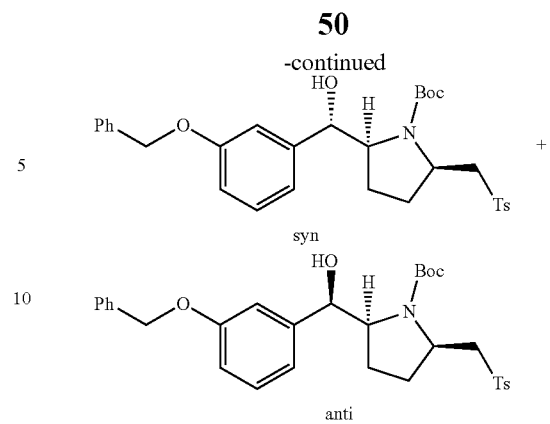

(cis)-tert-Butyl 2-formyl-5-(tosylmethyl)pyrrolidine-1-carboxylate (352 mg, 0.96 mmol) was allowed to react with 3-benzyloxyphenylmagnesium bromide in accordance with the procedure in Example 7, Step (f) to after chromatographic separation give racemic mixtures of (syn) tert-butyl 2-(3-(benzyloxy)phenyl)(hydroxy)methyl)-5-(tosylmethyl)-pyrrolidine-1-carboxylate (179 mg, 0.32 mmol, 34%) and (anti) tert-butyl 2-(3-(benzyloxy)phenyl)(hydroxy)methyl)-5-(tosylmethyl)pyrrolidine-1-carboxylate (233 mg, 0.42 mmol, 44%).

(h) (Anti)-tert-Butyl 2-(3-(benzyloxy)phenyl)(hydroxy)methyl)-5-methylpyrrolidine-1-carboxylate

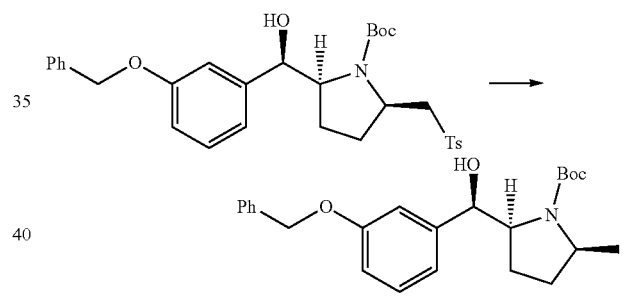

SmI₂ (0.05 M in THF, 31 mL, 1.5 mmol) was added dropwise to a mixture of (anti)-tert-butyl 2-(3-(benzyloxy)phenyl)(hydroxy)methyl)-5-(tosylmethyl)pyrrolidine-1-carboxylate (134 mg, 0.24 mmol), HMPA (0.80 mL, 4.6 mmol) and THF (4 mL) at rt. The mixture was stirred at rt for 22 h. NH₄Cl (aq, sat, 30 mL) and EtOAc (20 mL) was added and after 5 min the layers were separated and the aq phase extracted with EtOAc. The combined organic phases were washed with brine, dried over Na₂SO₄ and concentrated. The residue was purified by chromatography to give a mixture of the sub-title compound (35 mg, 0.09 mmol, 36%).

(i) (anti)-(3-(Benzyloxy)phenyl)(5-methylpyrrolidin-2-yl)methanol

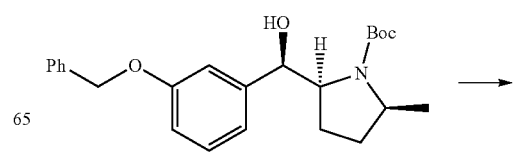

51

-continued

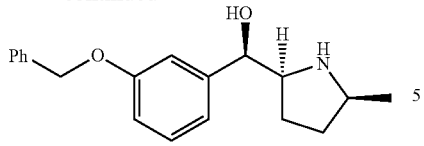

NaOH (aq, 0.5 M, 2.5 mL, 1.2 mmol) was added to a mixture of (anti)-tert-butyl 2-(3-(benzyloxy)phenyl)(hydroxy)methyl)-5-methylpyrrolidine-1-carboxylate (53 mg, 0.13 mmol) in EtOH (2.5 mL). The mixture was heated in a sealed vial at 120° C. After 64 h and after 84 h, additional portions of NaOH (aq, 0.5 M, 2.5 mL, 1.2 mmol) were added, and after 108 h another portion of NaOH (aq, 0.5 M, 2.5 mL, 1.2 mmol) and EtOH (1 mL) were added. After 132 h the mixture was concentrated and extracted with EtOAc. The combined extracts were washed with brine, dried over $Na_2SO_4$ and concentrated. The residue was purified by chromatography to give a mixture of the sub-title compound (15 mg, 0.05 mmol, 38%).

(j) Racemic Mixture of 3-((R)-Hydroxy((2S,5S)-5-methylpyrrolidin-2-yl)methyl)phenol Acetate and 3-((S)-Hydroxy((2R,5R)-5-methylpyrrolidin-2-yl)methyl)phenol Acetate

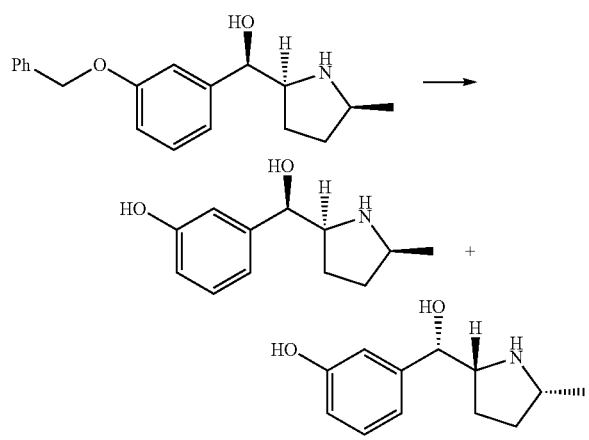

The title compounds were prepared in accordance with the procedure in Example 5, Step (c), from (anti)-(3-(benzyloxy)phenyl)(5-methylpyrrolidin-2-yl)methanol.

$^1$H NMR (400 MHz, $D_2O$): δ 7.40-7.32 (m, 1H), 7.05-6.98 (m, 1H), 6.97-6.93 (s, 1H), 6.93-6.88 (m, 1H), 4.95 (d, J=6.1 Hz, 1H), 3.98-3.89 (m, 1H), 3.77-3.65 (m, 1H), 2.28-2.17 (m, 1H), 2.13-2.02 (m, 2H), 1.92 (s, 3H), 1.81-1.64 (m, 1H), 1.38 (d, J=6.7 Hz, 3H).

Example 10: Racemic Mixture of 3-((R)-Hydroxy((2R,5R)-5-methylpyrrolidin-2-yl)methyl)-phenol Acetate and 3-(S)-Hydroxy((2S,5S)-5-methylpyrrolidin-2-yl)methyl)phenol Acetate

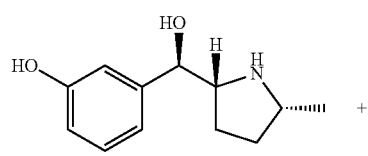

52

-continued

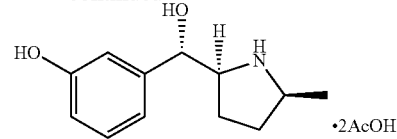

(a) (syn)-(3-(Benzyloxy)phenyl)(5-methylpyrrolidin-2-yl)methanol

TFA (52 μL, 68 μmol) was added dropwise to a solution of (syn)-tert-butyl 2-(3-(benzyloxy)phenyl)(hydroxy)methyl)-5-methylpyrrolidine-1-carboxylate (from Example 9, step (g) using the procedure in Example 9, Step (h)) (27 mg, 68 μmol) and $CH_2Cl_2$ (1 mL) at rt. The mixture was stirred at rt for 2 h and concentrated. DIPEA (47 μL, 0.27 mmol) was added and the material was purified by chromatography to give a mixture of the sub-title compounds (6 mg, 20 μmol, 30%).

(b) Racemic Mixture of 3-((R)-Hydroxy((2R,5R)-5-methylpyrrolidin-2-yl)methyl)phenol Acetate and 3-((S)-Hydroxy((2S,5S)-5-methylpyrrolidin-2-yl)methyl)phenol Acetate The title compounds were prepared in accordance with the procedure in Example 5, Step (c), from (syn)-(3-(benzyloxy)phenyl)(5-methylpyrrolidin-2-yl)methanol.

$^1$H NMR (400 MHz, $D_2O$): δ 7.40-7.32 (m, 1H), 7.04-6.99 (m, 1H), 6.98-6.90 (m, 3H), 4.90-4.74 (m, 1H), 3.98-3.88 (m, 1H), 3.80-3.69 (m, 1H), 2.29-2.18 (m, 1H), 1.99 (s, 3H), 1.95-1.69 (m, 3H), 1.45 (d, J=6.6 Hz, 2H).

Example 11: Racemic mixture of (R)-((2S,5S)-5-Methylpyrrolidin-2-yl)(phenyl)methanol and (S)-((2R,5R)-5-Methylpyrrolidin-2-yl)(phenyl)methanol The title compounds were obtained in accordance with Example 9, using phenylmagnesium bromide in Step (g).

$^1$H NMR (300 MHz, $CDCl_3$): δ 7.42-7.28 (m, 4H), 7.28-7.20 (m, 1H), 4.94-4.85 (m, 1H), 3.69-3.56 (m, 1H), 3.76-3.06 (br. s., 2H, overlapping), 3.46-3.32 (m, 1H), 1.93-1.74 (m, 2H), 1.50-1.34 (m, 2H), 1.29-1.21 (m, 3H).

Example 12: Racemic mixture of (R)-((2R,5R)-5-Methylpyrrolidin-2-yl)(phenyl)methanol and (S)-((2S,5S)-5-Methylpyrrolidin-2-yl)(phenyl)methanol

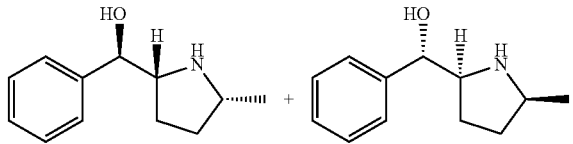

The title compounds were obtained in accordance with Example 9, using phenylmagnesium bromide in Step (g).
$^1$H NMR (400 MHz, CDCl$_3$): δ 7.39-7.30 (m, 4H), 7.29-7.23 (m, 1H), 4.60 (d, J=6.3 Hz, 1H), 3.59-3.51 (m, 1H), 3.44-3.37 (m, 1H), 3.59-2.97 (br. s, 2H, overlapping), 1.99-1.89 (m, 1H), 1.82-1.71 (m, 2H), 1.59-1.47 (m, 1H), 1.30 (d, J=6.2 Hz, 3H).

Example 13: (S)-(3-Fluorophenyl)((2R,6R)-6-propylpiperidin-2-yl)methanol

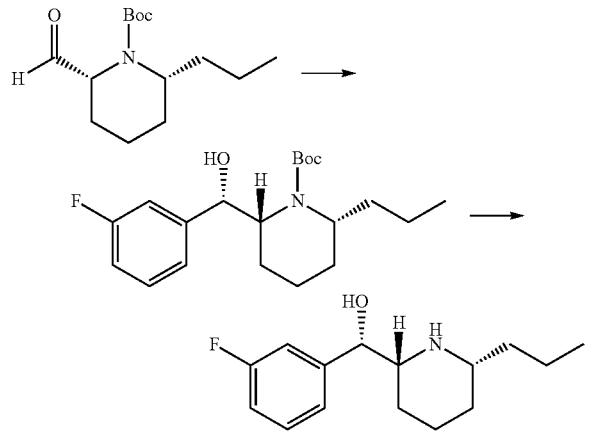

The title compound was obtained from 3-fluorophenylmagnesium bromide and tert-butyl (2R,6R)-2-formyl-6-propylpiperidine-1-carboxylate, first by isolating the intermediate tert-butyl (2R,6R)-2-((S)-(3-fluorophenyl)(hydroxy)methyl)-6-propylpiperidine-1-carboxylate in the chromatographic purification step described in Example 1, Step (c) followed by the removal of the protecting group as described in Example 1, Step (d).
$^1$H NMR (400 MHz, CDCl$_3$): δ 7.33-7.26 (m, 1H), 7.14-7.08 (m, 2H), 6.98-6.91 (m, 1H), 4.84 (d, J=4.0 Hz, 1H), 3.04 (br s, 2H), 2.93-2.88 (m, 1H), 2.71-2.62 (m, 1H), 1.82-1.74 (m, 1H), 1.73-1.64 (m, 1H), 1.51-1.18 (m, 7H), 1.11-0.99 (m, 1H), 0.88 (t, J=7.2 Hz, 3H).

Example 14: 3-((S)-Hydroxy((2R,6R)-6-propylpiperidin-2-yl)methyl)phenol Hydrochloride

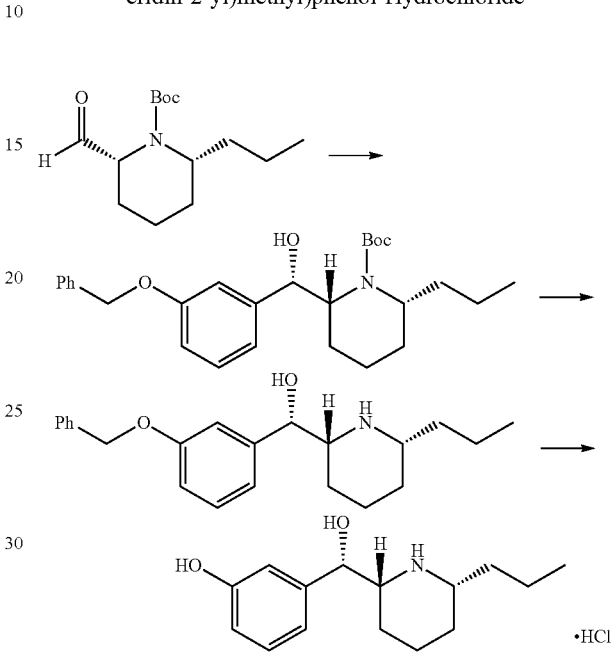

The title compound was obtained in accordance to Example 6 from tert-butyl (2R,6R)-2-formyl-6-propylpiperidine-1-carboxylate and 3-benzyloxymagnesium bromide. The intermediate tert-butyl (2R,6R)-2-((S)-(3-(benzyloxy)phenyl)(hydroxy)methyl)-6-propyl-piperidine-1-carboxylate was isolated during the chromatographic purification step and the protecting groups were removed as described in Example 1, Step (d) and Example 5, Step (c). It was finally obtained as the hydrochloride salt by dissolution in Et$_2$O followed by precipitation by addition of HCl (2 M in Et$_2$O).
$^1$H NMR (400 MHz, CD$_3$OD): δ 7.20 (t, J=7.8 Hz, 1H), 6.90-6.83 (m, 2H), 6.74-6.70 (m, 1H), 5.02 (d, J=3.0 Hz, 1H), 3.34-3.27 (m, 1H, overlapped with MeOD), 3.20-3.11 (m, 1H), 2.05-1.95 (m, 1H), 1.91-1.83 (m, 1H), 1.79-1.58 (m, 3H), 1.57-1.28 (m, 6H), 1.01 (t, J=7.3 Hz, 3H).

The compounds in Table 1 were obtained in accordance with the procedures described in Example 1, 13 and 14 using the appropriately substituted phenylmagnesium bromide.

TABLE 1

| Example 15 | 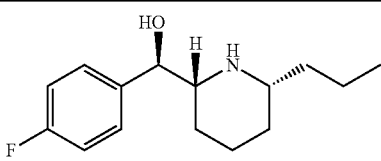 |
|---|---|

(R)-(4-Fluorophenyl)((2R,6R)-6-propylpiperidin-2-yl)methanol
$^1$H NMR (400 MHz, CDCl$_3$): δ 7.33-7.27 (m, 2H), 7.07-6.99 (m, 2H), 4.34 (d, J = 7.3 Hz, 1H), 2.65-2.60 (m, 1H), 2.50-2.42 (m, 1H), 1.90 (br s, 2H), 1.80-1.71 (m, 1H), 1.68-1.62 (m, 1H), 1.42-1.19 (m, 6H), 1.15-1.06 (m, 1H), 1.06-0.93 (m, 1H). 0.94-0.86 (m, 3H).

TABLE 1-continued

Example 16 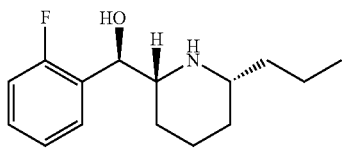 [SMILES: CCC[C@@H]1CCC[C@H]([C@H](O)c2ccccc2F)N1]

(R)-(2-Fluorophenyl)((2R,6R)-6-propylpiperidin-2-yl)methanol
$^1$H NMR (400 MHz, CDCl$_3$): δ 7.35-7.29 (m, 2H), 7.07-6.99 (m, 2H), 4.57 (d, J = 4.9 Hz, 1H), 2.76 (ddd, J = 10.7, 4.9, 2.7 Hz, 1H), 2.55-2.49 (m, 1H), 1.80-1.73 (m, 1H), 1.64-1.56 (m, 1H), 1.47-1.42 (m, 1H), 1.35-1.20 (m, 5H), 1.23-1.06 (m, 1H), 1.00-0.91 (m, 1H), 0.90-0.85 (m, 3H)

Example 17 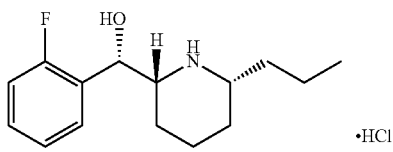 [SMILES: CCC[C@@H]1CCC[C@H]([C@@H](O)c2ccccc2F)N1 ; Cl]

(S)-(2-Fluorophenyl)((2R,6R)-6-propylpiperidin-2-yl)methanol hydrochloride
$^1$H NMR (400 MHz, CDCl$_3$): δ 10.22 (s, 1H), 7.84 (s, 1H), 7.58 (td, J = 7.6, 1.8 Hz, 1H), 7.30-7.15 (m, 1H), 7.10 (td, J = 7.5, 1.2 Hz, 1H), 6.99-6.94 (m, 1H), 5.95 (s, 1H), 5.53 (d, J = 4.0 Hz, 1H), 3.39 (t, J = 10.6 Hz, 1H), 3.12 (q, J = 11.2 Hz, 1H), 2.22-2.13 (m, 1H), 1.99-1.72 (m, 4H), 1.61-1.23 (m, 5H), 0.85 (t, J = 7.3 Hz, 3H).

Example 18: (S)-(3-Fluorophenyl)((2R,6S)-6-propylpiperidin-2-yl)methanol

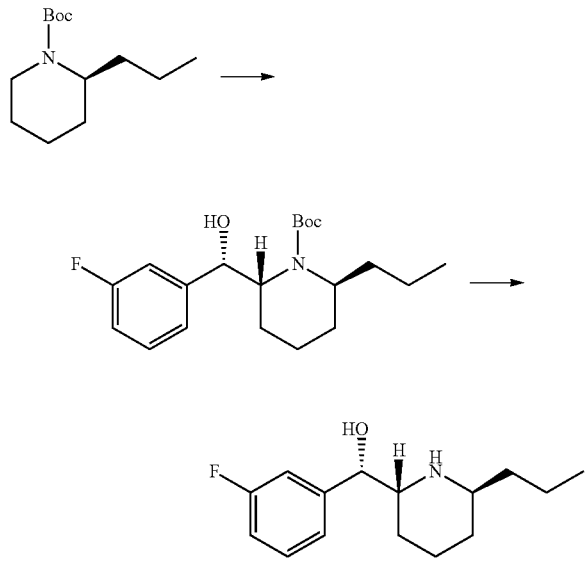

The title compound was obtained from tert-butyl (S)-2-propylpiperidine-1-carboxylate and 3-fluorobenzaldehyde as described in Example 2 by first by isolating the intermediate tert-butyl (2R,6S)-2-((S)-(3-fluorophenyl)(hydroxy)methyl)-6-propylpiperidine-1-carboxylate in the chromatographic purification step described in Example 2, Step (b) followed by the removal of the protecting group as described in Example 2, Step (c).

$^1$H NMR (400 MHz, CDCl$_3$): δ 7.32-7.27 (m, 1H), 7.15-7.07 (m, 2H), 6.98-6.93 (m, 1H), 4.95 (d, J=4.8 Hz, 1H), 3.60 (br s, 2H), 3.23-3.17 (m, 1H), 3.11-3.07 (m, 1H), 1.74-1.61 (m, 2H), 1.60-1.54 (m, 1H), 1.53-1.41 (m, 5H), 1.32-1.18 (m, 2H), 0.91 (t, J=7.3 Hz, 3H).

Example 19: 3-((R)-Hydroxy((2R,6R)-6-propylpiperidin-2-yl)methyl)phenol Hydrochloride

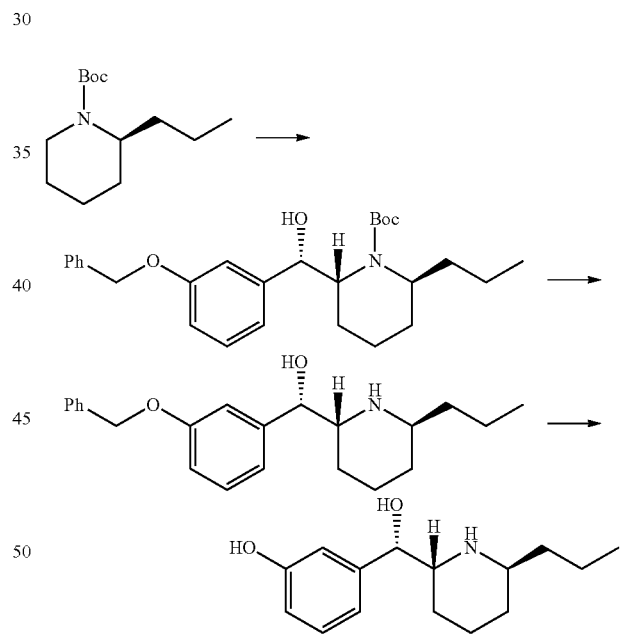

The title compound was obtained in accordance to Example 2 from tert-butyl (S)-2-propylpiperidine-1-carboxylate and 3-benzyloxybenzaldehyde. The intermediate tert-butyl (2R,6S)-2-((S)-(3-(benzyloxy)phenyl)(hydroxy)methyl)-6-propylpiperidine-1-carboxylate was isolated during the chromatographic purification step and the protecting groups were removed as described in Example 1, Step (d) and Example 5, Step (c).

$_1$H NMR (400 MHz, D$_2$O): δ 7.43-7.33 (m, 1H), 7.00 (d, J=7.8 Hz, 1H), 6.98-6.90 (m, 2H), 4.94 (d, J=5.6 Hz, 1H), 3.67-3.49 (m, 2H), 1.90-1.66 (m, 6H), 1.69-1.51 (m, 2H), 1.46-1.23 (m, 2H), 0.94 (t, J=7.3 Hz, 3H).

The compounds in Table 2 were obtained in accordance with the procedures described in Examples 2 and 18 using the appropriately substituted benzaldehydes. When the title compounds are hydrochloride salts they are obtained by dissolution of the free base in Et₂O followed by precipitation by addition of HCl (2 M in Et₂O).

TABLE 2

Example 20

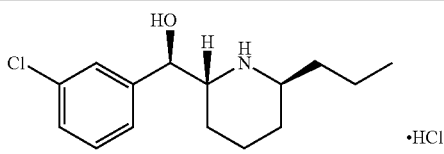 [SMILES: CCC[C@H]1CCC[C@H]([C@H](O)c2cccc(Cl)c2)N1 ; Cl]

(R)-(3-Chlorophenyl)((2R,6S)-6-propylpiperidin-2-yl)methanol hydrochloride
¹H NMR (400 MHz, CDCl₃): δ 9.28 (br s, 1H), 8.77 (br s, 1H), 7.42-7.38 (m, 1H), 7.31-7.21 (m, 3H), 5.68 (br s, 1H), 4.97 (d, J = 9.8 Hz, 1H), 3.70-3.60 (m, 1H), 3.46-3.35 (m, 1H), 2.16-2.04 (m, 1H), 2.00-1.89 (m, 1H), 1.79-1.68 (m, 2H), 1.68-1.59 (m, 2H), 1.58-1.48 (m, 2H), 1.50-1.38 (m, 2H), 0.97 (t, J = 7.3 Hz, 3H).

Example 21

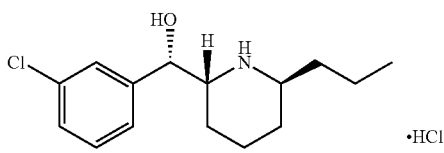 [SMILES: CCC[C@H]1CCC[C@H]([C@@H](O)c2cccc(Cl)c2)N1 ; Cl]

(S)-(3-Chlorophenyl)((2R,6S)-6-propylpiperidin-2-yl)methanol hydrochloride
¹H NMR (400 MHz, CDCl₃): δ 9.81 (d, J = 12.5 Hz, 1H), 8.50 (t, J = 12.1 Hz, 1H), 7.43 (s, 1H), 7.33-7.20 (m, 3H), 5.94 (d, J = 5.5 Hz, 1H), 5.81-5.68 (m, 1H), 3.86 (d, J = 10.8 Hz, 1H), 3.31 (t, J = 11.4 Hz, 1H), 2.18-2.07 (m, 1H), 2.06-1.95 (m, 1H), 1.86-1.67 (m, 3H), 1.64-1.55 (m, 1H), 1.51-1.30 (m, 4H), 1.01 (t, J = 7.2 Hz, 3H)

Example 22

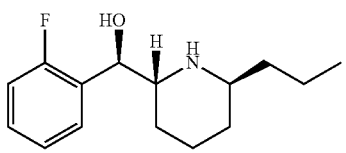 [SMILES: CCC[C@H]1CCC[C@H]([C@H](O)c2ccccc2F)N1]

(R)-(2-Fluorophenyl)((2R,6S)-6-propylpiperidin-2-yl)methanol
¹H NMR (400 MHz, CDCl₃): δ 7.50 (td, J = 7.4, 1.9 Hz, 1H), 7.28-7.20 (m, 1H), 7.17-7.13 (m, 1H), 7.03-6.98 (m, 1H), 5.04 (d, J = 9.4 Hz, 1H), 2.93-2.88 (m, 1H), 2.87-2.81 (m, 1H), 2.42 (br s, 2H), 1.76-1.55 (m, 3H), 1.47-1.28 (m, 6H), 1.19-1.07 (m, 1H), 0.97-0.89 (m, 3H).

Example 23

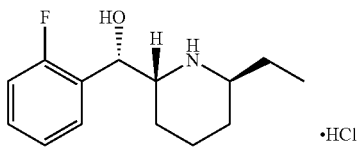 [SMILES: CC[C@H]1CCC[C@H]([C@@H](O)c2ccccc2F)N1 ; Cl]

(S)-(2-Fluorophenyl)((2R,6S)-6-propylpiperidin-2-yl)methanol hydrochloride
¹H NMR (400 MHz, CDCl₃): δ 10.00 (d, J = 12.3 Hz, 1H), 8.61 (t, J = 11.3 Hz, 1H), 7.63 (td, J = 7.6, 1.8 Hz, 1H), 7.28-7.21 (m, 1H), 7.14 (td, J = 7.5, 1.2 Hz, 1H), 6.99 (ddd, J = 10.5, 8.1, 1.2 Hz, 1H), 5.96 (s, 1H), 5.79 (br s, 1H), 3.86 (d, J = 10.6 Hz, 1H), 3.57-3.43 (m, 1H), 2.19-1.99 (m, 2H), 1.85-1.65 (m, 3H), 1.65-1.53 (m, 1H), 1.53-1.35 (m, 3H), 1.33-1.26 (m, 1H), 1.00 (t, J = 7.3 Hz, 3H).

Example 24

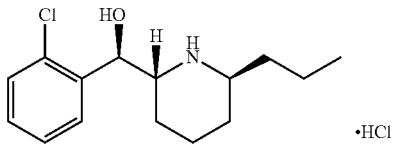 [SMILES: CCC[C@H]1CCC[C@H]([C@H](O)c2ccccc2Cl)N1 ; Cl]

(R)-(2-Chlorophenyl)((2R,6S)-6-propylpiperidin-2-yl)methanol
¹H NMR (400 MHz, CDCl₃): δ 9.13 (br s, 1H), 8.86 (br s, 1H), 7.72 (dd, J = 7.6, 1.9 Hz, 1H), 7.32 (dd, J = 7.7, 1.6 Hz, 1H), 7.30-7.19 (m, 2H), 5.59 (d, J = 8.7 Hz, 1H), 5.52 (t, J = 8.6 Hz, 1H), 3.67 (br s, 1H), 3.57 (br s, 1H), 2.13-2.01 (m, 1H), 2.00-1.89 (m, 2H), 1.84-1.56 (m, 5H), 1.55-1.41 (m, 2H), 0.95 (t, J = 7.3 Hz, 3H).

TABLE 2-continued

Example 25

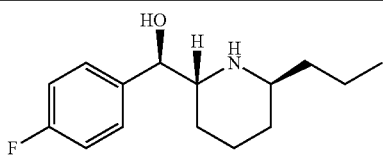

(R)-(4-Fluorophenyl)((2R,6S)-6-propylpipehdin-2-yl)methanol
$^1$H NMR (400 MHz, CDCl$_3$): δ 7.34-7.28 (m, 2H), 7.06-6.97 (m, 2H), 4.59 (d, J = 9.3 Hz, 1H), 2.86-2.74 (m, 2H), 2.64 (br s, 2H), 1.74-1.65 (m, 1H), 1.65-1.55 (m, 2H), 1.47-1.23 (m, 6H), 1.19-1.07 (m, 1H), 0.95-0.89 (m, 3H).

Example 26

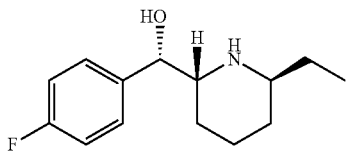 [SMILES: CC[C@H]1CCC[C@H]([C@@H](O)c2ccc(F)cc2)N1]

(S)-(4-Fluorophenyl)((2R,6S)-6-propylpiperidin-2-yl)methanol hydrochloride
$^1$H NMR (400 MHz, CDCl$_3$): δ 9.79 (d, J = 12.2 Hz, 1H), 8.51 (t, J = 11.1 Hz, 1H), 7.42-7.34 (m, 2H), 7.06-6.96 (m, 2H), 5.83 (d, J = 5.5 Hz, 1H), 5.79-5.72 (m, 1H), 3.84 (d, J = 10.9 Hz, 1H), 3.29 (t, J = 11.7 Hz, 1H), 2.17-1.94 (m, 2H), 1.80-1.60 (m, 3H), 1.64-1.54 (m, 1H), 1.50-1.31 (m, 4H), 0.99 (t, J = 7.3 Hz, 3H)

Example 27

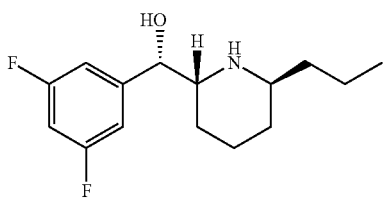 [SMILES: CCC[C@H]1CCC[C@H]([C@@H](O)c2cc(F)cc(F)c2)N1]

(S)-(3,5-Difluorophenyl)((2R,6S)-6-propylpiperidin-2-yl)methanol acetate
$^1$H NMR (400 MHz, CDCl$_3$): δ 6.92-6.83 (m, 2H), 6.66 (tt, J = 8.9, 2.4 Hz, 1H), 5.52 (s, 3H), 5.05 (d, J = 3.3 Hz, 1H), 3.42-3.37 (m, 1H), 3.13 (dt, J = 11.4, 3.3 Hz, 1H), 1.99 (s, 3H), 1.80-1.69 (m, 2H), 1.67-1.54 (m, 4H), 1.51-1.43 (m, 1H), 1.38-1.27 (m, 3H), 0.94 (t, J = 7.3 Hz, 3H)

Example 28

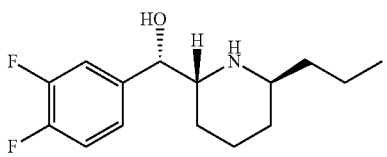 [SMILES: CCC[C@H]1CCC[C@H]([C@@H](O)c2ccc(F)c(F)c2)N1]

(S)-(3,4-Difluorophenyl)((2R,6S)-6-propylpiperidin-2-yl)methanol
$^1$H NMR (400 MHz, CDCl$_3$): δ 7.26-7.21 (m, 1H), 7.16-7.04 (m, 2H), 5.23 (d, J = 3.4 Hz, 1H), 4.34 (br s, 2H), 3.49-3.43 (m, 1H), 3.16 (dt, J = 10.9, 3.3 Hz, 1H), 1.89-1.74 (m, 2H), 1.66-1.56 (m, 4H), 1.52-1.42 (m, 1H), 1.39-1.25 (m, 3H), 0.95 (t, J = 7.3 Hz, 3H)

The compounds in Table 3 were obtained in accordance with the procedures described in Example 2 using the appropriately substituted benzaldehydes. When the title compounds are hydrochloride salts they are obtained by dissolution of the free base in Et$_2$O followed by precipitation by addition of HCl (2 M in Et$_2$O).

TABLE 3

Example 29

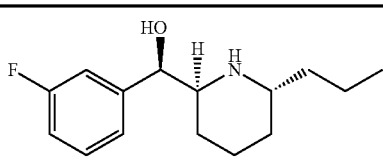

(R)-(3-Fluorophenyl)((2S,6R)-6-propylpiperidin-2-yl)methanol hydrochloride
$^1$H NMR (400 MHz, CDCl$_3$): δ 9.82 (d, J = 12.2 Hz, 1H), 8.52 (t, J = 11.3 Hz, 1H), 7.32-7.27 (m, 1H), 7.20-7.13 (m, 2H), 6.97-6.92 (m, 1H), 5.93 (br s, 1H), 5.78 (s, 1H), TABLE 3-continued 3.86 (d, J = 10.9 Hz, 1H), 3.39-3.27 (m, 1H), 2.18-2.07 (m, 1H), 2.07-1.94 (m, 1H), 1.83-1.64 (m, 3H), 1.64-1.54 (m, 1H), 1.51-1.30 (m, 4H), 1.00 (t, J = 7.3 Hz, 3H)

Example 30

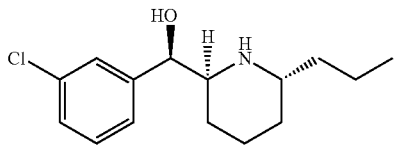 [SMILES: CCC[C@@H]1CCC[C@@H]([C@H](O)c2cccc(Cl)c2)N1]

(R)-(3-Chlorophenyl)((2S,6R)-6-propylpiperidin-2-yl)methanol hydrochloride
$^1$H NMR (400 MHz, CDCl$_3$): δ 9.82 (d, J = 11.6 Hz, 1H), 8.52 (t, J = 11.8 Hz, 1H), 7.45-7.42 (m, 1H), 7.32-7.28 (m, 1H), 7.27-7.21 (m, 2H), 5.91 (s, 1H), 5.76 (s, 1H), 3.86 (d, J = 10.8 Hz, 1H), 3.31 (t, J = 11.8 Hz, 1H), 2.18-2.07 (m, 1H), 2.07-1.94 (m, 1H), 1.82-1.65 (m, 3H), 1.65-1.54 (m, 1H), 1.51-1.29 (m, 4H), 1.01 (t, J = 7.3 Hz, 3H)

Example 31

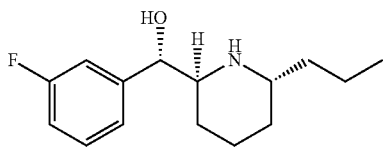 [SMILES: CCC[C@@H]1CCC[C@@H]([C@@H](O)c2cccc(F)c2)N1]

(S)-(3-Chlorophenyl)((2S,6R)-6-propylpiperidin-2-yl)methanol
$^1$H NMR (400 MHz, CDCl$_3$): δ 7.37-7.35 (m, 1H), 7.29-7.18 (m, 3H), 4.56 (d, J = 9.2 Hz, 1H), 4.41 (br s, 1H), 2.84-2.74 (m, 2H), 1.73-1.65 (m, 1H), 1.65-1.58 (m, 2H), 1.47-1.23 (m, 7H), 1.20-1.04 (m, 1H), 0.99-0.86 (m, 3H)

Example 32: 3-((R)-hydroxy((2S,6R)-6-propylpiperidin-2-yl)methyl)phenol Hydrochloride

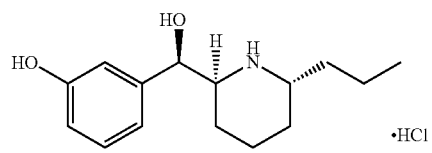 [SMILES: CCC[C@@H]1CCC[C@@H]([C@H](O)c2cccc(O)c2)N1 ; Cl]

The title compound was prepared from tert-butyl (R)-2-propylpiperidine-1-carboxylate and 3-benzyloxybenzaldehyde in accordance with the procedure in Example 2, Step (d), followed by the removal of the protecting groups as described in Example 2, Step (c) and Example 5, Step (c), but using iPrOH as a solvent in the last step. The hydrochloride salt was obtained by dissolution of the free base in Et$_2$O followed by precipitation by addition of HCl (2 M in Et$_2$O).

$^1$H NMR (400 MHz, D$_2$O): 7.41-7.34 (m, 1H), 7.01-6.98 (m, 1H), 6.96-6.91 (m, 2H), 4.94 (d, J=5.6 Hz, 1H), 3.65-3.58 (m, 1H), 3.58-3.51 (m, 1H), 1.88-1.75 (m, 4H), 1.75-1.66 (m, 2H), 1.66-1.55 (m, 2H), 1.45-1.34 (m, 1H), 1.34-1.22 (m, 1H), 0.94 (t, J=7.3 Hz, 3H).

Example 33: 3-((S)-hydroxy((2S,6R)-6-propylpiperidin-2-yl)methyl)phenol Hydrochloride

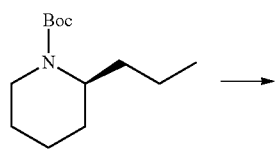

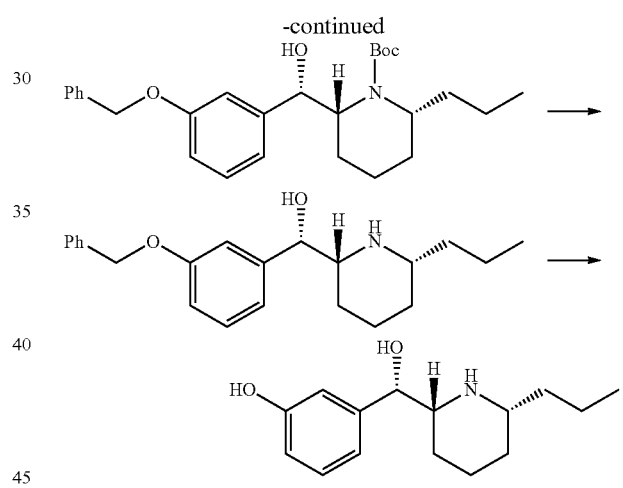

The title compound was prepared from tert-butyl (R)-2-propylpiperidine-1-carboxylate and 3-benzyloxybenzaldehyde in accordance with the procedure in Example 2, Step (b), followed by the removal of the Boc-protecting groups as described in Example 2, Step (c).

The benzyloxy group was then removed by adding Pd—C (10%, 52 mg, 0.049 mmol) and triethylsilane (390 μL, 2.44 mmol) to a solution of the intermediate (S)-(3-(benzyloxy)-phenyl)((2R,6R)-6-propylpiperidin-2-yl)methanol (83 mg, 0.24 mmol) in MeOH (4 mL). The mixture was stirred at rt for 10 min, filtered through Celite and concentrated. The residue was dissolved in MeOH (1 mL), filtered through Celite and concentrated. The residue was was dissolved in E$_2$O (10 mL) and HCl (2M in E$_2$O, 147 μL, 0.29 mmol) was added dropwise. The mixture was stirred at rt for 15 min, filtered, washed with E$_2$O and dried in air to give the title compound (60 mg, 86%).

1H NMR (400 MHz, CD$_3$OD): δ 7.25-7.20 (m, 1H), 6.91-6.86 (m, 2H), 6.81-6.77 (m, 1H), 4.75 (d, J=9.6 Hz,

1H), 3.52-3.43 (m, 1H), 3.40-3.34 (m, 1H), 2.02-1.90 (m, 1H), 1.84-1.61 (m, 5H), 1.61-1.55 (m, 1H), 1.55-1.39 (m, 3H), 1.04 (t, J=7.3 Hz, 3H).

Examples 34 to 38

The title compounds in Table 4 were prepared from tert-butyl (2S,6S)-2-formyl-6-propyl-piperidine-1-carboxylate [prepared in accordance with the procedure in Examples 1 (a) and (b) from tert-butyl (S)-2-propylpiperidine-1-carboxylate] and the appropriately substituted phenylmagnesium bromide in accordance with the procedure in Example 1, Steps (c) and (d). For Examples 37 and 38, the benzyl protecting group was removed in accordance with the procedure in Example 33. Hydrochloride salts were obtained by dissolution of the free base in Et$_2$O followed by precipitation by addition of HCl (2 M in Et$_2$O).

TABLE 4

Example 34

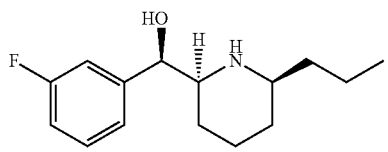 [SMILES: CCC[C@H]1CCC[C@@H]([C@H](O)c2cccc(F)c2)N1]

(R)-(3-Fluorophenyl)((2S,6S)-6-propylpiperidin-2-yl)methanol hydrochloride
$^1$H NMR (400 MHz, CDCl$_3$): δ 10.04 (br s, 1H), 7.68 (br s, 1H), 7.28-7.16 (m, 3H), 6.94-6.88 (m, 1H), 5.74 (s, 1H), 5.35 (br s, 1H), 3.28 (t, J = 11.7 Hz, 1H), 3.17-3.04 (m, 1H), 2.08-1.98 (m, 1H), 1.97-1.91 (m, 1H), 1.90-1.79 (m, 2H), 1.78-1.66 (m, 1H), 1.54-1.39 (m, 3H), 1.39-1.20 (m, 2H), 0.79 (t, J = 7.3 Hz, 3H).

Example 35

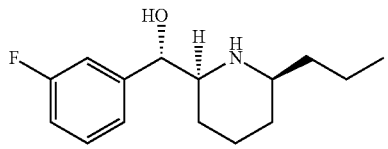 [SMILES: CCC[C@H]1CCC[C@@H]([C@@H](O)c2cccc(F)c2)N1]

(S)-(3-Fluorophenyl)((2S,6S)-6-propylpiperidin-2-yl)methanol hydrochloride
$^1$H NMR (400 MHz, CDCl$_3$): δ 9.8-9.60 (m, 1H), 8.15-7.90 (m, 1H), 7.30-7.22 (m, 1H), 7.17-7.07 (m, 2H), 7.00-6.93 (m, 1H), 6.00 (br s, 1H), 4.96 (d, J = 9.6 Hz, 1H), 3.34 (q, J = 10.6 Hz, 1H), 3.09-2.96 (m, 1H), 2.04-1.61 (m, 6H), 1.52-1.21 (m, 4H), 0.82 (t, J = 7.3 Hz, 3H)

Example 36

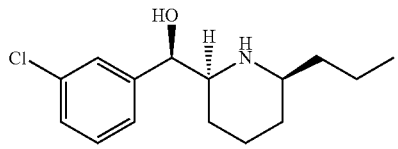 [SMILES: CCC[C@H]1CCC[C@@H]([C@H](O)c2cccc(Cl)c2)N1]

(R)-(3-Chlorophenyl)((2S,6S)-6-propylpiperidin-2-yl)methanol hydrochloride
$^1$H NMR (400 MHz, CDCl$_3$): δ 10.06 (br s, 1H), 7.67 (br s, 1H), 7.48-7.44 (m, 1H), 7.36-7.29 (m, 1H), 7.25-7.16 (m, 2H), 5.73 (s, 1H), 5.27 (br s, 1H), 3.26 (t, J = 11.7 Hz, 1H), 3.18-3.04 (m, 1H), 2.08-1.99 (m, 1H), 1.98-1.91 (m, 1H), 1.91-1.80 (m, 2H), 1.78-1.66 (m, 1H), 1.53-1.40 (m, 3H), 1.40-1.21 (m, 2H), 0.80 (t, J = 7.3 Hz, 3H)

Example 37

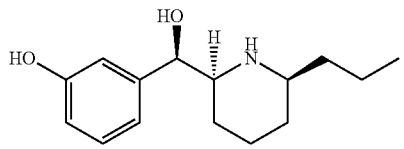 [SMILES: CCC[C@H]1CCC[C@@H]([C@H](O)c2cccc(O)c2)N1]

(R)-(3-Hydroxyphenyl)((2S, 6S)-6-propylpiperidin-2-yl)methanol
$^1$H NMR (400 MHz, CDCl$_3$): δ 7.15 (t, J = 8.0 Hz, 1H), 6.83-6.76 (m, 2H), 6.74-6.69 (m, 1H), 4.85 (br s, 3H), 4.54 (d, J = 5.3 Hz, 1H), 2.78-2.69 (m, 1H), 2.54-2.43 (m, 1H), 1.85-1.74 (m, 1H), 1.71-1.57 (m, 2H), 1.36-1.11 (m, 6H), 1.04-0.93 (m, 1H), 0.79 (t, J = 7.0 Hz, 3H)

Example 38

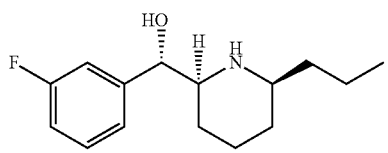 [SMILES: CCC[C@H]1CCC[C@@H]([C@@H](O)c2cccc(F)c2)N1]

(S)-(3-Hydroxyphenyl)((2S,6S)-6-propylpiperidin-2-yl)methanol hydrochloride
$^1$H NMR (400 MHz, CDCl$_3$): δ 7.25-7.19 (m, 1H), 6.89-6.84 (m, 2H), 6.81-6.77 (m, 1H), 4.46 (d, J = 9.3 Hz, 1H), 3.24-3.16 (m, 1H), 3.14-3.05 (m, 1H), 2.12-2.04 (m, 1H), 1.90-1.80 (m, 2H), 1.64-1.47 (m, 3H), 1.47-1.25 (m, 4H), 1.02 (t, J = 7.2 Hz, 3H)

Example 39: (S)-(3-Fluorophenyl)((2R,5R)-5-propylpyrrolidin-2-yl)methanol Hydrochloride

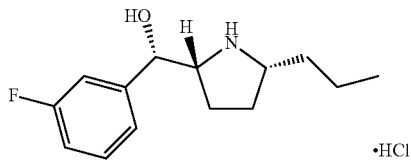 [SMILES: CCC[C@@H]1CC[C@H]([C@@H](O)c2cccc(F)c2)N1 ; Cl]

The title compound was prepared in accordance with the procedure in Example 7. The intermediate benzyl (2R,5R)-2-((S)-(3-fluorophenyl)(hydroxy)methyl)-5-propylpyrrolidine-1-carboxylate was obtained in the chromatographic purification in Example 7, Step (f). The hydrochloride salt was obtained by dissolution of the free base in Et$_2$O followed by precipitation by addition of HCl (2 M in Et$_2$O).

Example 40: 3-((S)-Hydroxy((2R,5R)-5-propylpyrrolidin-2-yl)methyl)phenol

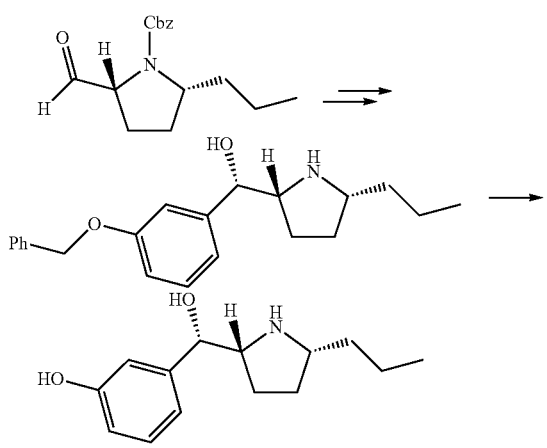

The title compound was prepared in accordance with the procedures in Examples 5 and 7. The intermediate (S)-(3-(benzyloxy)phenyl)((2R,5R)-5-propylpyrrolidin-2-yl)methanol was obtained from the reaction between 3-benzyloxymagnesium bromide and benzyl (2R,5R)-2-formyl-5-propylpyrrolidine-1-carboxylate and chromatographic purification as described in Example 7, Step (f), followed by debenzylation in accordance with the procedure in Example 5, Step (c).

Example 41: (R)-(3-fluorophenyl)((2S,5S)-5-propylpyrrolidin-2-yl)methanol Hydrochloride

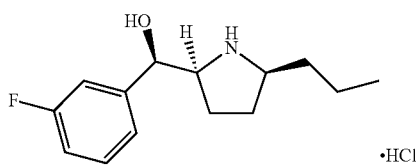 [SMILES: CCC[C@H]1CC[C@@H]([C@H](O)c2cccc(F)c2)N1 ; Cl]

(a) Benzyl (2R,5S)-2-(hydroxycarbamoyl)-5-propylpyrrolidine-1-carboxylate

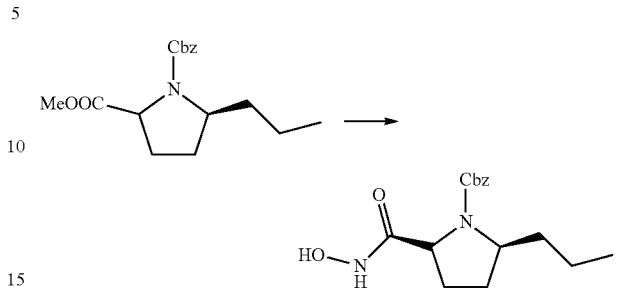

iPrMgCl (2M in THF, 1.35 mL, 2.69 mmol) was added dropwise to a mixture of 1-benzyl 2-methyl (2S,5S)-5-propylpyrrolidine-1,2-dicarboxylate (prepared in accordance with the procedures in Example 7, Steps (a) to (c) from methyl (S)-5-oxopyrrolidine-2-carboxylate) and N,O-dimethylhydroxylamine hydrochloride (197 mg, 2.02 mmol) in THF at −20° C. The mixture was stirred for 20 min at −10° C. N,O-Dimethylhydroxylamine hydrochloride (197 mg, 2.02 mmol) was added followed by dropwise addition of iPrMgCl (2M in THF, 1.35 mL, 2.69 mmol) at −20° C. The mixture was stirred for 10 min at −10° C. NH$_4$Cl (aq, sat, 4 mL) was added and the mixture was extracted with EtOAc. The combined extracts were washed with brine, dried (Na$_2$SO$_4$), filtered and concentrated to give the sub-title compound (393 mg, 98%), which was used in the next step without further purification.

(b) Benzyl (2S,5S)-2-(3-fluorobenzoyl)-5-propylpyrrolidine-1-carboxylate

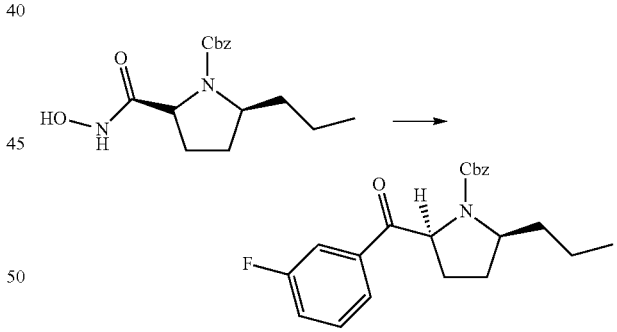

Benzyl (2S,5S)-2-(methoxy(methyl)carbamoyl)-5-propylpyrrolidine-1-carboxylate (195 mg, 0.58 mmol) in THF (1.4 mL) was added to a mixture of CeCl$_3$ (489 mg, 1.98 mmol) and THF (2.5 mL) at rt. The mixture was vigorously stirred at rt for 1 h and cooled in an ice bath. (3-Fluorophenyl)magnesium bromide (1M in THF, 1.75 mL, 1.75 mmol) was added dropwise, the ice bath removed and the mixture stirred at rt for 1 h. NH$_4$Cl (aq, sat, 5 mL) followed by H$_2$O were added and the aq phase was extracted with EtOAc. The combined organic phases were washed with brine, dried (Na$_2$SO$_4$), filtered and concentrated. The residue was purified by chromatography to give the sub-title compound (107 mg, 50%).

(c) Benzyl (2 S, 5S)-2-((R)-(3-fluorophenyl)(hydroxy)methyl)-5-propyl pyrrolidine-1-carboxylate and Benzyl (2S,5S)-2-((S)-(3-fluorophenyl)(hydroxy)methyl)-5-propyl-pyrrolidine-1-carboxylate

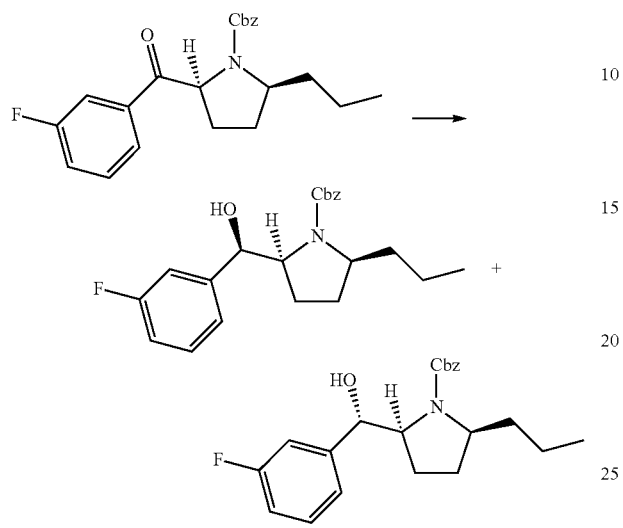

NaBH$_4$ (15.4 mg, 0.41 mmol) was added to a solution of benzyl (2S,5S)-2-(3-fluoro-benzoyl)-5-propylpyrrolidine-1-carboxylate (100 mg, 0.271 mmol) in MeOH:THF (9:1, 6 mL) at 0° C. Ice-bath was removed and the mixture was stirred at rt for 2 h. H$_2$O was added and the aq layer extracted with EtOAc. The combined organic phases were washed with brine, dried (Na$_2$SO$_4$), filtered and concentrated. The residue was purified by chromatography to give the sub-title compounds (22 mg, 22%) and (68 mg, 68%).

(d) (R)-(3-Fluorophenyl)((2S,5S)-5-propylpyrrolidin-2-yl)methanol Hydrochloride

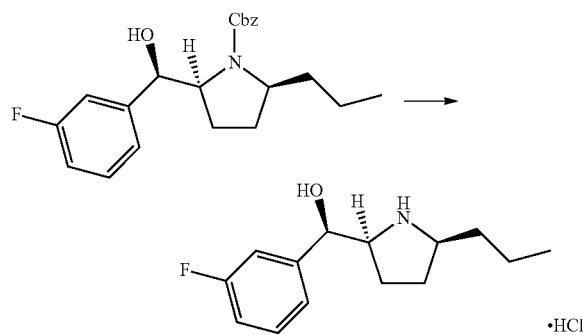

A mixture of benzyl (2S,5S)-2-((R)-(3-fluorophenyl)(hydroxy)methyl)-5-propylpyrrolidine-1-carboxylate (22 mg, 0.0592 mmol), Pd—C (10%, 6.3 mg, 0.0059 mmol) and iPrOH (3 ml) was hydrogenated (rt, 5 bar) for 40 min and filtered through Celite. The filtrate was concentrated and dissolved in Et$_2$O (10 ml). HCl (2M in Et$_2$O, 36 μl, 0.071 mmol) was added. The solids were collected and dried to give the title compound (12 mg, 74%).

$^1$H NMR (400 MHz, D$_2$O) δ 7.53-7.44 (m, 2H), 7.30-7.20 (m, 2H), 7.20-7.12 (m, 1H), 5.07 (d, J=5.4 Hz, 1H), 4.02-3.90 (m, 1H), 3.70-3.56 (m, 1H), 2.31-2.16 (m, 1H), 2.13-1.95 (m, 2H), 1.84-1.61 (m, 3H), 1.48-1.31 (m, 2H), 0.93 (t, J=7.4 Hz, 3H).

Example 42: (S)-(3-Fluorophenyl)((2S,5S)-5-propylpyrrolidin-2-yl)methanol Hydrochloride

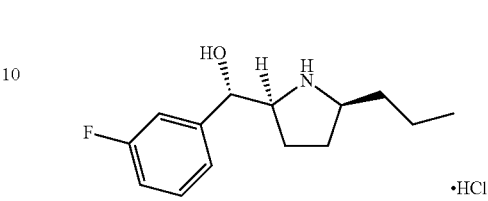

The title compound was prepared from benzyl (2S,5S)-2-((S)-(3-fluorophenyl)(hydroxy)-methyl)-5-propylpyrrolidine-1-carboxylate (see Example 41, Step (c), in accordance with the procedure in Example 41, Step (d).

Example 43: (R)-(3-Fluorophenyl)((2S,5R)-5-propylpyrrolidin-2-yl)methanol Hydrochloride

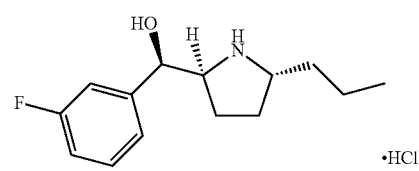 [SMILES: CCC[C@@H]1CC[C@@H]([C@H](O)c2cccc(F)c2)N1 ; Cl]

(a) 1-Benzyl 2-methyl (2S)-5-hydroxypyrrolidine-1,2-dicarboxylate

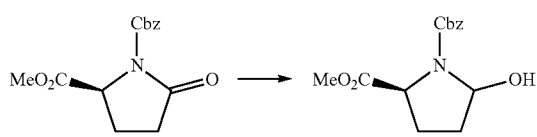 [SMILES: COC(=O)[C@@H]1CCC(=O)N1C(=O)OCc1ccccc1 ; COC(=O)[C@@H]1CCC(O)N1C(=O)OCc1ccccc1]

Lithium triethyl borohydride (1.7M in THF, 1.27 mL, 2.16 mmol) was added to a stirred solution of 1-benzyl 2-methyl (S)-5-oxopyrrolidine-1,2-dicarboxylate (500 mg, 1.80 mmol) in THF (14 mL) at −78° C. The mixture was stirred for 30 min at −78° C. NaHCO$_3$ (aq, sat) was added and the temperature was allowed to reach rt. EtOAc was added and the aq phase extracted with EtAOc. The combined organic phases were washed with brine, dried (Na$_2$SO$_4$) and concentrated to give the sub-title product (496 mg, 99%), which was used in the next step without further purification.

(b) 1-Benzyl 2-methyl (2S)-5-methoxypyrrolidine-1,2-dicarboxylate

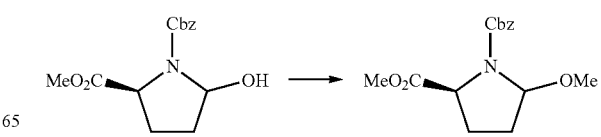

p-Toluenesulfonic acid monohydrate (41 mg, 0.21 mmol) was added to a stirred solution of 1-benzyl 2-methyl (2S)-5-hydroxypyrrolidine-1,2-dicarboxylate (600 mg, 2.15 mmol) in MeOH (6.5 mL) The mixture was stirred overnight. NaHCO$_3$ (aq, sat) was added and the MeOH was removed in vacuo. The residue was extracted with Et$_2$O and the combined organic phases were washed with brine, dried (Na$_2$SO$_4$) and concentrated to give the sub-title product (557 mg, 88%), which was used in the next step without further purification.

(c) 1-Benzyl 2-methyl (2S,5R)-5-propylpyrrolidine-1,2-dicarboxylate

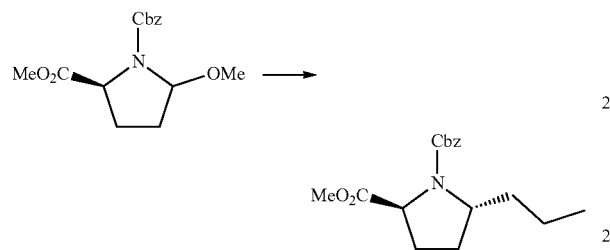

nPrMgCl (1M in THF, 8.59 mL, 8.59 mmol) was added dropwise to a stirred mixture of CuBr.SMe$_2$ (1.77 g, 8.59 mmol) in THF (16 mL) at −40° C. After 45 min at −40° C., the mixture was cooled to −78° C. BF$_3$.OEt$_2$ (1.08 mL, 8.59 mmol) was added dropwise, followed after 30 min stirring at −78° C. by a solution of 1-benzyl 2-methyl (2S)-5-methoxy-pyrrolidine-1,2-dicarboxylate (557 mg, 1.90 mmol) in THF (3 mL). The mixture was stirred for 15 min and allowed to reach room temperature over 1.5 h. A 1:1 mixture (15 mL) of NH$_4$Cl (aq, sat) and NH$_3$ (aq, conc) was added and the mixture was vigorously stirred at rt for 1 h. The phases were separated and the aq phase was extracted with Et$_2$O. The combined extracts were washed with NaHCO$_3$, dried (Na$_2$SO$_4$) and concentrated. The residue was purified by chromatography to give the sub-title compound (456 mg, 79%) containing 8% 1-benzyl 2-methyl (2S,5S)-5-propylpyrrolidine-1,2-dicarboxylate.

(d) Benzyl (2S,5R)-2-(methoxy(methyl)carbamoyl)-5-propylpyrrolidine-1-carboxylate

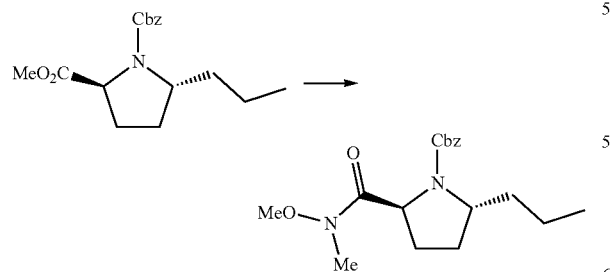

iPrMgCl (2M in THF, 1.45 mL, 2.91 mmol) was added dropwise to a stirred mixture of N,O-dimethylhydroxylamine hydrochloride (213 mg, 2.19 mmol), 1-benzyl 2-methyl (2S,5R)-5-propylpyrrolidine-1,2-dicarboxylate (445 mg, 1.45 mmol) and THF (6 mL) at −20° C. The mixture was stirred for 20 min at −10° C. and cooled to −20° C. Another portion of N,O-dimethylhydroxylamine hydrochloride (445 mg, 1.45 mmol) was added followed by dropwise addition of iPrMgCl (2M in THF, 1.45 mL, 2.91 mmol). The mixture was stirred for 10 min at −10° C. NH$_4$Cl (aq, sat, 4 mL) was added and the mixture extracted with EtOAc. The combined organic phases were washed with brine, dried (Na$_2$SO$_4$), filtered and concentrated to give the sub-title product (472 mg, 97%), which was used in the next step without further purification.

(e) Benzyl (2S,5R)-2-(3-fluorobenzoyl)-5-propylpyrrolidine-1-carboxylate

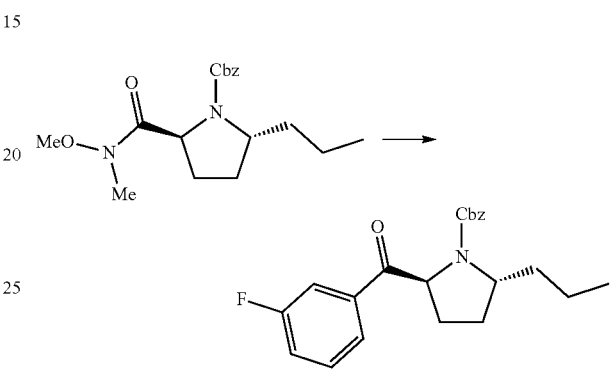

The sub-title compound was prepared from benzyl (2S,5R)-2-(methoxy(methyl)-carbamoyl)-5-propylpyrrolidine-1-carboxylate and 3-fluorophenylmagnesium bromide in accordance with the procedure in Example 7, Step (f).

(f) Benzyl (2S,5R)-2-((R)-(3-fluorophenyl)(hydroxy)methyl)-5-propylpyrrolidine-1-carboxylate and Benzyl (2S,5R)-2-((S)-(3-fluorophenyl)(hydroxy)methyl)-5-propyl-pyrrolidine-1-carboxylate

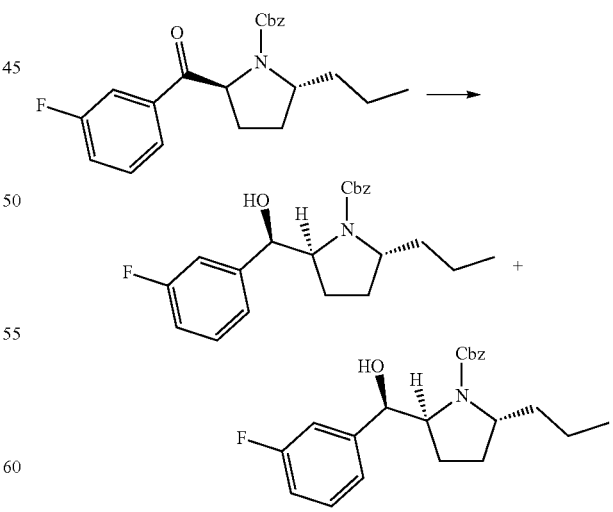

The sub-title compound was prepared from benzyl (2S,5R)-2-(3-fluorobenzoyl)-5-propyl-pyrrolidine-1-carboxylate in accordance with the procedure in Example 41, Step (c).

(g) (R)-(3-Fluorophenyl)((2S,5R)-5-propylpyrrolidin-2-yl)methanol Hydrochloride

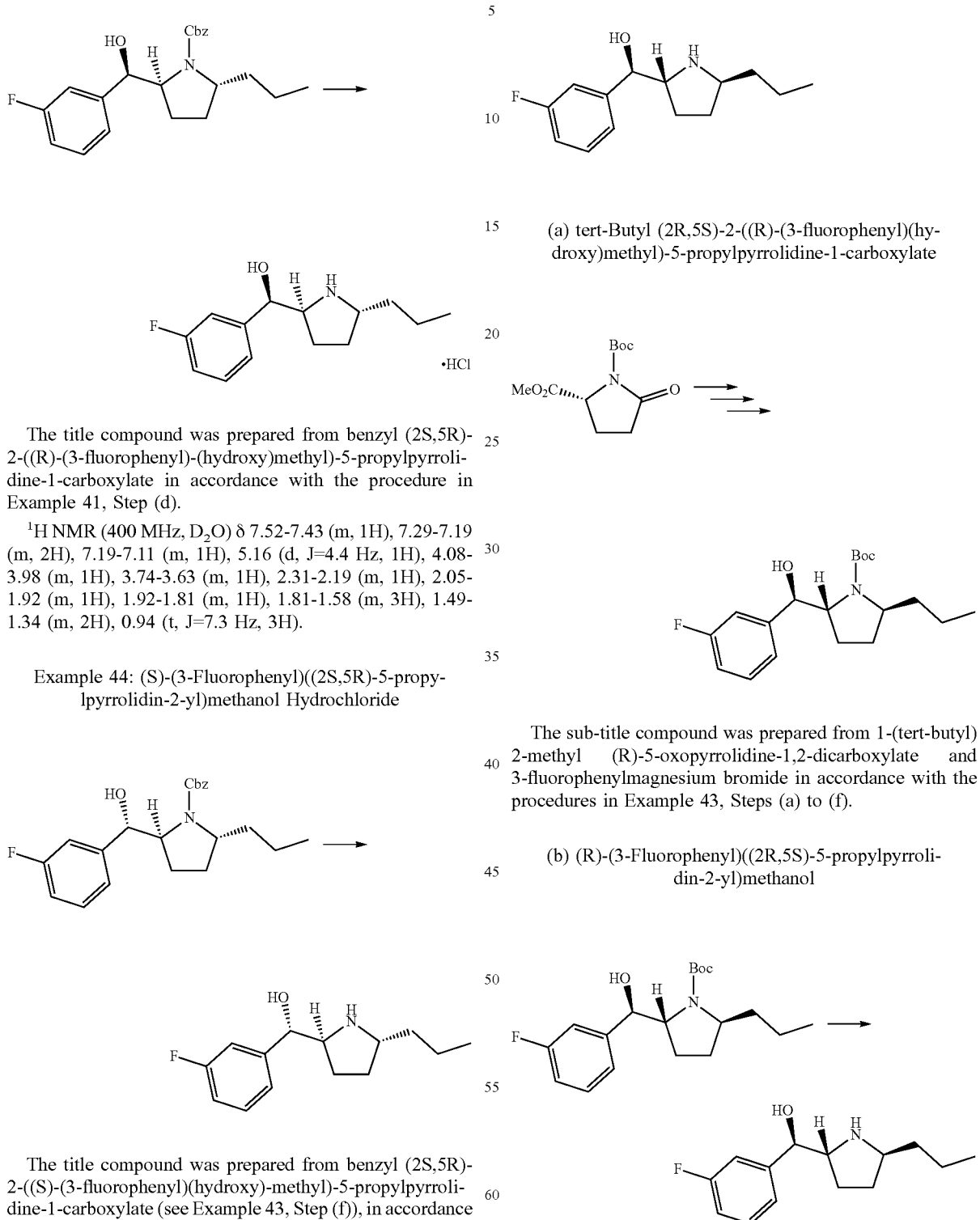

The title compound was prepared from benzyl (2S,5R)-2-((R)-(3-fluorophenyl)-(hydroxy)methyl)-5-propylpyrrolidine-1-carboxylate in accordance with the procedure in Example 41, Step (d).

$^1$H NMR (400 MHz, D$_2$O) δ 7.52-7.43 (m, 1H), 7.29-7.19 (m, 2H), 7.19-7.11 (m, 1H), 5.16 (d, J=4.4 Hz, 1H), 4.08-3.98 (m, 1H), 3.74-3.63 (m, 1H), 2.31-2.19 (m, 1H), 2.05-1.92 (m, 1H), 1.92-1.81 (m, 1H), 1.81-1.58 (m, 3H), 1.49-1.34 (m, 2H), 0.94 (t, J=7.3 Hz, 3H).

Example 44: (S)-(3-Fluorophenyl)((2S,5R)-5-propylpyrrolidin-2-yl)methanol Hydrochloride The title compound was prepared from benzyl (2S,5R)-2-((S)-(3-fluorophenyl)(hydroxy)-methyl)-5-propylpyrrolidine-1-carboxylate (see Example 43, Step (f)), in accordance with the procedure in Example 41, Step (d).

$^1$H NMR (400 MHz, D$_2$O) δ 77.52-7.42 (m, 1H), 7.31-7.21 (m, 2H), 7.20-7.12 (m, 1H), 4.82 (d, J=8.6 Hz, 1H, overlapping), 4.00-3.87 (m, 1H), 3.79-3.66 (m, 1H), 2.33-2.20 (m, 1H), 1.92-1.60 (m, 5H), 1.51-1.34 (m, 2H), 0.95 (t, J=7.4 Hz, 3H).

Example 45: (R)-(3-Fluorophenyl)((2R,5S)-5-propylpyrrolidin-2-yl)methanol (a) tert-Butyl (2R,5S)-2-((R)-(3-fluorophenyl)(hydroxy)methyl)-5-propylpyrrolidine-1-carboxylate The sub-title compound was prepared from 1-(tert-butyl) 2-methyl (R)-5-oxopyrrolidine-1,2-dicarboxylate and 3-fluorophenylmagnesium bromide in accordance with the procedures in Example 43, Steps (a) to (f).

(b) (R)-(3-Fluorophenyl)((2R,5S)-5-propylpyrrolidin-2-yl)methanol

The title compound was prepared from tert-butyl (2R,5S)-2-((R)-(3-fluorophenyl)(hydroxy)-methyl)-5-propylpyrrolidine-1-carboxylate in accordance with the procedure in Example 2, Step (c).

Example 46: 3-((R)-hydroxy((2R,5S)-5-propylpyrrolidin-2-yl)methyl)phenol

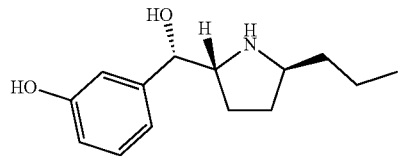 [SMILES: CCC[C@H]1CC[C@H]([C@@H](O)c2cccc(O)c2)N1]

(a) tert-butyl (2R,5S)-2-((R)-(3-(benzyloxy)phenyl)(hydroxy)methyl)-5-propylpyrrolidine-1-carboxylate

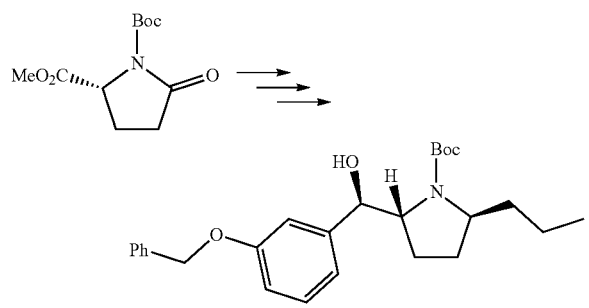

The sub-title compound was prepared from 1-(tert-butyl) 2-methyl (R)-5-oxopyrrolidine-1,2-dicarboxylate and 3-benzyloxyphenylmagnesium bromide in accordance with the procedures in Example 43, Steps (a) to (f).

(b) 3-((R)-hydroxy((2R,5S)-5-propylpyrrolidin-2-yl)methyl)phenol

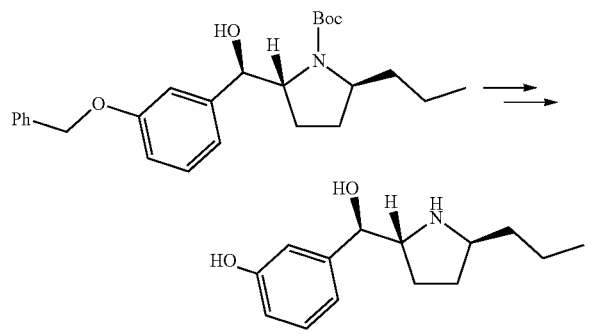

The title compound was prepared from tert-butyl (2R,5S)-2-((R)-(3-(benzyloxy)phenyl)-(hydroxy)methyl)-5-propylpyrrolidine-1-carboxylate in accordance with the procedures in Example 45, Step (b) and Example 33.

$^1$H NMR (300 MHz, CDCl$_3$) δ 7.17-7.09 (m, 1H), 6.98-6.90 (m, 1H), 6.78-6.69 (m, 2H), 4.91-4.30 (br. s, 3H), 4.23 (d, J=8.1 Hz, 1H), 3.47-3.35 (m, 1H), 3.19-3.07 (m, 1H), 2.00-1.88 (m, 1H), 1.71-1.58 (m, 1H), 1.56-1.42 (m, 2H), 1.42-1.17 (m, 4H), 0.91 (t, J=7.0 Hz, 3H).

Example 47: (R)-(3-Chlorophenyl)((2R,5R)-5-propylpyrrolidin-2-yl)methanol Maleate

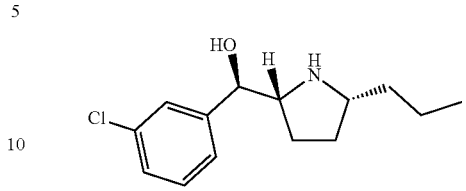

(a) Methyl (R)-2-((tert-butoxycarbonyl)amino)-5-oxooctanoate

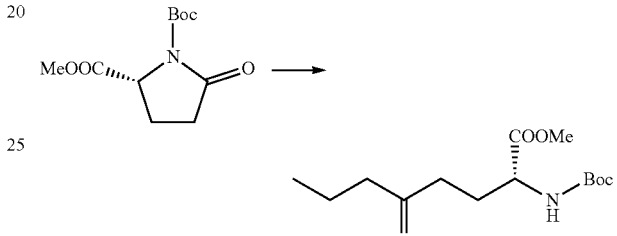

The sub-title compound was prepared from 1-(tert-butyl) 2-methyl (R)-5-oxopyrrolidine-1,2-dicarboxylate and n-propylmagnesium chloride in accordance with the procedure in Example 7, Step (b).

(b) 1-(tert-Butyl) 2-methyl (2R,5R)-5-propylpyrrolidine-1,2-dicarboxylate

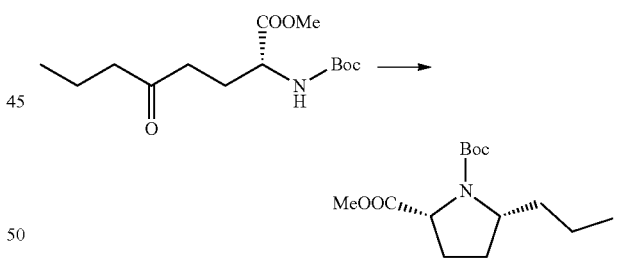

TFA (1.34 mL, 17.4 mmol) was added to a solution of methyl (R)-2-((tert-butoxycarbonyl)-amino)-5-oxooctanoate (500 mg, 1.74 mmol) in CH$_2$Cl$_2$ (1.5 mL) at rt and the mixture was stirred at rt and concentrated. The residue was dissolved in i-PrOH (97 mL), and Pd/C (10%, 93 mg, 0.087 mmol) was added. The mixture was hydrogenated at 8 atm for 2 h, filtered through Celite and concentrated. The residue was dissolved in CH$_2$Cl$_2$ (10 mL) and triethylamine (485 µL, 3.48 mmol) and DMAP (43 mg, 0.35 mmol) were added, followed by Boc$_2$O (950 mg, 4.35 mmol). The mixture was stirred at rt overnight, then washed with HCl (aq, 1 M) and brine, dried (Na$_2$SO$_4$) and concentrated. The residue was purified by chromatography to give the sub-title compound (422 mg, 89%).

(c) (R)-(3-Chlorophenyl)((2R,5R)-5-propylpyrrolidin-2-yl)methanol Maleate

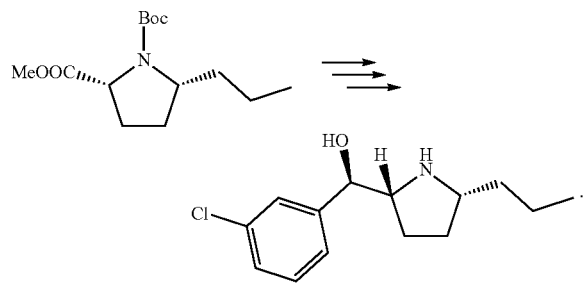

Maleic Acid

The title compound was prepared in accordance with the procedures in Example 7, Steps (d) to (f) and Example 2, Step (c) from 1-(tert-butyl) 2-methyl (2R,5R)-5-propylpyrrolidine-1,2-dicarboxylate and 3-chlorophenyl magnesium bromide. The maleate salt was prepared by adding maleic acid (25 mg, 0.21 mmol) in EtOAc (0.8 mL) to a solution of the free base (42.7 mg, 0.18 mmol) in EtOAc (0.2 mL), concentration and reverse phase chromatography.

$^1$H NMR (400 MHz, CD$_3$OD): δ 7.72-7.67 (m, 1H), 7.46-7.38 (m, 2H), 7.37-7.29 (m, 1H), 6.26-6.23 (m, 2H), 5.31 (d, J=7.6 Hz, 1H), 3.90-3.82 (m, 1H), 3.58-3.47 (m, 1H), 2.29-2.18 (m, 1H), 2.03-1.63 (m, 5H), 1.52-1.37 (m, 2H), 1.00 (t, 3H).

Example 48: (R)-(3-Chlorophenyl)((2R,5R)-5-propylpyrrolidin-2-yl)methanol Maleate

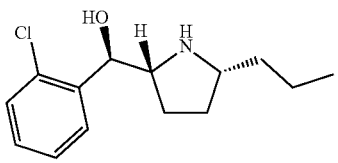 [SMILES: CCC[C@@H]1CC[C@H]([C@H](O)c2ccccc2Cl)N1]

The title compound was prepared in accordance with the procedure in Example 48 from 1-(tert-butyl) 2-methyl (R)-5-oxopyrrolidine-1,2-dicarboxylate, n-propylmagnesium and 3-chlorophenyl magnesium bromide.

BIOLOGICAL EXAMPLES

L6-myoblasts were grown in Dulbecco's Modified Eagle's Medium (DMEM) containing 4.5 g/l glucose supplemented with 10% fetal bovine serum, 2 mM L-Glutamine, 50 U/ml penicillin, 50 μg/ml streptomycin and 10 mM HEPES. Cells were plated at 1×10$^5$ cells per ml in 24-well plates. After reaching 90% confluence the cells were grown in medium containing 2% FBS for 7 days where upon cells differentiated into myotubes.

Biological Example 1: Glucose Uptake

Differentiated L6-myotubes were serum-starved over night in medium containing 0.5% fatty-acid free BSA and stimulated with agonist, final concentration 1×10$^{-5}$. After 1 h 40 min cells were washed with warm, glucose free medium or PBS and another portion of agonist was added to glucose free medium. After 20 min the cells were exposed to 50 nM $^3$H-2-deoxy-glucose for another 10 min before washed in ice cold glucose free medium or PBS and lysed in 0.2 M NaOH for 1 h in 60° C. Cell lysate was mixed with scintillation buffer (Emulsifier Safe, Perkin Elmer and radioactivity detected in a β-counter (Tri-Carb 2800TR, Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with −.

Biological Example 2: Measurement of Intracellular cAMP Levels

Differentiated cells were serum-starved over night and stimulated with agonist, final concentration 1×10-$^5$, for 15 min in stimulation buffer (HBSS supplemented with 1% BSA, 5 mM HEPES and 1 mM IBMX, pH 7.4) The medium was then aspirated and to end the reaction 100 μL of 95% EtOH was added to each well of a 24-well plate and cells were kept in −20° C. over night. The EtOH was let to evaporate and 500 μL of lysis buffer (1% BSA, 5 mM HEPES and 0.3% Tween-20, pH 7.4) was added to each well before put in −80° C. for 30 min and then kept in −20° C. Intracellular cAMP levels were detected using an alpha screen cAMP kit (6760635D from Perkin Elmer). The activity for each compound is compared to that of isoproterenol. If a compound shows activity of more than 75% of that of isoproterenol, the activity is denoted with +++, if it is between 75 and 50% it is denoted with ++; if it is between 50 and 25% it is denoted with +; if it less than 25% it is denoted with −.

Using the assays described in Biological Examples 1 and 2 the following results were obtained.

| Compound example no. | Biological example 1 | Biological example 2 |
|---|---|---|
| 1 | + | − |
| 2 | +++ | − |
| 3 | +++ | − |
| 4 | ++ | − |
| 5 | +++ | − |
| 6 | ++ | − |
| 7 | +++ | − |
| 8 | +++ | + |
| 9 | ++ | − |
| 10 | +++ | − |
| 11 | + | − |
| 12 | ++ | − |
| 13 | ++ | − |
| 14 | + | − |
| 15 | ++ | − |
| 16 | ++ | − |
| 17 | + | − |
| 18 | ++ | − |
| 19 | + | − |
| 20 | + | − |
| 21 | + | − |
| 22 | ++ | − |
| 23 | + | − |
| 24 | + | − |
| 25 | ++ | − |
| 26 | + | − |
| 27 | + | − |
| 28 | + | − |
| 29 | + | − |
| 30 | +++ | − |
| 31 | + | − |
| 32 | +++ | − |
| 33 | ++ | − |

| Compound example no. | Biological example 1 | Biological example 2 |
| --- | --- | --- |
| 34 | ++ | − |
| 35 | + | − |
| 36 | + | − |
| 37 | ++ | − |
| 38 | +++ | − |
| 39 | ++ | − |
| 40 | + | − |
| 41 | ++ | − |
| 42 | ++ | − |
| 43 | + | − |
| 44 | ++ | − |
| 45 | ++ | − |
| 46 | ++ | − |
| 47 | ++ | − |
| 48 | +++ | − |

The invention claimed is:

1. A compound of formula IF:

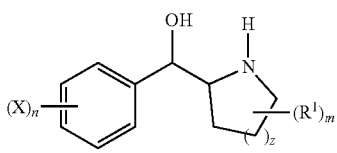

(IA)

or a pharmaceutically acceptable salt thereof, wherein:
z represents 0, 1 or 2;
when z represents 0 then m represents 0 to 5, or when z represents 1 then m represents 1 to 7 or when z represents 2 then m represents 0 to 9;
each $R^1$ independently represents $C_{1-6}$ alkyl, $C_{2-6}$ alkenyl, or $C_{2-6}$ alkynyl each optionally substituted by one or more halo;
each X independently represents halo, $R^a$, —CN, —N$_3$, —N(R$^b$)R$^c$, —NO$_2$, —ONO$_2$, —OR$^d$, —S(O)$_p$R$^e$ or —S(O)$_q$N(R$^f$)R$^g$;
$R^a$ represents $C_{1-6}$ alkyl, $C_{2-6}$ alkenyl, or $C_{2-6}$ alkynyl each optionally substituted by one or more groups independently selected from G;
each R$^b$, R$^c$, R$^d$, R$^e$, R$^f$ and R$^g$ independently represents H or $C_{1-6}$ alkyl, $C_{2-6}$ alkenyl, or $C_{2-6}$ alkynyl each optionally substituted by one or more groups independently selected from G;
or alternatively any of R$^b$ and R$^c$ and/or R$^f$ and R$^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O,
wherein the $C_{1-3}$ alkyl, $C_{2-3}$ alkenyl, and $C_{2-3}$ alkynyl each are optionally substituted by one or more halo;
G represents halo, —CN, —N(R$^{a1}$)R$^{b1}$, —OR$^{c1}$, —S(O)$_p$R$^{d1}$, —S(O)$_q$N(R$^{e1}$)R$^{f1}$ or =O;
each R$^{a1}$, R$^{b1}$, R$^{c1}$, R$^{d1}$, R$^{e1}$ and R$^{f1}$ independently represents H or $C_{1-6}$ alkyl, $C_{2-6}$ alkenyl, or $C_{2-6}$ alkynyl each optionally substituted by one or more halo;
or alternatively any of R$^{a1}$ and R$^{b1}$ and/or R$^{e1}$ and R$^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O, wherein the $C_{1-3}$ alkyl, $C_{2-3}$ alkenyl, and $C_{2-3}$ alkynyl each are optionally substituted by one or more halo;
n represents 0 to 5;
each p independently represents 0, 1 or 2; and
each q independently represents 1 or 2,
provided that the compound is not rel-(1R)-((2S)-4-methylpyrrolidin-2-yl)(phenyl)methanol.

2. The compound according to claim 1, or a pharmaceutically acceptable salt thereof, wherein $R^1$ represents $C_{1-6}$ alkyl optionally substituted by one or more F.

3. The compound according to claim 1, or a pharmaceutically acceptable salt thereof, wherein:
each X independently represents halo, $R^a$, —CN, —N$_3$, —N(R$^b$)R$^c$, —NO$_2$ or OR$^d$, wherein $R^a$ represents $C_{1-4}$ alkyl optionally substituted by one or more F, and R$^b$, R$^c$ and R$^d$ each independently represent H or $C_{1-4}$ alkyl optionally substituted by one or more F.

4. The compound according to claim 1, or a pharmaceutically acceptable salt thereof, wherein n represents 0, 1, 2 or 3.

5. The compound according to claim 4, or a pharmaceutically acceptable salt thereof, wherein each X independently represents F, Cl, —NH$_2$, —CF$_3$ or —OH.

6. The compound according to claim 1, wherein the compound is a compound of formula IH:

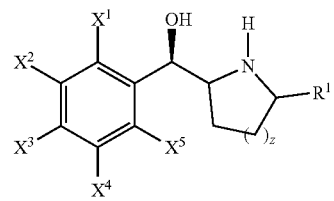

(IH)

or a pharmaceutically acceptable salt thereof.

7. The compound according to claim 1, or a pharmaceutically acceptable salt thereof, wherein z represents 1 or 2.

8. A pharmaceutical composition comprising a compound, and optionally one or more pharmaceutically acceptable adjuvant, diluent and/or carrier, wherein the compound is a compound of formula IF:

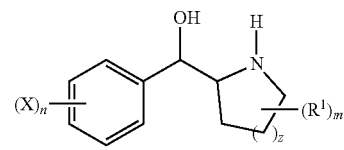

(IA)

or a pharmaceutically acceptable salt thereof, wherein:
z represents 0, 1 or 2;
when z represents 0 then m represents 0 to 5, or when z represents 1 then m represents 1 to 7 or when z represents 2 then m represents 0 to 9;
each $R^1$ independently represents $C_{1-6}$ alkyl, $C_{2-6}$ alkenyl, or $C_{2-6}$ alkynyl each optionally substituted by one or more halo;
each X independently represents halo, $R^a$, —CN, —N$_3$, —N(R$^b$)R$^c$, —NO$_2$, —ONO$_2$, —OR$^d$, —S(O)$_p$R$^e$ or —S(O)$_q$N(R$^f$)R$^g$;

$R^a$ represents $C_{1-6}$ alkyl, $C_{2-6}$ alkenyl, or $C_{2-6}$ alkynyl each optionally substituted by one or more groups independently selected from G;

each $R^b$, $R^e$, $R^d$, $R^e$, $R^f$ and $R^g$ independently represents H or $C_{1-6}$ alkyl, $C_{2-6}$ alkenyl, or $C_{2-6}$ alkynyl each optionally substituted by one or more groups independently selected from G;

or alternatively any of $R^b$ and $R^e$ and/or $R^f$ and $R^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O, wherein the $C_{1-3}$ alkyl, $C_{2-3}$ alkenyl, and $C_{2-3}$ alkynyl each are optionally substituted by one or more halo;

G represents halo, —CN, —N($R^{a1}$)$R^{b1}$, —OR$^{c1}$, —S(O)$_p$R$^{d1}$, —S(O)$_q$N($R^{e1}$)$R^{f1}$ or =O;

each $R^{a1}$, $R^{b1}$, $R^{c1}$, $R^{d1}$, $R^{e1}$ and $R^{f1}$ independently represents H or $C_{1-6}$ alkyl, $C_{2-6}$ alkenyl, or $C_{2-6}$ alkynyl each optionally substituted by one or more halo;

or alternatively any of $R^{a1}$ and $R^{b1}$ and/or $R^{e1}$ and $R^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O, wherein the $C_{1-3}$ alkyl, $C_{2-3}$ alkenyl, and $C_{2-3}$ alkynyl each are optionally substituted by one or more halo;

n represents 0 to 5;

each p independently represents 0, 1 or 2; and each q independently represents 1 or 2.

9. A method of treating hyperglycaemia or a disorder characterized by hyperglycaemia comprising administering to a patient in need thereof a therapeutically effective amount of a compound, or a pharmaceutically acceptable salt thereof, wherein the compound is a compound of formula IF:

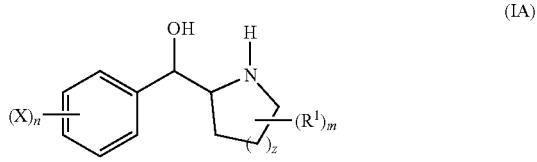

(IA)

or a pharmaceutically acceptable salt thereof, wherein:

z represents 0, 1 or 2;

when z represents 0 then m represents 0 to 5, or when z represents 1 then m represents 0 to 7 or when z represents 2 then m represents 0 to 9;

each $R^1$ independently represents $C_{1-6}$ alkyl, $C_{2-6}$ alkenyl, or $C_{2-6}$ alkynyl each optionally substituted by one or more halo;

each X independently represents halo, $R^a$, —CN, —N$_3$, —N($R^b$)$R^c$, —NO$_2$, —ONO$_2$, —OR$^d$, —S(O)$_p$R$^e$ or —S(O)$_q$N($R^f$)$R^g$;

$R^a$ represents $C_{1-6}$ alkyl, $C_{2-6}$ alkenyl, or $C_{2-6}$ alkynyl each optionally substituted by one or more groups independently selected from G;

each $R^b$, $R^e$, $R^d$, $R^e$, $R^f$ and $R^g$ independently represents H or $C_{1-6}$ alkyl, $C_{2-6}$ alkenyl, or $C_{2-6}$ alkynyl each optionally substituted by one or more groups independently selected from G;

or alternatively any of $R^b$ and $R^e$ and/or R and $R^g$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O, wherein the $C_{1-3}$ alkyl, $C_{2-3}$ alkenyl, and $C_{2-3}$ alkynyl each are optionally substituted by one or more halo;

G represents halo, —CN, —N($R^{a1}$)$R^{b1}$, —OR$^{c1}$, —S(O)$_p$R$^{d1}$, —S(O)$_q$N($R^{e1}$)$R^{f1}$ or =O;

each $R^{a1}$, $R^{b1}$, $R^{c1}$, $R^{d1}$, $R^{e1}$ and $R^{f1}$ independently represents H or $C_{1-6}$ alkyl, $C_{2-6}$ alkenyl, or $C_{2-6}$ alkynyl each optionally substituted by one or more halo;

or alternatively any of $R^{a1}$ and $R^{b1}$ and/or $R^{e1}$ and $R^{f1}$ may be linked together to form, together with the nitrogen atom to which they are attached, a 4- to 6-membered ring, which ring optionally contains one further heteroatom and which ring optionally is substituted by one or more groups independently selected from halo, $C_{1-3}$ alkyl, $C_{2-3}$ alkenyl, $C_{2-3}$ alkynyl, and =O, wherein the $C_{1-3}$ alkyl, $C_{2-3}$ alkenyl, and $C_{2-3}$ alkynyl each are optionally substituted by one or more halo;

n represents 0 to 5;

each p independently represents 0, 1 or 2; and each q independently represents 1 or 2.

10. The method according to claim 9, wherein the hyperglycaemia or disorder characterized by hyperglycaemia is type 2 diabetes.

11. The method according to claim 9, wherein the patient displays severe insulin resistance.

12. The method according to claim 9, wherein the disorder characterised by hyperglycaemia is selected from the group consisting of Rabson-Mendenhall syndrome, Donohue's syndrome, Type A and Type B syndromes of insulin resistance, the HAIR-AN syndromes, pseudoacromegaly, and lipodystrophy.

13. A combination product comprising:

(a) a compound; and (b) one or more other therapeutic agent that is useful in the treatment of hyperglycaemia or a disorder characterized by hyperglycaemia, wherein each of components (a) and (b) is formulated in admixture, optionally with one or more a pharmaceutically-acceptable adjuvant, diluent or carrier; and wherein the compound is a compound of formula IF:

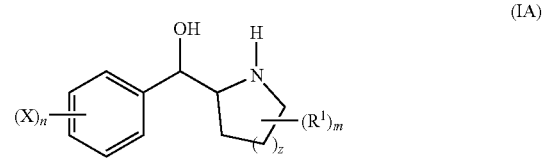

(IA)

or a pharmaceutically acceptable salt thereof, wherein:

z represents 0, 1 or 2;

when z represents 0 then m represents 0 to 5, or when z represents 1 then m represents 0 to 7 or when z represents 2 then m represents 0 to 9;

each $R^1$ independently represents $C_{1-6}$ alkyl, $C_{2-6}$ alkenyl, or $C_{2-6}$ alkynyl each optionally substituted b one or more halo;

each X independently represents halo, $R^a$, —CN, —N$_3$, —N($R^b$)$R^c$, —NO$_2$, —ONO$_2$, —OR$^d$, —S(O)$_p$R$^e$ or —S(O)$_q$N($R^f$)$R^g$;

R$^a$ represents C$_{1-6}$ alkyl, C$_{2-6}$ alkenyl, or C$_{2-6}$ alkynyl each optionally substituted by one or more groups independently selected from G;

each R$^b$, R$^e$, R$^d$, R$^e$, R$^f$ and R$^g$ independently represents H or C$_{1-6}$ alkyl, C$_{2-6}$ alkenyl, or C$_{2-6}$ alkynyl each optionally substituted by one or more groups independently selected from G;

or alternatively any of R$^b$ and R$^e$ and/or R$^f$ and R$^g$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl, C$_{2-3}$ alkenyl, C$_{2-3}$ alkynyl, and =O, wherein the C$_{1-3}$ alkyl, C$_{2-3}$ alkenyl, and C$_{2-3}$ alkynyl each are optionally substituted by one or more halo;

G represents halo, —CN, —N(R$^{a1}$)R$^{b1}$, —OR$^{c1}$, —S(O)$_p$R$^{d1}$, —S(O)$_q$N(R$^{e1}$)R$^{f1}$ or =O;

each R$^{a1}$, R$^{b1}$, R$^{c1}$, R$^{d1}$, R$^{e1}$ and R$^{f1}$ independently represents H or C$_{1-6}$ alkyl, C$_{2-6}$ alkenyl, or C$_{2-6}$ alkynyl each optionally substituted by one or more halo;

or alternatively any of R$^{a1}$ and R$^{b1}$ and/or R$^{e1}$ and R$^{f1}$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl, C$_{2-3}$ alkenyl, C$_{2-3}$ alkynyl, and =O, wherein the C$_{1-3}$ alkyl, C$_{2-3}$ alkenyl, and C$_{2-3}$ alkynyl each are optionally substituted by one or more halo;

n represents 0 to 5;

each p independently represents 0, 1 or 2; and each q independently represents 1 or 2.

14. A kit-of-parts comprising:
(a) a pharmaceutical composition comprising a compound as defined in claim 1, and optionally one or more pharmaceutically acceptable adjuvant, diluent and/or carrier, and
(b) one or more other therapeutic agent that is useful in the treatment of hyperglycaemia or a disorder characterized by hyperglycaemia, optionally in admixture with one or more pharmaceutically-acceptable adjuvant, diluent or carrier, which components (a) and (b) are each provided in a form that is suitable for administration in conjunction with the other, wherein the compound is a compound of formula IF:

(IA)

or a pharmaceutically acceptable salt thereof, wherein:

z represents 0, 1 or 2;

when z represents 0 then m represents 0 to 5, or when z represents 1 then m represents 0 to 7 or when z represents 2 then m represents 0 to 9;

each R$^1$ independently represents C$_{1-6}$ alkyl, C$_{2-6}$ alkenyl, or C$_{2-6}$ alkynyl each optionally substituted by one or more halo;

each X independently represents halo, R$^a$, —CN, —N$_3$, —N(R$^b$)R$^c$, —NO$_2$, —ONO$_2$, —OR$^d$, —S(O)$_p$R$^e$ or —S(O)$_q$N(R$^f$)R$^g$;

R$^a$ represents C$_{1-6}$ alkyl, C$_{2-6}$ alkenyl, or C$_{2-6}$ alkynyl each optionally substituted by one or more groups independently selected from G;

each R$^b$, R$^e$, R$^d$, R$^e$, R$^f$ and R$^g$ independently represents H or C$_{1-6}$ alkyl, C$_{2-6}$ alkenyl, or C$_{2-6}$ alkynyl each optionally substituted by one or more groups independently selected from G;

or alternatively any of R$^b$ and R$^e$ and/or R$^f$ and R$^g$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl, C$_{2-3}$ alkenyl, C$_{2-3}$ alkynyl, and =O, wherein the C$_{1-3}$ alkyl, C$_{2-3}$ alkenyl, and C$_{2-3}$ alkynyl each are optionally substituted by one or more halo;

G represents halo, —CN, —N(R$^{a1}$)R$^{b1}$, —OR$^{c1}$, —S(O)$_p$R$^{d1}$, —S(O)$_q$N(R$^{e1}$)R$^{f1}$ or =O;

each R$^{a1}$, R$^{b1}$, R$^{c1}$, R$^{d1}$, R$^{e1}$ and R$^{f1}$ independently represents H or C$_{1-6}$ alkyl, C$_{2-6}$ alkenyl, or C$_{2-6}$ alkynyl each optionally substituted by one or more halo;

or alternatively any of R$^{a1}$ and R$^{b1}$ and/or R$^{e1}$ and R$^{f1}$ may be linked together to form, together with the nitrogen atom to which they are attached, a 4- to 6-membered ring, which ring optionally contains one further heteroatom and which ring optionally is substituted by one or more groups independently selected from halo, C$_{1-3}$ alkyl, C$_{2-3}$ alkenyl, C$_{2-3}$ alkynyl, and =O, wherein the C$_{1-3}$ alkyl, C$_{2-3}$ alkenyl, and C$_{2-3}$ alkynyl each are optionally substituted by one or more halo;

n represents 0 to 5;

each p independently represents 0, 1 or 2; and each q independently represents 1 or 2.

15. A process for the preparation of a compound as defined in claim 1, or a pharmaceutically acceptable salt thereof, comprising the step of:

deprotection of a compound of the following formula:

(IA)

wherein n, m, X and R$^1$ are as defined in claim 1, wherein ring A is (VII)

wherein z is as defined in claim 1, and wherein PG$^4$ represents a suitable protecting group.

16. The compound according to claim 6, or a pharmaceutically acceptable salt thereof, wherein:

$X^1$ and $X^5$ each represent H, F or Cl; and $X^2$, $X^3$ and $X^4$ each independently represent H, halo, $R^a$, —CN, —$N_3$, —N($R^b$)$R^c$, —$NO_2$ or —O$R^d$;

wherein $R^a$ represents $C_{1-4}$ alkyl optionally substituted by one or more F, $R^b$, $R^c$ and $R^d$ each independently represent H or $C_{1-4}$ alkyl optionally substituted by one or more F.

* * * * *